(12) United States Patent
Kimura et al.

(10) Patent No.: US 11,602,577 B2
(45) Date of Patent: Mar. 14, 2023

(54) WATER-ABSORBING AGENT AND METHOD FOR PRODUCING SAME, AND ABSORBENT ARTICLE PRODUCED USING WATER-ABSORBING AGENT

(71) Applicant: NIPPON SHOKUBAI CO., LTD., Osaka (JP)

(72) Inventors: Kazuki Kimura, Himeji (JP); Nobuya Tanaka, Himeji (JP); Yuki Tanaka, Himeji (JP); Daisuke Takeda, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 1203 days.

(21) Appl. No.: 16/088,638

(22) PCT Filed: Mar. 28, 2017

(86) PCT No.: PCT/JP2017/012562
§ 371 (c)(1),
(2) Date: Sep. 26, 2018

(87) PCT Pub. No.: WO2017/170501
PCT Pub. Date: Oct. 5, 2017

(65) Prior Publication Data
US 2019/0125921 A1    May 2, 2019

(30) Foreign Application Priority Data
Mar. 28, 2016  (JP) .............................. JP2016-063097

(51) Int. Cl.
*B01J 20/02*    (2006.01)
*B01J 20/26*    (2006.01)
(Continued)

(52) U.S. Cl.
CPC ............... *A61L 15/24* (2013.01); *A61L 15/60* (2013.01); *B01J 20/02* (2013.01); *B01J 20/26* (2013.01);
(Continued)

(58) Field of Classification Search
None
See application file for complete search history.

(56) References Cited

U.S. PATENT DOCUMENTS 5,118,719 A    6/1992  Lind
5,154,713 A    10/1992 Lind
(Continued)

FOREIGN PATENT DOCUMENTS

EP    1429703 A2    6/2004
EP    1473010 A1    11/2004
(Continued)

OTHER PUBLICATIONS

International Search Report dated Jun. 20, 2017 issued in PCT/JP2017/012562.
(Continued)

*Primary Examiner* — Joseph D Anthony
(74) *Attorney, Agent, or Firm* — Harness Dickey & Pierce P.L.C.

(57) ABSTRACT

Provided is a water-absorbing agent having an excellent ability to absorb and retain liquid and an excellent liquid suction power. The water-absorbing agent contains a polyacrylic acid (salt)-based water-absorbing resin as a main component and satisfies all of the following physical properties (a) to (e): (a) a weight average particle diameter (D50) is 300 μm or more and less than 400 μm; (b) a proportion of particles with a particle diameter of 600 μm or more and less than 850 μm is less than 10 weight %; (c) an average gap radius is 100 μm or more and less than 180 μm; (d) a CRC
(Continued)

is 28 g/g or more and less than 34 g/g; and (e) an AAP is 24 g/g or more.

8 Claims, 4 Drawing Sheets

(51) Int. Cl.

| | | |
|---|---|---|
| *A61L 15/24* | (2006.01) | |
| *C08F 20/06* | (2006.01) | |
| *C08J 3/12* | (2006.01) | |
| *A61L 15/60* | (2006.01) | |
| *C08F 220/06* | (2006.01) | |
| *C08L 33/02* | (2006.01) | |
| *B29B 9/12* | (2006.01) | |
| *C08J 3/075* | (2006.01) | |
| *C08J 3/24* | (2006.01) | |
| *B01J 20/28* | (2006.01) | |
| *B01J 20/30* | (2006.01) | |
| *A61F 13/53* | (2006.01) | |

(52) U.S. Cl.
CPC ....... *B01J 20/267* (2013.01); *B01J 20/28004* (2013.01); *B01J 20/28016* (2013.01); *B01J 20/28045* (2013.01); *B01J 20/28047* (2013.01); *B01J 20/3021* (2013.01); *B01J 20/3085* (2013.01); *B29B 9/12* (2013.01); *C08F 20/06* (2013.01); *C08F 220/06* (2013.01); *C08J 3/075* (2013.01); *C08J 3/12* (2013.01); *C08J 3/24* (2013.01); *C08J 3/245* (2013.01); *C08L 33/02* (2013.01); *A61F 2013/530481* (2013.01); *B01J 2220/68* (2013.01); *B29B 2009/125* (2013.01); *C08F 2810/20* (2013.01); *C08J 2333/02* (2013.01)

(56) References Cited

U.S. PATENT DOCUMENTS

| | | | |
|---|---|---|---|
| 6,184,433 B1 | 2/2001 | Harada et al. | |
| 2002/0007170 A1 | 1/2002 | Wada et al. | |
| 2002/0120074 A1 | 8/2002 | Wada et al. | |
| 2003/0176589 A1 | 9/2003 | Wada et al. | |
| 2003/0181115 A1 | 9/2003 | Nagasuna et al. | |
| 2004/0019342 A1 | 1/2004 | Nagasuna et al. | |
| 2004/0039360 A1 | 2/2004 | Ehrnsperger et al. | |
| 2005/0070671 A1 | 3/2005 | Torii et al. | |
| 2005/0272600 A1 | 12/2005 | Wada et al. | |
| 2006/0073969 A1 | 4/2006 | Torii et al. | |
| 2006/0204755 A1 | 9/2006 | Torii et al. | |
| 2007/0066167 A1* | 3/2007 | Wada .................. C08J 3/245 442/101 | |
| 2007/0078248 A1* | 4/2007 | Adachi ............. A61F 13/15211 526/317.1 | |
| 2007/0111004 A1 | 5/2007 | Handa et al. | |
| 2007/0123658 A1* | 5/2007 | Torii ...................... A61L 15/60 525/329.7 | |
| 2007/0134492 A1 | 6/2007 | Ehrnsperger et al. | |
| 2007/0141338 A1* | 6/2007 | Ishizaki ................... C08J 3/12 502/402 | |
| 2009/0118432 A1 | 5/2009 | Fukudome et al. | |
| 2009/0182294 A1 | 7/2009 | Ikeuchi et al. | |
| 2009/0215617 A1 | 8/2009 | Kimura et al. | |
| 2009/0281232 A1 | 11/2009 | Ikeuchi et al. | |
| 2010/0308263 A1 | 12/2010 | Torii et al. | |
| 2011/0313113 A1 | 12/2011 | Sakamoto et al. | |
| 2012/0258851 A1 | 10/2012 | Nakatsuru et al. | |
| 2013/0026412 A1* | 1/2013 | Machida ................ B29B 9/16 525/384 | |
| 2013/0101851 A1 | 4/2013 | Takaai et al. | |
| 2013/0130017 A1 | 5/2013 | Takatori et al. | |
| 2014/0193641 A1 | 7/2014 | Torii et al. | |
| 2014/0296465 A1 | 10/2014 | Sakamoto et al. | |
| 2015/0217270 A1 | 8/2015 | Ueda et al. | |
| 2015/0259494 A1 | 9/2015 | Takaai et al. | |
| 2016/0207226 A1* | 7/2016 | Torii ...................... B29B 7/422 | |
| 2016/0332141 A1 | 11/2016 | Machida et al. | |
| 2018/0001300 A1 | 1/2018 | Nakatsuru et al. | |
| 2019/0275192 A1* | 9/2019 | Torii ...................... B29B 9/06 | |

FOREIGN PATENT DOCUMENTS

| | | | |
|---|---|---|---|
| EP | 1730219 A1 | 12/2006 | |
| EP | 2557095 A1 | 2/2013 | |
| EP | 3312218 A1 | 4/2018 | |
| JP | H5237378 A | 9/1993 | |
| JP | H09124710 A | 5/1997 | |
| JP | H11060975 A | 3/1999 | |
| JP | H11315148 A | 11/1999 | |
| JP | 2000038407 A | 2/2000 | |
| JP | 2002045395 A | 2/2002 | |
| JP | 2003290290 A | 10/2003 | |
| JP | 20041355 A | 1/2004 | |
| JP | 200529751 A | 2/2005 | |
| JP | 2005-111474 A | 4/2005 | |
| JP | 2005097519 A | 4/2005 | |
| JP | 2005536292 A | 12/2005 | |
| JP | 2006-55833 A | 3/2006 | |
| JP | 2006-57075 A | 3/2006 | |
| JP | 200951077 A | 3/2009 | |
| JP | 2009509722 A | 3/2009 | |
| JP | 2010502415 A | 1/2010 | |
| JP | 2011074401 A | 4/2011 | |
| JP | 201376073 A | 4/2013 | |
| JP | 2013213083 A | 10/2013 | |
| WO | WO-03026707 A2 | 4/2003 | |
| WO | WO-2005027986 A1 | 3/2005 | |
| WO | 2005092956 A1 | 10/2005 | |
| WO | WO-2005092955 A1 | 10/2005 | |
| WO | WO-2007004529 A1 | 1/2007 | |
| WO | WO-2007037522 A1 | 4/2007 | |
| WO | WO-2008026783 A1 | 3/2008 | |
| WO | WO-2011126079 A1 | 10/2011 | |
| WO | WO-2012023433 A1 | 2/2012 | |
| WO | WO-2012174026 A1 | 12/2012 | |
| WO | WO-2013002387 A1 | 1/2013 | |
| WO | WO-2014034897 A1 | 3/2014 | |
| WO | WO-2014140751 A1 | 9/2014 | |
| WO | WO-2016/111223 A1 | 7/2016 | |
| WO | WO-2016204302 A1 | 12/2016 | |

OTHER PUBLICATIONS

International Preliminary Report on Patentability dated Oct. 11, 2018 issued in PCT/JP2017/012562.

European Search Report dated Sep. 12, 2019 for EP Application No. 17775038.7.

* cited by examiner

WATER-ABSORBING AGENT AND METHOD FOR PRODUCING SAME, AND ABSORBENT ARTICLE PRODUCED USING WATER-ABSORBING AGENT

PRIORITY STATEMENT

This application is a national stage application under 35 U.S.C. § 371 of PCT International Application No. PCT/JP2017/012562, which has an International filing date of 28 Mar. 2017 and claims priority to Japanese Patent Application No. JP 2016-063097 which has a filing date of 28 Mar. 2016. The contents of each application recited above are incorporated herein by reference in their entirety.

TECHNICAL FIELD

The present invention relates to a water-absorbing agent, a method for producing the water-absorbing agent, and an absorbent article which uses the water-absorbing agent. More specifically, the present invention relates to: a water-absorbing agent which has excellent water absorption performance and excellent ability to suck up liquid; a method for producing the water-absorbing agent; and an absorbent article which uses the water-absorbing agent, examples of the absorbent article including a disposable diaper and a sanitary napkin.

BACKGROUND ART

Water-absorbing resin is a water-swellable, water-insoluble polymer gelling agent. Water-absorbing resin is used in various applications including use in absorbent articles such as disposable diapers and sanitary napkins, agricultural and horticultural water retaining agents for soil, and industrial waterproofing agents. Many types of monomers and hydrophilic polymers have been proposed as raw materials of such water-absorbing resin. From the viewpoint of water absorption performance and production cost of the water-absorbing resin, a polyacrylic acid (salt)-based water-absorbing resin containing an acrylic acid and/or a salt thereof (hereinafter referred to as "acrylic acid (salt)") as a monomer(s) is most often used as such water-absorbing resin.

Recently, absorbent articles such as disposable diapers and sanitary napkins have been undergoing a trend of being reduced in thickness by, for example, increasing a used amount of water-absorbing resin per absorbent article. In connection with this trend, there has been a demand for high performance of the water-absorbing resin. For example, there have been developed water-absorbing resins in which fluid retention capacity under pressure and water absorption speed, which are physical properties in a trade-off relationship, are concurrently achieved (Patent Literatures 1 and 2). There have also been developed water-absorbing resins in which water absorption capacity and liquid permeability are concurrently attained (Patent Literatures 3 to 9).

Furthermore, recently there has been a demand for absorbent articles such as disposable diapers and sanitary napkins to have many types of added value (increased performance) other than the thickness reduction mentioned above. In connection with this demand, there has been a demand for water-absorbing resin to have many physical properties. In many cases, the absorbent article comes into direct contact with a person's skin, and there is therefore the demand for physical properties of the water-absorbing resin in relation to safety, comfort, and the like of the absorbent article. Specific examples of such physical properties for which there is a demand include water soluble content, urine resistance, antibacterial property, deodorizing property, air permeability, coloration resistance (degree of whiteness), capillary suction power, and liquid diffusion property.

Under the above-described circumstances, there have been developed water-absorbing resins such as: water-absorbing resins in which urine resistance is improved by use of a chelating agent, a chain transfer agent, and the like (Patent Literatures 10 to 12, 24, and 25); a water-absorbing resin in which coloration resistance (degree of whiteness) is improved (Patent Literature 13); and a water-absorbing resin in which air permeability is improved by controlling particle size, fluid retention capacity under pressure, and the like (Patent Literature 14).

There have also been developed absorbent articles, which use a water-absorbing resin, such as: an absorbent article in which re-wet of the absorbent article is improved by defining performance (for example, PDAUP) of the water-absorbing resin used (Patent Literature 15); and absorbent articles in which liquid absorption amount of the absorbent articles is improved by defining a capillary fluid retention capacity of the water-absorbing resin used (Patent Literatures 16 and 17).

Furthermore, there have been proposed, for example: a water-absorbing agent composition having an improved liquid suck-up property (Patent Literature 18); an absorbent body having an excellent capability to diffuse absorbed liquid (Patent Literature 19); a water-absorbing agent capable of diffusing an absorbed water-based liquid over a wide area (Patent Literature 20); an absorbent body which uses water-absorbing polymer particles, which have been defined in accordance with a K(t) test method, at a high concentration of 90 weight % or more of an absorbent body (Patent Literature 26); and a water-absorbing agent for which a chemical cross-linking index, chemical cross-linking index under load, and the like have been defined (Patent Literature 21).

Patent Literature 22, which was not published as of the priority date of the present application, discloses a water-absorbing agent for which gap fluid retention capacity is defined. Patent Literature 3 and Patent Literature 23, the latter of which was not published as of the priority date of the present application, disclose methods for producing a water-absorbing agent for which an average gel particle diameter after gel-crushing is defined.

CITATION LIST

Patent Literature

Patent Literature 1

Japanese Patent Application Publication, Tokukaihei, No. 11-060975

Patent Literature 2

Pamphlet of International Publication No. WO 2007/004529

Patent Literature 3

Pamphlet of International Publication No. WO 2011/126079

Patent Literature 4

Pamphlet of International Publication No. WO 2012/023433

Patent Literature 5

Japanese Translation of PCT International Application, Tokuhyo, No. 2009-509722

Patent Literature 6

Japanese Patent Application Publication, Tokukai, No. 2005-097519

Patent Literature 7

Japanese Patent Application Publication, Tokukai, No. 2011-074401

Patent Literature 8

Japanese Patent Application Publication, Tokukai, No. 2013-076073

Patent Literature 9

Japanese Patent Application Publication, Tokukai, No. 2013-213083

Patent Literature 10

Japanese Patent Application Publication, Tokukaihei, No. 9-124710

Patent Literature 11

Japanese Patent Application Publication, Tokukai, No. 2000-038407

Patent Literature 12

Japanese Patent Application Publication, Tokukaihei, No. 11-315148

Patent Literature 13

Japanese Patent Application Publication, Tokukai, No. 2005-029751

Patent Literature 14

Japanese Patent Application Publication, Tokukai, No. 2002-045395

Patent Literature 15

Pamphlet of International Publication No. WO 2014/140751

Patent Literature 16

Specification of European Patent Application Publication No. 1473010

Patent Literature 17

Japanese Translation of PCT International Application, Tokuhyo, No. 2005-536292

Patent Literature 18

Pamphlet of International Publication No. WO 2007/037522

Patent Literature 19

Specification of European Patent Application Publication No. 1429703

Patent Literature 20

Pamphlet of International Publication No. WO 2008/026783

Patent Literature 21

Pamphlet of International Publication No. WO 2005/027986

Patent Literature 22

Pamphlet of International Publication No. WO 2016/111223

Patent Literature 23

Pamphlet of International Publication No. WO 2016/204302

Patent Literature 24

Pamphlet of International Publication No. WO 2005/092955

Patent Literature 25

Pamphlet of International Publication No. WO 2013/002387

Patent Literature 26

Pamphlet of International Publication No. WO 2012/174026

SUMMARY OF INVENTION

Technical Problem

In connection with the above-described increase in performance of absorbent articles such as disposable diapers and sanitary napkins, there has also been a demand for an increase in performance of the water-absorbing resin which is contained in these absorbent articles. To date there have been technological improvements developed with the objective of improving water absorption performance in particular (Patent Literatures 1 to 23). However, absorbent articles such as disposable diapers and sanitary napkins (particularly disposable diapers) are evolving rapidly, and the performance thereof is now being further subdivided. As such, it is becoming impossible to further improve the performance of individual types of disposable diapers by merely improving conventional performance (fluid retention capacity, water absorption speed, liquid permeability, and the like). Note that basic performance of a water-absorbing resin is defined by EDANA methods. Worldwide Strategic Partners (WSP) defines more than 10 basic physical properties, such as CRC, of water-absorbing resins. Many physical property parameters other than those of the EDANA methods are proposed in Patent Literatures 1 to 23 and the like.

For example, in development of a water-absorbing resin to be adapted to a certain disposable diaper, the water-absorbing resin may be adapted by sacrificing, to a certain degree, a fluid retention capacity without pressure (for example, CRC) in order to improve fluid retention capacity under pressure (for example, absorption against pressure (AAP)) and liquid permeability (for example, saline flow conductivity (SFC) and gel bed permeability (GBP)) and thereby adjusting the overall balance of performance. However, if such a customized water-absorbing resin is employed other types of disposable diapers, in some cases the water-absorbing resin would not be adapted to that disposable diaper and could result in problems such as discomfort during wearing due to urine leakage and/or the like.

Furthermore, recently, absorbent articles such as disposable diapers and sanitary napkins been changed so as to use an increasing amount of water-absorbing resin per absorbent article. As such, as a measure against urine leakage from disposable diapers in particular, there has been an increasing demand for water-absorbing resin to provide performance which had conventionally been handled by pulp, such as liquid suction power via capillary action and diffusion ability via capillary action.

Absorbent bodies which use a water-absorbing agent (water-absorbing resin) have been evaluated in terms of re-wet and a diffusion property. However, these are each evaluations of the absorbent body in a plane. These evaluations do not take into account the fact that in actual usage, the absorbent body will be used along a curved surface in line with a human body (i.e., buttocks). As such, it has been found that conventional water-absorbing agents do not exhibit sufficient capabilities.

An object of the present invention lies in providing a water-absorbing agent, containing a water-absorbing resin as a main component, which can be employed in a wide variety of absorbent articles (particularly disposable diapers). In developing such a water-absorbing agent, the inventors of the present invention evaluated and analyzed water-absorbing agents, absorbent bodies (a mixture of a water-absorbing agent and pulp), and absorbent articles from a multitude of perspectives. As a result, the inventors discovered that the performance which is universally demanded in a wide variety of absorbent articles is not the basic physical properties defined by EDANA methods or the physical properties parameters proposed heretofore, but rather the liquid suction power of a water-absorbing agent.

Conventionally, the liquid suction power of a water-absorbing agent has been evaluated as capillary absorption capacity substantially without load (Patent Literatures 16 and 19). However, there has been little evaluation of the liquid suction power as general water absorption performance (fluid retention capacity without pressure, fluid retention capacity under pressure, liquid permeability, etc.). The inventors of the present invention, however, have discovered that in a water-absorbing agent having a specific particle size distribution, a specific CRC, and a specific AAP, controlling the ability of water-absorbing agent itself to suck liquid under a pressure (i.e., an updraw fluid retention capacity under load, with a load of 2.07 kPa), which ability is not mentioned in Patent Literatures 16 and 19, makes it possible to provide a water-absorbing agent which is universally demanded in a wide variety of absorbent articles. In other words, an object of the present invention lies in providing: a water-absorbing agent which has an excellent ability to absorb and retain liquid (CRC, AAP) and an excellent liquid suction power (updraw fluid retention capacity under load); a method for producing the water-absorbing agent; and an absorbent article which uses the water-absorbing agent.

Solution to Problem

After examining how to attain the above object, the inventors of the present invention found the solutions described below.

The inventors of the present invention conducted diligent research in order to attain the above object, and as a result they discovered that, with regards to an average gap radius (also referred to as "average space radius"; see Patent Literatures 18, 19, and 21), an average gap radius under pressure (also referred to as "pressurized void average radius index"; see Patent Literature 20) and the like, in a case where a water-absorbing agent has a specific particle size distribution, a specific CRC, and a specific AAP, there is a very high correlation between the average gap radius without load of the water-absorbing agent and the liquid suction power under load of the water-absorbing agent. Furthermore, the inventors discovered that carrying out gel-crushing, foaming polymerization, and the like in a specific manner increases the surface area of a water-absorbing agent and allows the water-absorbing agent to have a higher liquid suction power.

In general, a height to which a liquid is sucked up by capillary action is inversely proportional to a width (radius) of a capillary. With regards to the liquid suction power of a water-absorbing agent, considering the width (radius) of a capillary as being an average gap radius between particles of the water-absorbing agent allowed the inventors to ascertain that the average gap radius greatly affects the liquid suction power of the water-absorbing agent.

In other words, the inventors found that by adjusting the average gap radius to be in a specific range in a water-absorbing agent which has a specific particle size distribution, a specific CRC, and a specific AAP, it is possible not only to improve conventional water absorption performance as defined by an EDANA and the like, but also to improve, for example, liquid suction power under load and the later-described core acquisition of an absorbent body in an inclined state. Furthermore, the inventors discovered that a water-absorbing agent in accordance with an embodiment of the present invention can be obtained in a case where: a particle diameter of a particulate hydrogel before drying is controlled by gel-crushing a hydrogel to a specific particle diameter; and particle size, CRC, and the like of a water-absorbing resin powder before surface crosslinking are controlled. With this knowledge, the inventors discovered a water-absorbing agent and a method for producing the water-absorbing agent which successfully attain the above object. The inventors thus arrived at the present invention. Embodiments of the present invention are described below.

A method for producing a water-absorbing agent in accordance with an embodiment of the present invention is a method for producing a water-absorbing agent containing a polyacrylic acid (salt)-based water-absorbing resin as a main component, including the steps of:

(A) polymerizing an aqueous monomer solution so that a crosslinked hydrogel polymer is obtained, the aqueous monomer solution containing a monomer and at least one polymerizable internal crosslinking agent, the monomer containing acrylic acid (salt) as a main component;

(B) gel-crushing the crosslinked hydrogel polymer such that the crosslinked hydrogel polymer has a weight average particle diameter (D50) of 500 μm or more and less than 1500 μm, and then drying the crosslinked hydrogel polymer so that a dried polymer is obtained;

(C) pulverizing the dried polymer and then classifying the dried polymer so that a water-absorbing resin powder is obtained; and (D) surface-crosslinking the water-absorbing resin powder with use of at least one surface-crosslinking agent so that water-absorbing resin particles are obtained, the water-absorbing resin powder obtained through the steps (A) to (C) satisfying the following physical properties (1) to (4):

(1) a CRC is 35 g/g or more;

(2) a weight average particle diameter (D50) is 300 μm or more and less than 400 μm;

(3) a logarithmic standard deviation ($\sigma\zeta$) of a particle size distribution is 0.30 or more and less than 0.40; and (4) an average gap radius is 100 μm or more and less than 300 μm.

A water-absorbing agent in accordance with an embodiment of the present invention includes a polyacrylic acid (salt)-based water-absorbing resin as a main component and satisfies all of the following physical properties (a) to (e):

(a) a weight average particle diameter (D50) is 300 μm or more and less than 400 μm;

(b) a proportion of particles with a particle diameter of 600 μm or more and less than 850 μm is less than 10 weight %;

(c) an average gap radius is 100 μm or more and less than 180 μm;

(d) a CRC is 28 g/g or more and less than 34 g/g; and (e) an AAP is 24 g/g or more.

An absorbent article in accordance with an embodiment of the present invention includes: a liquid permeable top sheet; a liquid impermeable back sheet; and an absorbent body containing the above water-absorbing agent, the absorbent body being sandwiched between the top sheet and the back sheet.

Advantageous Effects of Invention

A water-absorbing agent in accordance with an embodiment of the present invention has not only an excellent ability to absorb and retain liquid, but also an excellent liquid suction power under load. As such, the water-absorbing agent in accordance with an embodiment of the present invention advantageously exhibits an excellent ability to suck up liquid against the force of gravity (in particular, an excellent updraw fluid retention capacity under load). Furthermore, the above effects are not only brought about when the water-absorbing agent is used alone. Even in an absorbent body composed of a mixture of the water-absorbing agent and fibrous pulp, the inherent capillary suction power of the fibrous pulp does counteract the liquid suction power of the water-absorbing agent. Such an absorbent body therefore similarly exhibits an excellent ability to suck up liquid against the force of gravity (in particular, an excellent amount of liquid updrawn by the absorbent body and an excellent updraw distance in an inclined state).

In other words, embodiments of the present invention make it possible to provide a water-absorbing agent which has an excellent ability to absorb and retain liquid and an excellent liquid suction power under load, as well as a method for producing such a water-absorbing agent. In a case where the water-absorbing agent in accordance with an embodiment of the present invention is used in an absorbent article, and particularly a disposable diaper, the absorbent article exhibits excellent water absorption performance. This is because in the three-dimensional structure of the absorbent article during wearing, in a vertical direction, the absorbent body acts against the force of gravity to diffuse an absorbed liquid such as urine, and in a horizontal direction, the absorbent body is used effectively in its entirety. It is therefore possible to provide an absorbent article such as a disposable diaper which, for example, exhibits little urine leakage and provides favorable wearing comfort.

DESCRIPTION OF EMBODIMENTS

Figure 1:
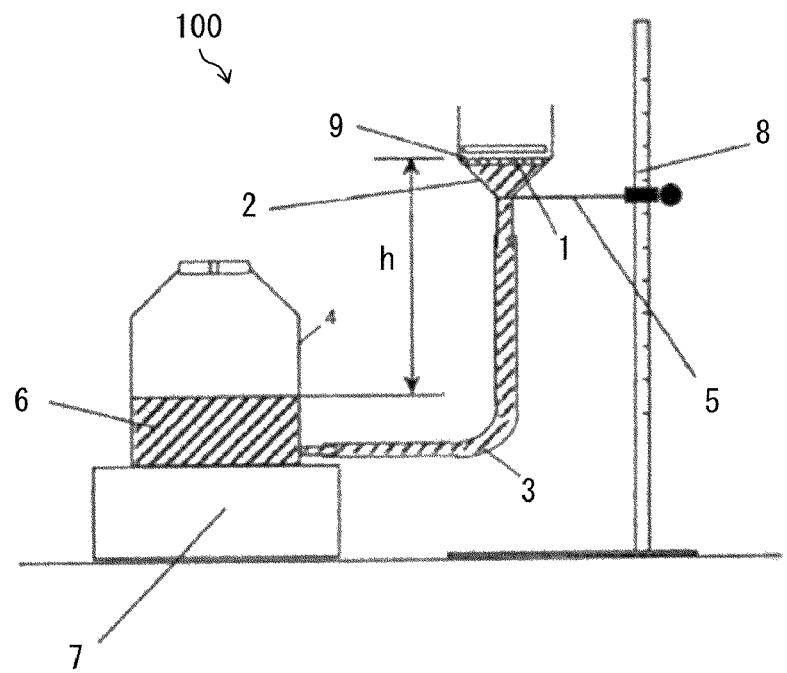
FIG. 1 is an elevational view schematically illustrating a configuration of a measuring apparatus for measuring an average gap radius of a water-absorbing agent.

The following description will discuss in detail a water-absorbing agent, a method for producing the water-absorbing agent, and an absorbent article which uses the water-absorbing agent, each of which is in accordance with an embodiment of the present invention. Note, however, that the present invention is not limited in scope to the description below, and may be altered from the examples below and practiced as appropriate to the extent that such alteration is not a departure from the scope of the present invention. Specifically, the present invention is not limited to the embodiments below, but can be altered by a skilled person in the art within the scope of the claims. An embodiment derived from a proper combination of technical means each disclosed in a different embodiment is also encompassed in the technical scope of the present invention.

[1] Definitions of Terms

[1-1] Water-Absorbing Resin, Water-Absorbing Resin Powder, Water-Absorbing Resin Particle, and Water-Absorbing Agent The term "water-absorbing resin" as used for an embodiment of the present invention means a water-swellable, water-insoluble polymer gelling agent. The expression "water-swellable" indicates a centrifuge retention capacity (CRC) as defined in ERT 441.2-02 of 5 g/g or more. The expression "water-insoluble" indicates extractables (Ext) as defined in ERT 470.2-02 of 50 weight % or less.

The "water-absorbing resin" is preferably a hydrophilic crosslinked polymer that has been obtained by crosslinking and polymerizing unsaturated monomers each of which has a carboxyl group. The water-absorbing resin is not necessarily wholly (that is, 100 weight %) a crosslinked polymer, and can contain an additive and/or the like to the extent that the above-described performance (CRC and Ext) is maintained.

In some cases, the term "water-absorbing resin" may refer to a polymer which is crosslinked only internally (that is, a polymer in which an internal crosslinking density and a surface crosslinking density are substantially the same) or a polymer whose inside and surface are both crosslinked (that is, a polymer in which a surface crosslinking density is higher relative to the internal crosslinking density thereof). Note that in the present specification, for convenience, a polymer which is crosslinked only internally is referred to as a "water-absorbing resin powder", and a polymer whose inside and surface are both crosslinked is referred to as a "water-absorbing resin particle(s)".

The term "water-absorbing agent" as used for an embodiment of the present invention means a water-absorbing resin which is in a state where it can be shipped as an end product. As such, in a case where the "water-absorbing resin powder" and the "water-absorbing resin particles" are to be shipped as-is as end products, the "water-absorbing resin powder" and the "water-absorbing resin particles" are each a "water-absorbing agent". Even in a case where the "water-absorbing resin particles" are made of a composition in which an additive and/or the like has been added, if the particles are to be shipped as an end product, the particles are referred to as a "water-absorbing agent".

The phrase "water-absorbing agent containing a water-absorbing resin as a main component" as used with respect to the present invention means that a proportion of the water-absorbing resin in the water-absorbing agent falls in a range of 50 weight % to 100 weight %. Note that the proportion is preferably 60 weight % or more, more preferably 70 weight % or more, even more preferably 80 weight % or more, and particularly preferably 90 weight % or more. The "water-absorbing agent containing a water-absorbing resin as a main component" may contain, as components other than the water-absorbing resin, water and/or the below described additives at a proportion of 50 weight % or less, and preferably at a proportion falling in a range of 0.01 weight % to 10 weight %.

[1-2] Polyacrylic Acid (Salt)-Based Water-Absorbing Resin

The term "polyacrylic acid (salt)-based water-absorbing resin" as used with respect to the present invention means a water-absorbing resin whose raw material is acrylic acid and/or a salt thereof (hereinafter, "acrylic acid and/or a salt thereof" is expressed as "acrylic acid (salt)"). In other words, the polyacrylic acid (salt)-based water-absorbing resin is a water-absorbing resin in which a polymer has a structural unit derived from acrylic acid (salt) and which has a graft component as an optional component.

Specifically, the polyacrylic acid (salt)-based water-absorbing resin contains acrylic acid (salt) in the following proportions, relative to total content of monomers contributing to a polymerization reaction (excluding internal crosslinking agent(s)): preferably 50 mol % to 100 mol %, more preferably 70 mol % to 100 mol %, even more preferably 90 mol % to 100 mol %, and particularly preferably substantially 100 mol %.

[1-3] EDANA and ERT

The term "EDANA" is an acronym for the European Disposables and Nonwovens Associations. The term "ERT" is an acronym for EDANA Recommended Test Methods. The ERT test methods are European standard (de facto international standard) methods for measuring physical properties of water-absorbing resin. For the present invention, physical properties of water-absorbing resin are measured in conformity with the ERT master copy (revised in 2002; publicly known literature) unless otherwise specified.

[1-3-1] CRC (ERT 441.2-02)

"CRC" is an acronym for "centrifuge retention capacity" and refers to a fluid retention capacity of water-absorbing resin without pressure. Specifically, CRC refers to a fluid retention capacity (unit: g/g) measured after 0.2 g of water-absorbing resin contained in a nonwoven fabric bag is immersed in a large excess of a 0.9 weight % aqueous sodium chloride solution for 30 minutes so as to be allowed to freely swell, and then the water-absorbing resin is drained in a centrifuge (250 G).

[1-3-2] AAP (ERT 442.2-02)

The term "AAP" is an acronym for "absorption against pressure", and refers to a fluid retention capacity of water-absorbing resin under pressure. Specifically, "AAP" refers to a fluid retention capacity (unit: g/g) measured after 0.9 g of water-absorbing resin has been swollen in a large excess of a 0.9 weight % aqueous sodium chloride solution for 1 hour under a load of 2.06 kPa (21 g/cm$^2$, 0.3 psi). ERT 442.2-02 uses the term "Absorption Under Pressure", which refers to substantially the same thing as "AAP".

In the present invention, the load used during measurements has been changed to 4.83 kPa (49 g/cm$^2$, 0.7 psi). Although the term "AAP" is used in the present specification, all AAP measurements herein are fluid retention capacity measurements carried out under a load of 4.83 kPa.

[1-3-3] PSD (ERT 420.2-02)

The term "PSD" is an acronym for "particle size distribution", and refers to a particle size distribution of water-absorbing resin which is measured by sieve classification. The weight average particle diameter (D50) and the logarithmic standard deviation ($\sigma\zeta$) of a particle size distribution are measured in accordance with the method described in U.S. Pat. No. 7,638,570. In the present specification, unless otherwise specified, for convenience, "PSD" is used to refer the following: weight average particle diameter (D50); logarithmic standard deviation ($\sigma\zeta$) of particle size distribution; proportion of particles whose particle diameter is 600 μm or more and less than 850 μm (or less than 710 μm); and proportion of particles whose particle size is 150 μm or more and less than 850 μm (or less than 710 μm). Note that the value of weight average particle diameter (D50) changes depending on the configuration of the sieve used. As such, there is a need for adequate caution regarding the configuration of the sieve used.

[1-3-4] Ext (ERT 470.2-02)

The term "Ext" is an abbreviation for "Extractables", and refers to a water-soluble component (water-soluble component amount) of water-absorbing resin. Specifically, the Ext refers to the amount (unit: weight %) of a polymer dissolved in an aqueous solution after adding 1.0 g of water-absorbing resin to 200 ml of a 0.9 weight % aqueous sodium chloride solution and stirring the resulting mixture at 500 rpm for 16 hours. The dissolved polymer amount is measured by pH titration.

[1-3-4] Moisture Content (ERT 430.2-02)

The term "moisture content" denotes a moisture content of a water-absorbing resin. Specifically, the "moisture content" is a value (unit: weight %) calculated from a drying loss resulting from drying 4.0 g of a water-absorbing resin at 105° C. for 3 hours.

For the present invention, for measurements of the moisture content of water-absorbing resin, the amount of water-absorbing resin was changed to 1.0 g, and the drying temperature was changed to 180° C.

[1-4] Liquid Permeability

The term "liquid permeability" as used with respect to a water-absorbing resin of an embodiment of the present invention denotes flowability of liquid between swollen gel particles under load or without load. Typical methods of measuring the "liquid permeability" include saline flow conductivity (SFC) and gel bed permeability (GBP).

The "SFC" refers to a liquid permeability of a water-absorbing resin under a load of 2.07 kPa with respect to a 0.69 weight % aqueous sodium chloride solution, and is a value measured in accordance with the SFC testing method disclosed in U.S. Pat. No. 5,669,894.

The "GBP" refers to a liquid permeability of a water-absorbing resin with respect to a 0.69 weight % aqueous sodium chloride solution under load or in freely swellable conditions, and is a value measured in accordance with the GBP testing method disclosed in International Publication No. WO 2005/016393.

[1-5] Specific Surface Area

The term "specific surface area" as used with respect to the present invention refers to a surface area per unit weight of a water-absorbing resin (unit: $m^2/kg$). Typical examples of methods for measuring the specific surface area include a gas adsorption (BET) method, and a method in which the specific surface area is determined by using 3-D analysis software to perform image analysis on the results of measurement from a 3-D analysis apparatus using x-rays. The gas adsorption (BET) method is carried out in accordance with JIS Z 8830.

[1-6] Other

In the present specification, any range of "X to Y" denotes "X or more and Y or less". The unit of weight "t (ton)" denotes "metric ton". In addition, unless otherwise noted, the unit "ppm" denotes "ppm by weight". Furthermore, unless otherwise noted, the terms "weight" and "mass" are used synonymously, the terms "weight %" and "mass %" are used synonymously, and the terms "parts by weight" and "parts by mass" are used synonymously. Further, " . . . acid (salt)" means " . . . acid and/or salt thereof", and "(meth) acrylic" means "acrylic and/or methacrylic".

[2] Method for Producing Water-Absorbing Agent

A method for producing a water-absorbing agent in accordance with an embodiment of the present invention is a method for producing a water-absorbing agent containing a polyacrylic acid (salt)-based water-absorbing resin as a main component, including the steps of:

(A) polymerizing an aqueous monomer solution so that a crosslinked hydrogel polymer is obtained, the aqueous monomer solution containing a monomer and at least one polymerizable internal crosslinking agent, the monomer containing acrylic acid (salt) as a main component;

(B) gel-crushing the crosslinked hydrogel polymer such that the crosslinked hydrogel polymer has a weight average particle diameter (D50) of 500 μm or more and less than 1500 μm, and then drying the crosslinked hydrogel polymer so that a dried polymer is obtained;

(C) pulverizing the dried polymer and then classifying the dried polymer so that a water-absorbing resin powder is obtained; and (D) surface-crosslinking the water-absorbing resin powder with use of at least one surface-crosslinking agent so that water-absorbing resin particles are obtained, the water-absorbing resin powder obtained through the steps (A) to (C) satisfying the following physical properties (1) to (4):

(1) a CRC is 35 g/g or more;

(2) a weight average particle diameter (D50) is 300 μm or more and less than 400 μm;

(3) a logarithmic standard deviation (σζ) of a particle size distribution is 0.30 or more and less than 0.40; and (4) an average gap radius is 100 μm or more and less than 300 μm.

The following description will discuss in detail a method for producing a water-absorbing agent in accordance with an embodiment of the present invention.

[2-1] Step of Preparing Aqueous Monomer Solution (Step Performed Prior to Step (A))

This step is a step of preparing an aqueous monomer solution containing a monomer and at least one polymerizable internal crosslinking agent, the monomer containing acrylic acid (salt) as a main component. Note that the term "main component" means that the acrylic acid (salt) is used (contained) ordinarily in an amount of not less than 50 mol %, preferably of not less than 70 mol %, and more preferably of not less than 90 mol % (an upper limit being 100 mol %) relative to a total amount of monomers to be used for a polymerization reaction (excluding an internal crosslinking agent). It is also possible to use a monomer slurry liquid to an extent that water absorption performance of a water-absorbing agent to be obtained as an end product is not affected. For convenience, however, the present specification will describe an aqueous monomer solution.

(Acrylic Acid (Salt))

In an embodiment of the present invention, a known acrylic acid (salt) is preferably used as the monomer (also referred to as a polymerizable monomer), from the viewpoint of the physical properties of the water-absorbing agent and from the viewpoint of productivity. Known acrylic acids contain, in trace amounts, components such as a polymerization inhibitor, an impurity, and/or the like. The polymerization inhibitor is preferably a methoxyphenol, more preferably a p-methoxyphenol. The polymerization inhibitor is contained in the acrylic acid in an amount (at a concentration) that is preferably not more than 200 ppm, more preferably within a range of 10 ppm to 160 ppm, even more preferably within a range of 20 ppm to 100 ppm, from the viewpoint of, for example, polymerizability of the acrylic acid and the color of a water-absorbing agent to be produced. Examples of the impurity which may be included in acrylic acid used in an embodiment of the present invention include an organic compound such as acetic acid, propionic acid, and furfural, and the various compounds disclosed in U.S. Patent Application Publication No. 2008/0161512.

Examples of acrylic acid salt include a salt obtained by neutralizing the above-described acrylic acid with use of a basic compound described below. Examples of the acrylic acid salt encompass a commercially available acrylic acid salt (for example, sodium acrylate) and a salt obtained by neutralizing an acrylic acid.

(Basic Compound)

The term "basic compound" as used with respect to the present invention refers to a compound that exhibits basicity. Specific examples include sodium hydroxide. Note that commercially available sodium hydroxide contains a heavy metal such as zinc, lead, and/or iron on the order of ppm, and may thus be technically referred to as a "composition". In an embodiment of the present invention, such compositions are treated as being encompassed in the scope of "basic compounds".

Specific examples of the basic compound include a carbonate or bicarbonate of an alkali metal, a hydroxide of an alkali metal, ammonia, and organic amine. Out of such examples, from the viewpoint of water absorption performance of the water-absorbing agent, a strongly basic compound is selected. As such, the basic compound is preferably a hydroxide of an alkali metal such as sodium, potassium, or lithium. The basic compound is more preferably sodium hydroxide. From the viewpoint of handleability, the basic compound is preferably in the form of an aqueous solution.

(Neutralization)

In a case where a salt obtained by neutralizing acrylic acid is to be used as the acrylic acid salt, the timing of the neutralization of the acrylic acid is not limited. The neutralization can be carried out before, during, or after polymerization. The neutralization may be carried out at a plurality of times or locations. From the viewpoint of efficiency of producing the water-absorbing agent, continuous type neutralization is preferable.

In a case where acrylic acid (salt) is to be used in an embodiment of the present invention, the neutralization rate of the acrylic acid (salt) is preferably 10 mol % to 90 mol %, more preferably 40 mol % to 85 mol %, even more preferably 50 mol % to 80 mol %, and particularly preferably 60 mol % to 75 mol %, relative to the acid groups of the monomer. Setting the neutralization rate to be within the above range makes it possible to prevent a decrease in the water absorption performance of the water-absorbing agent.

The above range of the neutralization rate is applied to neutralization carried out before the polymerization, neutralization carried out during the polymerization, and neutralization carried out after the polymerization. The above ranges are applied similarly to a water-absorbing agent as an end product. With regard to neutralization conditions such as a neutralization apparatus, a neutralization temperature, and a retention time, the conditions disclosed in International Publication No. 2009/123197 may be applied to an embodiment of the present invention.

(Other Monomer(s))

In an embodiment of the present invention, a monomer other than the acrylic acid (salt) can, as necessary, be used in combination with the acrylic acid (salt) (hereinafter, a monomer(s) other than the acrylic acid (salt) is referred to as "other monomer(s)").

Specific examples of the other monomer(s) include monomers (excluding acrylic acid (salt)) disclosed in U.S. Patent Application Publication No. 2005/0215734. Examples of the other monomer(s) include a water-soluble unsaturated monomer and a hydrophobic unsaturated monomer. In a case where the other monomer(s) is to be used, the amount of the other monomer(s) used is preferably 30 mol % or less, more preferably 10 mol % or less, and even more preferably 5 mol % or less, relative to the total amount of monomers (excluding an internal crosslinking agent).

(Internal Crosslinking Agent)

In an embodiment of the present invention, an internal crosslinking agent is used. Specific examples of the internal crosslinking agent include the internal crosslinking agents disclosed in U.S. Pat. No. 6,241,928. At least one internal crosslinking agent is selected from among these internal crosslinking agents, with consideration given to reactivity and the like. From the viewpoint of water absorption performance and the like of the water-absorbing agent, the internal crosslinking agent is preferably an internal crosslinking agent having two or more polymerizable unsaturated groups, more preferably an internal crosslinking agent which is pyrolytic at a later described drying temperature, and even more preferably an internal crosslinking agent having a (poly)alkylene glycol structure and two or more polymerizable unsaturated groups.

Specific examples of the polymerizable unsaturated groups include an allyl group and a (meth)acrylate group. Specific examples of the (poly)alkylene glycol structure include polyethylene glycol. The n number of the (poly)alkylene glycol structure is in a range of preferably 1 to 100, and more preferably 6 to 50.

As such, the internal crosslinking agent which is used in an embodiment of the present invention is preferably (poly)alkylene glycol di(meth)acrylate or (poly)alkylene glycol tri(meth)acrylate, and more preferably (poly)ethylene glycol di(meth)acrylate.

An amount of the internal crosslinking agent used is preferably 0.0001 mol % to 10 mol %, more preferably 0.001 mol % to 5 mol %, and even more preferably 0.01 mol % to 1 mol %, relative to the total amount of monomers (excluding an internal crosslinking agent). Setting the amount of internal crosslinking agent used so as to be within the above ranges makes it possible to obtain a water-absorbing agent having a desired water absorption performance. In a case where the amount of internal crosslinking agent used does not fall within the above ranges, there may be a reduction in gel strength accompanied by an increase in water-soluble component and a reduction in fluid retention capacity.

The internal crosslinking agent is preferably added beforehand, during the preparation of the aqueous monomer solution. In such a case, a crosslinking reaction takes place simultaneously with the polymerization reaction. Note, however, that it is possible to start the polymerization reaction without adding the internal crosslinking agent and then carry out the crosslinking reaction thereafter by adding the internal crosslinking agent during or after the polymerization reaction. Alternatively, a combination of these techniques may be employed.

(Substance(s) Added to Aqueous Monomer Solution)

In an embodiment of the present invention, from the viewpoint of improving physical properties of the water-absorbing agent, any of the below substances can be added to the aqueous monomer solution at at least one of the following times: during preparation of the aqueous monomer solution, during the polymerization reaction; during the crosslinking reaction; after the polymerization reaction; and after the crosslinking reaction.

Specific examples of the substance which can be added include: a hydrophilic polymer such as starch, a starch derivative, cellulose, a cellulose derivative, polyvinyl alcohol (PVA), polyacrylic acid (salt), and crosslinked polyacrylic acid (salt); and a compound such as a carbonate, an azo compound, a foaming agent which generates any of various types of gas bubbles, a surfactant, a chelating agent, and a chain transfer agent. Examples of a chain transfer agent that can be used include the chain transfer agents disclosed in Patent Literatures 5 and 21.

The amount of the hydrophilic polymer added is preferably 50 weight % or less, more preferably 20 weight % or less, even more preferably 10 weight % or less, and particularly preferably 5 weight % or less (with a lower limit of 0 weight %), relative to the aqueous monomer solution. The amount of the compound added is preferably 5 weight % or less, more preferably 1 weight % or less, and even more preferably 0.5 weight % or less (with a lower limit of 0 weight %), relative to the aqueous monomer solution.

In a case where a water-soluble resin or a water-absorbing resin is used as the hydrophilic polymer, a graft polymer or a water-absorbing resin composition (for example, a copolymer produced from starch and acrylic acid (salt), or a copolymer produced from PVA and acrylic acid (salt)) can be obtained. These graft polymers and water-absorbing resin compositions are also encompassed in the scope of the polyacrylic acid (salt)-based water-absorbing resin of an embodiment of present invention.

(Monomer Component Concentration)

The aqueous monomer solution is prepared by selecting various substances (components) as described above in accordance with an objective and then mixing the selected components together in respective amounts defined so as to fall within the above-described ranges. Note that, in an embodiment of the present invention, instead of employing an aqueous monomer solution, it is possible to employ a mixed monomer solution containing water and a hydrophilic solvent.

From the viewpoint of the physical properties of the water-absorbing agent, the concentration of the total of the various substances (components) (this total hereinafter referred to as a "monomer component") is in a range of preferably 10 weight % to 80 weight %, more preferably 20 weight % to 75 weight %, and even more preferably 30 weight % to 70 weight %. The concentration of the monomer component is calculated by use of Formula (1) below.

Concentration of monomer component (weight %)= (weight of monomer component/weight of aqueous monomer solution)×100          Formula (1)

Note that in Formula (1), the weight of the aqueous monomer solution does not include a weight of a graft component, a weight of the water-absorbing resin, or a weight of a hydrophobic organic solvent used in reversed phase suspension polymerization.

[2-2] Polymerization Step (Step (A))

This step is a step of polymerizing the aqueous monomer solution obtained in the step of preparing the aqueous monomer solution so that a crosslinked hydrogel polymer (hereinafter referred to as "hydrogel") is obtained, the aqueous monomer solution containing a monomer and at least one polymerizable internal crosslinking agent, the monomer containing acrylic acid (salt) as a main component. Note that this polymerization step is "Step (A)" as defined in this specification.

(Polymerization Initiator)

In an embodiment of the present invention, a polymerization initiator is used at the time of polymerization. Examples of the polymerization initiator include a pyrolysis-type polymerization initiator, a photolytic-type polymerization initiator, and a redox-type polymerization initiator that contains a reducing agent for facilitating decomposition of these polymerization initiators. Specific examples of the polymerization initiator include the polymerization initiators disclosed in U.S. Pat. No. 7,265,190. At least one polymerization initiator is selected from among these polymerization initiators, with consideration given to the form of polymerization and the like. From the viewpoint of, for example, handleability of the polymerization initiator and the physical properties of the water-absorbing agent, the polymerization initiator is preferably a peroxide or an azo compound, more preferably a peroxide, and even more preferably a persulfate.

An amount of the polymerization initiator used is preferably 0.001 mol % to 1 mol %, more preferably 0.001 mol % to 0.5 mol %, and even more preferably 0.01 mol % to 0.1 mol %, relative to the total amount of monomers (excluding an internal crosslinking agent). An amount of the reducing agent used is preferably 0.0001 mol % to 0.02 mol %, and more preferably 0.0005 mol % to 0.015 mol %, relative to the total amount of monomers (excluding an internal crosslinking agent). Setting the amounts of polymerization initiator and reducing agent used so as to be within the above ranges makes it possible to obtain a water-absorbing agent having a desired water absorption performance.

In an embodiment of the present invention, the polymerization reaction may be initiated by irradiation of an active energy ray such as a radiation ray, an electron ray, and/or an ultraviolet ray. It is also possible to combine irradiation of an active energy ray with the above-described polymerization initiator.

(Form of Polymerization)

Examples of forms of polymerization which can be applied to an embodiment of the present invention include aqueous solution polymerization, reversed phase suspension polymerization, spray polymerization, droplet polymerization, bulk polymerization, and precipitation polymerization. Out of these forms, from the viewpoints of ease of controlling polymerization and the water absorption performance of the water-absorbing agent, the form of polymerization is preferably aqueous solution polymerization or reversed phase suspension polymerization, more preferably aqueous solution polymerization, and even more preferably continuous aqueous solution polymerization. The continuous aqueous solution polymerization makes it possible to produce the water-absorbing agent with high productivity. Specific examples of the continuous aqueous solution polymerization include continuous belt polymerization as disclosed in U.S. Pat. No. 4,893,999 and the like, and continuous kneader polymerization as disclosed in U.S. Pat. No. 6,987,151 and the like. Examples of the reversed phase suspension polymerization are disclosed in, for example, Patent Literatures 2, 4, and 21.

Examples of preferable forms of the continuous aqueous solution polymerization include high-temperature-initiating polymerization, high-concentration polymerization, and foaming polymerization. The high-temperature-initiating polymerization is a form of polymerization in which a temperature of the aqueous monomer solution at the initiation of polymerization is preferably 30° C. or more, more preferably 35° C. or more, even more preferably 40° C. or more, and particularly preferably 50° C. or more (the upper limit being the boiling point of the aqueous monomer solution). The high-concentration polymerization is a form of polymerization in which a monomer concentration at the initiation of polymerization is preferably 30 weight % or more, more preferably 35 weight % or more, even more preferably 40 weight % or more, and particularly preferably 45 weight % or more (the upper limit being a saturation concentration of the aqueous monomer solution). The foaming polymerization is a form of polymerization in which the aqueous monomer solution to be polymerized contains a foaming agent or gas bubbles. One of these forms of polymerization may be employed alone. Alternatively, two or more of these forms of polymerization may be employed in combination.

Examples of a method for dispersing gas bubbles in the foaming polymerization include: a method of dispersing gas bubbles by reducing the solubility of gas dissolved in the aqueous monomer solution; a method of introducing gas from an external source and dispersing the gas as gas bubbles; and a method of causing foaming by adding a foaming agent to the aqueous monomer solution. A combination of any of these methods for dispersing gas bubbles may be employed as appropriate in accordance with desired physical properties of the water-absorbing agent.

With regards to a case where a gas is introduced from outside the aqueous monomer solution, specific examples of the gas include oxygen, air, nitrogen, carbonic acid gas, ozone, and the like, as well as a mixed gas constituted by a mixture of any of these gases. Preferably used is an inert gas(es) such as nitrogen and carbonic acid gas. From the viewpoints of polymerizability and cost, more preferably used is nitrogen.

In a case where the aqueous monomer solution is caused to foam, examples of the foaming agent include an azo compound and a solution, dispersion liquid, or powder (for example, a powder having particle diameter of 0.1 μm to 1000 μm) of an organic or inorganic carbonate. Out of these examples, the inorganic carbonate is preferable. Specific examples include a carbonate such as sodium carbonate, ammonium carbonate, and magnesium carbonate, and a bicarbonate.

In a case where the foaming polymerization is employed, a hydrogel and a water-absorbing resin, each constituted by foamed particles, is produced in the process of producing the water-absorbing agent. The water-absorbing agent constituted by foamed particles is porous. This increases the surface area of the water-absorbing agent and thus improves water absorption speed. This also makes it easy to fix the water-absorbing agent in an absorbent body of an absorbent article. Whether or not the particles are foamed particles can be confirmed by observing the pores of the surface of a particle by use of an electron microscope. The number of pores per water-absorbing agent particle is preferably 1 or more, more preferably 1 to 10,000, and even more preferably 10 to 1,000.

The above-described forms of polymerization may be carried out under an air atmosphere. From the viewpoint of the color of the water-absorbing agent, the forms of polymerization are preferably carried out under an inert gas atmosphere such as nitrogen or argon (an atmosphere in which oxygen concentration is not more than 1 volume %). Note that oxygen dissolved in the aqueous monomer solution is also preferably sufficiently substituted with inert gas (such that a dissolved oxygen amount is less than 1 mg/L).

[2-3] Gel-Crushing Step (Part of Step (B))

This step is a step of gel-crushing the hydrogel, prepared through the polymerization step, so that a hydrogel in the form of particles (hereinafter referred to as "particulate hydrogel") is obtained. This step is called "gel-crushing" to distinguish it from the "pulverization" of the later-described pulverizing step. This gel-crushing step is a part of "Step (B)" as defined in this specification.

The gel-crushing refers to adjusting the size of the hydrogel so as to be a predetermined size, with use of a gel crusher such as a kneader, a meat chopper, or a cutter mill. With regards to the form of the gel-crushing and the operating conditions employed in the gel-crushing, the disclosures of, for example, International Publication No. 2011/126079 (Patent Literature 3) and International Publication No. 2016/204302 (Patent Literature 23) can be applied to an embodiment of the present invention. Note that in a case where the form of polymerization is kneader polymerization, the polymerization step and the gel-crushing step are carried out simultaneously. In a case where reversed phase suspension polymerization, spray polymerization, droplet polymerization, or the like is employed and a particulate hydrogel is obtained during the polymerization step, it is considered that the gel-crushing step has been carried out simultaneously with the polymerization step.

In an embodiment of the present invention, in a case where the gel-crushing is carried out with use of a screw extrusion type gel crusher such as a meat chopper, adjusting the rotation speed of the gel crusher makes it possible to easily control the particle diameter of the particulate hydrogel. Rotation speed in such a case is preferably 120 rpm or more, more preferably 140 rpm or more, and even more preferably 150 rpm or more. In a case where the rotation speed is less than 120 rpm, the hydrogel will not be adequately crushed. This can cause problems such as: a decreased absorption speed of, for example, body fluids such as urine and blood when the hydrogel is used as a water-absorbing agent; and the water-absorbing agent having an average gap radius which does not fall within a range in accordance with an embodiment of the present invention.

(Particle Size of Particulate Hydrogel)

In an embodiment of the present invention, the particle size of the particulate hydrogel may be controlled by classification, blending, or the like, but is preferably controlled by foaming polymerization, gel-crushing, or the like.

As to the particle size of the particulate hydrogel, the particulate hydrogel has a weight average particle diameter (D50) of preferably 500 μm to 1,500 μm, more preferably 550 μm to 1,200 μm, and even more preferably 600 μm to 1,000 μm.

In a case where the weight average particle diameter (D50) of the particulate hydrogel exceeds 1,500 μm, the shearing and compressive forces applied to the particulate hydrogel may be uneven and insufficient. Furthermore, with a weight average particle diameter (D50) exceeding 1,500 μm, because the speed with which drying progresses differs between the surface and the inside of the particulate hydrogel, pulverization performed after drying may generate particles having uneven physical properties and thus cause a deterioration in the physical properties of the water-absorbing agent as a whole.

In a case where the weight average particle diameter (D50) of the particulate hydrogel is less than 500 μm, the surface area per unit weight of the particulate hydrogel increases, and thus the particulate hydrogel becomes susceptible to extreme drying. This can cause the reduction of residual monomers during the drying step to be insufficient and as a result can cause an increase in residual monomers in the water-absorbing agent. Furthermore, with a weight average particle diameter (D50) of less than 500 μm, a large amount of fine powder will be generated by the pulverization after drying. This can make it difficult to control the particle size and thus cause a deterioration in physical properties (such as liquid permeability) of the water-absorbing agent.

As to the particle size of the particulate hydrogel, a logarithmic standard deviation (σζ) of a particle size distribution of the particulate hydrogel is preferably 0.2 to 1.5, more preferably 0.2 to 1.3, and even more preferably 0.2 to 1.2. A smaller value of the logarithmic standard deviation (σζ) of the particle size distribution correlates to a more uniform particle diameter and offers the advantage of enabling uniform drying. However, a logarithmic standard deviation (σζ) of a particle size distribution which is less than 0.2 requires a special operation such as particle size control during polymerization before the gel-crushing or classification of the particulate hydrogel after gel-crushing. As such, a logarithmic standard deviation (σζ) of particle size distribution which is less than 0.2 is substantially difficult to employ from the viewpoint of productivity and cost.

[2-4] Drying Step (Part of Step (B))

This step is a step of drying the particulate hydrogel obtained through the polymerization step and/or the gel-crushing step until the particulate hydrogel has a resin solid content in a desired range, so that a dried polymer is obtained. This drying step is a part of "Step (B)" as defined in this specification.

The resin solid content is calculated from drying loss (a change in weight after drying 1 g of a sample at 180° C. for three hours). The resin solid content is preferably 80 weight % or more, more preferably 85 weight % to 99 weight %, even more preferably 90 weight % to 98 weight %, and particularly preferably 92 weight % to 97 weight %.

Examples of forms of drying employed in an embodiment of the present invention include thermal drying, hot air drying, drying under reduced pressure, fluidized bed drying, infrared drying, microwave drying, drum dryer drying, drying by azeotropic dehydration with a hydrophobic organic solvent, and high humidity drying by use of high temperature water vapor. Out of these examples, from the viewpoint of drying efficiency, hot air drying is preferable, and hot air drying which uses a continuous-type through-flow belt is more preferable.

In an embodiment of the present invention, a drying temperature is preferably 120° C. to 250° C., more preferably 130° C. to 230° C., and even more preferably 150° C. to 200° C., from the viewpoints of drying efficiency and the color of the water-absorbing agent. Furthermore, a drying time is preferably 10 minutes to 2 hours, more preferably 20 minutes to 1.5 hours, and even more preferably 30 minutes to 1 hour. Setting the drying temperature and the drying time to be within these ranges makes it possible to obtain a water-absorbing agent whose physical properties are within a desired range. Such a drying temperature and drying time also make it possible for the physical properties of the water-absorbing resin powder and water-absorbing resin particle, which are intermediate products, to be within a desired range.

The drying temperature is normally defined by the temperature of the heat medium (for example, in the case of hot air drying, the temperature of the hot air). However, in the case of drying in which the drying temperature cannot be defined by the temperature of the heat medium, as in the case of, for example, microwave drying, the drying temperature is defined by the temperature of the particulate hydrogel. The drying temperature may be constant or may be changed as appropriate during the drying.

Drying conditions other than the drying temperature and the drying time can be set as appropriate in accordance with, for example, moisture content of the particulate hydrogel, an amount of the particulate hydrogel supplied during the drying step, and the desired resin solid content. In a case where hot air drying which uses a continuous-type through-flow belt is employed, the drying conditions disclosed in, for example, International Publication No. 2006/100300 can be applied to an embodiment of the present invention.

[2-5] Pulverizing Step and Classification Step (Step (C))

This step is a step of pulverizing the dried polymer obtained through the drying step (pulverizing step) and adjusting the particle size of the pulverized polymer to a particle size within a desired range (classification step) so as to obtain a water-absorbing resin powder (a water-absorbing resin which has not been subjected to surface crosslinking). The pulverizing step makes it possible to obtain water-absorbing resin powder whose particles have a non-uniformly pulverized particle shape. Note that this step of pulverizing and classification is "Step (C)" as defined in this specification.

Examples of a pulverizer which can be used in the pulverizing step include: a high-speed rotation pulverizer such as a roll mill, a hammer mill, a screw mill, or a pin mill; a vibration mill; a knuckle-type pulverizer; and a cylindrical mixer. Out of these examples, a roll mill is preferable from the viewpoint of efficiency of pulverization. It is also possible to employ a combination of a plurality of these pulverizers.

Examples of methods for adjusting the particle size in the classification step include sieve classification with use of a JIS standard sieve (JIS Z 8801-1 ((2000)), airflow classification, and the like. Out of these examples, sieve classification is preferable from the viewpoint of classification efficiency. Adjusting the particle size of the water-absorbing agent is not limited to being carried out in the pulverizing step or classification step. The adjusting can be carried out in, for example, the polymerization step (particularly in reversed phase suspension polymerization, droplet polymerization, or the like) or some other step (for example, a granulation step or a fine powder recovery step). In a case where the particle size is not within the desired range, the average gap radius may not fall within a range in accordance with an embodiment of the present invention.

(Physical Properties of Water-Absorbing Resin Powder)

In the method for producing the water-absorbing agent in accordance with an embodiment of the present invention, the water-absorbing resin powder obtained through the above-described steps must satisfy the following physical properties (1) to (4).

(1) a CRC is 35 g/g or more;
(2) a weight average particle diameter (D50) is 300 μm or more and less than 400 μm;
(3) a logarithmic standard deviation (σζ) of a particle size distribution is 0.30 or more and less than 0.40; and
(4) an average gap radius is 100 μm or more and less than 300 μm.

The physical properties (1) to (4) are preferably controlled so as to each be within a range described below. The physical properties satisfying the below ranges makes it possible to obtained a water-absorbing agent in accordance with an embodiment of the present invention. The following description will discuss preferable ranges of the physical properties (1) to (4).

(1) CRC

In order to obtain the water-absorbing agent in accordance with an embodiment of the present invention, the water-absorbing resin powder of an embodiment of the present invention has a CRC which is necessarily 35 g/g or more, preferably 35.5 g/g or more, and more preferably 36 g/g or more. From the viewpoint of balance with other physical properties, the upper limit of the CRC is preferably 45 g/g or less, more preferably 42 g/g or less, and even more preferably 40 g/g or less. The CRC can be controlled by, for example, an amount of the internal crosslinking agent during polymerization, the monomer concentration, and the drying temperature.

(2) Weight Average Particle Diameter (D50)

In order to obtain the water-absorbing agent in accordance with an embodiment of the present invention, the water-absorbing resin powder of an embodiment of the present invention has a weight average particle diameter (D50) which is necessarily 300 μm or more and less than 400 μm, preferably 310 μm or more and less than 390 μm, more preferably 320 μm or more and less than 390 μm, even more preferably 320 μm or more and less than 380 μm, and particularly preferably 340 μm or more and less than 380 μm. The weight average particle diameter (D50) can be controlled by, for example, the particle diameter of the hydrogel, pulverization after drying, and classification after drying.

(3) Logarithmic Standard Deviation (σζ) of Particle Size Distribution

The water-absorbing resin powder of an embodiment of the present invention has a logarithmic standard deviation (σζ) of a particle size distribution which is necessarily 0.30 or more and less than 0.40, preferably 0.32 or more and less than 0.39, and more preferably 0.34 or more and less than 0.38.

(4) Average Gap Radius

In order to obtain the water-absorbing agent in accordance with an embodiment of the present invention, the water-absorbing resin powder of an embodiment of the present invention has an average gap radius which is necessarily 100 μm or more and less than 300 μm. The upper limit of the average gap radius is preferably less than 290 μm and more preferably less than 280 μm. The lower limit of the average gap radius is preferably 200 μm or more.

In a case where the average gap radius exceeds 300 μm, the average gap radius of the water-absorbing resin particle after surface crosslinking and the water-absorbing agent after surface crosslinking increases. This may cause the updraw fluid retention capacity under load, which is a characteristic of the water-absorbing agent in accordance with an embodiment of the present invention, to be reduced.

The average gap radius can be controlled by, for example: adjusting the hydrogel to have a predetermined particle diameter (particularly, 500 μm or more and less than 1500 μm) by use of gel-crushing (particularly, gel-crushing in which screw rotation speed is 120 rpm or more); and adjusting the physical properties (2) and (3), by the pulverization and classification after drying.

Particle size distribution (PSD), which includes the physical properties (2) and (3), is measured in accordance with the methods disclosed in ERT 420.2-02 and U.S. Pat. No. 7,638,570, as described above in [1-3-3].

In order to obtain the water-absorbing agent in accordance with an embodiment of the present invention, the following physical properties (5) and (6) are also preferably satisfied, in addition to the physical properties (1) to (4). The following description will discuss preferable ranges of the physical properties (5) and (6).

(5) Particle Size Distribution (PSD)

In order to obtain the water-absorbing agent in accordance with an embodiment of the present invention, the water-absorbing resin powder of an embodiment of the present invention has a particle size distribution in which the proportion of particles with a particle diameter of 150 μm or more and less than 850 μm (or less than 710 μm) is preferably 90 weight % or more, more preferably 95 weight % or more, even more preferably 97 weight % or more, and particularly preferably 98 weight % or more (with an upper limit of 100 weight %). The proportion of particles with a particle diameter of 600 μm or more and less than 850 μm (or less than 710 μm) is preferably less than 10 weight %, more preferably less than 9 weight %, even more preferably less than 8 weight %, and particularly preferably less than 7 weight %. Note that the upper and lower limits of the particle diameter in the particle size distribution are defined by a JIS standard sieve.

(6) Specific Surface Area

In order to obtain the water-absorbing agent in accordance with an embodiment of the present invention, the water-absorbing resin powder of an embodiment of the present invention has a specific surface area which is preferably 27 $m^2/kg$ or more, more preferably 28.5 $m^2/kg$ or more, and even more preferably 30 $m^2/kg$ or more. From the viewpoint of balance with other physical properties, the upper limit of the specific surface area is preferably 50 $m^2/kg$ or less, more preferably 45 $m^2/kg$ or less, and even more preferably 40 $m^2/kg$ or less. Note that the preferable range of the specific surface area is not limited to the water-absorbing resin powder. The water-absorbing agent in accordance with an embodiment of the present invention is also has a specific surface area which is preferably in the same range.

[2-6] Surface-Crosslinking Step (Step (D))

This step is a step of providing, in a surface layer of a water-absorbing resin powder obtained through the above described steps, a portion with a higher crosslinking density. The surface-crosslinking step includes, for example, a mixing step, a heat treatment step, and a cooling step. The surface-crosslinking step involves, for example, radical cross-linking at the surface of the water-absorbing resin powder, surface polymerization of the water-absorbing resin powder, and a crosslinking reaction with a surface-crosslinking agent at the surface of the water-absorbing resin powder, so as to produce a surface-crosslinked water-absorbing resin (hereinafter referred to as "water-absorbing resin particles"). Note that this surface-crosslinking step is "Step (D)" as defined in this specification.

[2-6-1] Mixing Step

This step is a step of mixing, in a mixing apparatus, a solution containing a surface-crosslinking agent (hereinafter referred to as a "surface-crosslinking agent solution") with the water-absorbing resin powder, so that a humidified mixture is obtained.

(Surface-Crosslinking Agent)

In an embodiment of the present invention, a surface-crosslinking agent is used at the time of surface crosslinking. Specific examples of the surface-crosslinking agent include the surface-crosslinking agents disclosed in U.S. Pat. No. 7,183,456. At least one surface-crosslinking agent is selected from among these surface-crosslinking agents, with consideration given to reactivity and the like. Furthermore, from the viewpoints of, for example, handleability of the surface-crosslinking agent and water absorption performance of the water-absorbing agent, preferably selected is a surface-crosslinking agent which: has two or more functional groups which react with a carboxyl group; and is an organic compound which forms covalent bonds.

Specific examples of the surface-crosslinking agent include a polyhydric alcohol compound, an epoxy compound, a polyamine compound, a haloepoxy compound, a condensed product of a polyamine compound and a haloepoxy compound, an oxazoline compound, an oxazolidinone compound, an alkylene carbonate compound, a polyvalent glycidyl compound, an oxetane compound, a vinyl ether compound, and a cyclic urea compound. In order to improve the updraw fluid retention capacity under load, which is a characteristic of the water-absorbing agent in accordance with an embodiment of the present invention, it is preferable that at least one of polyhydric alcohol and alkylene carbonate is used.

An amount of the surface-crosslinking agent used (or the total amount in a case where more than one surface-crosslinking agent is used) is preferably 0.01 parts by weight to 10 parts by weight, more preferably 0.01 parts by weight to 5 parts by weight, and even more preferably 0.01 parts by weight to 1 part by weight, relative to 100 parts by weight of the water-absorbing resin powder. Setting the amount of surface-crosslinking agent used to be within the above ranges makes it possible to form an optimal crosslinked structure in the surface layer of the water-absorbing resin powder and thus makes it possible to obtain a water-absorbing agent with excellent physical properties.

The surface-crosslinking agent is preferably added in the form of an aqueous solution to the water-absorbing resin powder. In such a case, an amount of water used is preferably 0.1 parts by weight to 20 parts by weight, more preferably 0.3 parts by weight to 15 parts by weight, and even more preferably 0.5 parts by weight to 10 parts by weight, relative to 100 parts by weight of the water-absorbing resin powder. Setting the amount of water used to be within the above ranges improves the handleability of the surface-crosslinking agent solution and makes it possible to uniformly mix the surface-crosslinking agent with the water-absorbing resin powder.

Alternatively, the surface-crosslinking agent solution may contain, as necessary, a hydrophilic organic solvent in combination with the water. In such a case, an amount of the hydrophilic organic solvent used is preferably 10 parts by weight or less, more preferably 5 parts by weight or less, and even more preferably 1 part by weight or less, relative to 100 parts by weight of the water-absorbing resin powder. Specific examples of the hydrophilic organic solvent include a lower alcohol such as methyl alcohol; a ketone such as acetone; an ether such as dioxane; an amide such as N,N-dimethylformamide; a sulfoxide such as dimethyl sulfoxide; and a polyhydric alcohol such as ethylene glycol.

Further, additives to be added in "[2-7] Step of adding additive (particularly a liquid permeability improving agent)" can be each added to the surface-crosslinking agent solution in an amount in a range of 5 parts by weight or less. Alternatively, the additives can be added in the mixing step, separately from the surface-crosslinking agent solution.

(Method for Mixing and Conditions of Mixing)

A method for mixing the water-absorbing resin powder with the surface-crosslinking agent solution can be a method in which a surface-crosslinking agent solution is prepared in advance, and the surface-crosslinking agent solution is mixed with the water-absorbing resin powder preferably by spraying or dropping the surface-crosslinking agent solution onto the water-absorbing resin powder, more preferably by spraying the surface-crosslinking agent solution onto the water-absorbing resin powder.

A mixing apparatus for carrying out the mixing preferably has torque necessary to evenly and reliably mix the water-absorbing resin powder with the surface-crosslinking agent. The mixing apparatus is preferably a high-speed stirring mixer and more preferably a high-speed stirring continuous mixer. The high-speed stirring mixer has a rotation speed which is preferably 100 rpm to 10000 rpm and more preferably 300 rpm to 2000 rpm.

The water-absorbing resin powder supplied in this step has a temperature which is preferably 35° C. to 80° C., more preferably 35° C. to 70° C., and even more preferably 35° C. to 60° C., from the viewpoints of mixability with the surface-crosslinking agent solution and aggregability of the humidified mixture. The mixing time is preferably 1 second to 1 hour and more preferably 5 seconds to 10 minutes.

[2-6-2] Heat Treatment Step

This step is a step of heating the humidified mixture, which has been obtained in the mixing step, so as to cause a crosslinking reaction on a surface of the water-absorbing resin powder.

(Method for Heat Treatment and Conditions of Heat Treatment)

The heat treatment of the humidified mixture may involve heating the humidified mixture in a still state or heating the humidified mixture in a fluid state with use of motive power such as that of stirring or the like. It is preferable to heat the humidified mixture while the humidified mixture is stirred because such a method makes it possible to heat the entirety of the humidified mixture uniformly.

From the above viewpoint, examples of a heat treatment apparatus for carrying out the heat treatment include a paddle dryer, a multi-fin processer, and a tower dryer.

A heating temperature in this step is preferably 150° C. to 250° C., more preferably 170° C. to 250° C., and even more preferably 180° C. to 230° C., from such viewpoints as type and amount of surface-crosslinking agent, and water absorption performance of the water-absorbing agent. A heating time is at least 5 minutes and preferably at least 7 minutes.

Controlling the heating temperature and the heating time to be within the above ranges is preferable because doing so improves the water absorption performance of the water-absorbing agent to be obtained.

[2-6-3] Cooling Step

This step is an optional step which is carried out after the heat treatment step if needed. This step involves force-cooling the water-absorbing resin from its high temperature after the heat treatment step to a predetermined temperature and causing the surface-crosslinking reaction to finish quickly.

(Method for Cooling and Conditions of Cooling)

The cooling of the water-absorbing resin may involve cooling the water-absorbing resin in a still state or cooling the water-absorbing resin in a fluid state with use of motive power such as that of stirring or the like. It is preferable to cool the water-absorbing resin while the water-absorbing resin is stirred because such a method makes it possible to cool the entirety of the water-absorbing resin uniformly.

From the above viewpoint, examples of a cooling apparatus for carrying out the cooling include a paddle dryer, a multi-fin processer, and a tower dryer. These cooling apparatuses can have similar specifications to the heat treatment apparatus used in the heat treatment step. This is because a heat treatment apparatus can be used as a cooling apparatus by changing a heating medium to a cooling medium.

In this step, a cooling temperature may be set as appropriate in accordance with, for example, the heating temperature in the heat treatment step and the water absorption performance of the water-absorbing agent. The cooling temperature is preferably 40° C. to 100° C., more preferably 40° C. to 90° C., and even more preferably 50° C. to 70° C.

[2-7] Step of Adding Additive (Particularly a Liquid Permeability Improving Agent) (Step (E))

This step is a step of adding an additive as described below (particularly a liquid permeability improving agent) to the water-absorbing resin powder to be subjected to the surface-crosslinking step and/or to the water-absorbing resin particles obtained through the surface-crosslinking step. In the present specification, the "liquid permeability improving agent" used as the additive refers to a compound which has a function of improving the liquid permeability of the water-absorbing resin (for example, improving the SFC and/or the GBP by 0.1% or more). Typical methods of measuring the "liquid permeability" are, for example, saline flow conductivity (SFC) and gel bed permeability (GBP).

This additive adding step is "Step (E)" as defined in this specification. Step (E) may be carried out before, simultaneously with, or after the surface-crosslinking step (Step (D)), but is preferably carried out after Step (D).

The additive used in an embodiment of the present invention is preferably at least one of compound selected from the group including a polyvalent metal salt, a cationic polymer, and inorganic fine particles. Two or more additives may be used in combination as necessary. Note that instead of using these additives in order to improve liquid permeability, it is possible to use these additives as, for example, an anti-caking agent for a case where moisture has been absorbed, an agent for controlling powder fluidity, or a binder for the water-absorbing agent.

The amount of the additive added is set as appropriate in accordance with the compound(s) chosen. Note that adding the additive in an amount less than a predetermined amount may prevent achieving the effect of improving liquid permeability of the water-absorbing agent. Furthermore, adding the additive in an amount greater than a predetermined amount may cause an increase in the average gap radius of the water-absorbing agent and deterioration of the updraw fluid retention capacity under load. As such, in order to control the average gap radius to be within a range in accordance with an embodiment of the present invention, in some cases it may be preferable not to add the additive.

(Polyvalent Metal Salt)

In a case where a polyvalent metal salt is used as the additive, a polyvalent metal cation of the polyvalent metal salt has a valence of preferably two or more, more preferably two to four, and even more preferably three or four. Examples of polyvalent metals which can be used include aluminum and zirconium. As such, examples of polyvalent metal salts which can be used in this step include aluminum lactate, zirconium lactate, aluminum sulfate, and zirconium sulfate. Out of these examples, from the viewpoint of the effect of improving SFC, the polyvalent metal salt is more preferably aluminum lactate or aluminum sulfate and even more preferably aluminum sulfate.

The polyvalent metal salt can be added in an amount such that a concentration of the metal cation of the polyvalent metal salt relative to 1 g of the water-absorbing resin powder is preferably less than $3.6 \times 10^{-5}$ mol, more preferably less than $1.4 \times 10^{-5}$ mol, and even more preferably less than $1.0 \times 10^{-5}$ mol, or the addition of the polyvalent metal salt can be omitted (the lower limit being 0 mol, which refers to a case where the addition of the polyvalent metal salt is omitted).

(Cationic Polymer)

In a case where the cationic polymer is to be used, examples of the cationic polymer include the substances disclosed in U.S. Pat. No. 7,098,284. Out of these examples, a vinyl amine polymer is more preferable from the viewpoint of the effect of improving SFC. The cationic polymer has a weight average molecular weight of preferably 5000 to 1000000.

The cationic polymer can be added in an amount such that an amount of the cationic polymer relative to 100 parts by weight of the water-absorbing resin powder is preferably less than 2.5 parts by weight, more preferably less than 2.0 parts by weight, and even more preferably less than 1.0 parts by weight, or the addition of the cationic polymer can be omitted (the lower limit being 0 parts by weight, which refers to a case where the addition of the cationic polymer is omitted).

(Inorganic Fine Particles)

In a case where inorganic fine particles are to be used as the additive, examples of the inorganic fine particles include the substances disclosed in U.S. Pat. No. 7,638,570. Out of these examples, silicon dioxide is preferable from the viewpoint of the effect of improving SFC.

In a case where the inorganic fine particles have a primary particle diameter of less than 20 nm, the inorganic fine particles can be added in an amount such that an amount of the inorganic fine particles relative to 100 parts by weight of the water-absorbing resin powder is preferably less than 1.2 parts by weight, more preferably less than 1.0 parts by weight, and even more preferably less than 0.5 parts by weight, or the addition of the inorganic fine particles can be omitted (the lower limit being 0 parts by weight, which refers to a case where the addition of the inorganic fine particles is omitted). In a case where the inorganic fine particles have a primary particle diameter of 20 nm or more, the inorganic fine particles can be added in an amount such that an amount of the inorganic fine particles relative to 100 parts by weight of the water-absorbing resin powder is preferably less than 2.0 parts by weight, more preferably less than 1.5 parts by weight, and even more preferably less than 1.0 parts by weight, or the addition of the inorganic fine particles can be omitted (the lower limit being 0 parts by weight, which refers to a case where the addition of the inorganic fine particles is omitted).

[2-8] Other Steps

In an embodiment of the present invention, it is possible to carry out as necessary a step other than the above-described steps, such as a granulation step, a sizing step, a fine powder removal step, a fine powder recovery step, a fine powder recycling step, a step of adding another additive, and an iron removal step. It is also possible to further carry out at least one step selected from, for example, a transportation step, a storing step, a packing step, and a reserving step.

Note that the "sizing step" encompasses, for example, a step of classifying and removing fine powder subsequent to the surface-crosslinking step and a step of carrying out classification and pulverization in a case where a water-absorbing resin is aggregated to have a size larger than an intended size. The "fine powder recycling step" encompasses a step in which fine powder is added to, for example, the hydrogel which is a raw material, during any of the steps for producing the water-absorbing resin, the fine powder being added as is or after being made into a large hydrogel in a granulation step.

The step of adding another additive refers to a step of adding another additive in order to impart any of various functions to the water-absorbing agent. Examples of the "another additive" include a chelating agent, an inorganic reducing agent, an organic reducing agent, a hydroxycarboxylic acid compound, a surfactant, a compound having a phosphorus atom, an oxidizer, an organic powder such as a metal soap, a deodorizing agent, an antibacterial agent, pulp, and thermoplastic fibers. These "another additives" can be mixed either simultaneously with or separately from the surface-crosslinking agent and/or the additive.

In an embodiment of the present invention, out of the above "another additives", it is preferable to add a chelating agent and, in particular, it is more preferable to add an amino polyvalent carboxylic acid or an amino polyvalent phosphoric acid. These chelating agents are can be added in an amount of 0.001 weight % to 1 weight % relative to the monomer or the water-absorbing agent.

A chelating agent which can be used in the water-absorbing agent in accordance with an embodiment of the present invention preferably has an excellent ion sequestering ability and/or chelating ability with respect to, for example, Fe and/or Cu. Specifically, the chelating agent is more preferably a chelating agent having a stability constant with respect to an Fe ion which is 10 or more and preferably 20 or more. The chelating agent is even more preferably an amino polyvalent carboxylic acid or a salt thereof, or an amino polyvalent phosphoric acid or a salt thereof. The chelating agent is particularly preferably an amino polyvalent carboxylic acid, or a salt thereof, having three or more carboxyl groups.

With regards to the amino polyvalent carboxylic acid salt, acid groups contained therein may be partially or completely neutralized. Specific examples of the amino polyvalent carboxylic acid include diethylenetriaminepentaacetic acid, triethylenetetraaminehexaacetic acid, cyclohexane-1,2-diaminetetraacetic acid, N-hydroxyethylethylenediaminetriacetic acid, ethyleneglycoldiethlyetherdiaminetetraacetic acid, ethylenediaminetetrapropione acetic acid, N-alkyl-N'-carboxymethyl aspartic acid, N-alkenyl-N'-carboxymethyl aspartic acid, as well as an alkali metal salt, alkali earth metal salt, ammonium salt, and amine salt of the above.

With regards to the amino polyvalent phosphoric acid salt, acid groups contained therein may be partially or completely neutralized. Specific examples of the polyvalent phosphoric acid include ethylenediamine-N,N'-di(methylene phosphinic acid), ethylenediaminetetra(methylene phosphinic acid), nitriloacetic acid-di(methylene phosphinic acid), nitrilodiacetic acid-(methylene phosphinic acid), nitriloacetic acid-β-proprionic acid-methylene phosphonate, nitrilotris(methylene phosphonate), cyclohexanediaminetetra(methylene phosphonate), ethylenediamine-N,N'-diacetic acid-N,N'-di(methylene phosphonate), ethylenediamine-N,N'-di(methylene phosphonate), ethylenediaminetetra(methylene phosphonate), polymethylenediaminetetra(methylene phosphonate), diethylenetriaminepenta(methylene phosphonate), 1-hydroxyethylidenediphosphonic acid, and a salt of any of the above.

One substance, or two or more substances selected from the above groups may be used as the chelating agent. Out of these substances, diethylenetriaminepentaacetic acid, triethylenetetraaminehexaacetic acid, N-hydroxyethylethylenediaminetriacetic acid, and a salt of any of these are most preferable because they have an excellent effect of inhibiting deterioration caused by human urine, as described later.

In an embodiment of the present invention, the chelating agent, and particularly the amino polyvalent carboxylic acid, is used in a small amount, normally 0.00001 parts by weight to 10 parts by weight, and preferably 0.0001 parts by weight to 1 part by weight, relative to 100 parts by weight of the water-absorbing resin which is the main component. In a case where the chelating agent is used in an amount exceeding 10 parts by weight, not only will such an amount fail to achieve an effect corresponding to the amount used and thus be uneconomical, but such an amount can cause problems such as a reduction in an absorption amount. Note also that in a case where there the amount used is less than 0.00001 parts by weight, there will not be an sufficient effect brought about by the addition.

[3] Physical Properties of Water-Absorbing Agent

The water-absorbing agent in accordance with an embodiment of the present invention contains a polyacrylic acid (salt)-based water-absorbing resin as a main component and satisfies all of the physical properties (a) to (e) below.

(a) a weight average particle diameter (D50) is 300 μm or more and less than 400 μm;

(b) a proportion of particles with a particle diameter of 600 μm or more and less than 850 μm is less than 10 weight %;

(c) an average gap radius is 100 μm or more and less than 180 μm;

(d) a CRC is 28 g/g or more and less than 34 g/g; and (e) an AAP is 24 g/g or more.

The physical properties (a) to (e) are preferably controlled so as to each be within a range described below. The physical properties satisfying the ranges described below makes it possible to produce the water-absorbing agent, containing a water-absorbing resin as a main component, which can be employed in a wide variety of absorbent articles, and makes it possible to adequately achieve the effect of an embodiment of the present invention. The water-absorbing agent in accordance with an embodiment of the present invention has an excellent ability to absorb and retain liquid and an excellent liquid suction power. As such, the water-absorbing agent exhibits sufficient performance when used in an absorbent article such as a disposable diaper.

The water-absorbing agent in accordance with an embodiment of the present invention preferably further satisfies the physical properties (f) to (j) and the physical property (l) below.

(f) a proportion of particles with a particle diameter of 150 μm or more and less than 850 μm is 90 weight % or more;

(g) an updraw fluid retention capacity under load with a 30 cm water column is 20 g/g or more;

(h) an updraw fluid retention capacity under load with a 20 cm water column is 25 g/g or more;

(i) particles are foamed particles and have a non-uniformly pulverized particle shape;

(j) an FSR is 0.20 g/g/sec or more; and (l) an amount of a degradable soluble component is 0.1 weight % to 30 weight %.

The following description will discuss preferable ranges of the physical properties (a) to (l).

(a) Weight Average Particle Diameter (D50)

The water-absorbing agent in accordance with an embodiment of the present invention has a weight average particle diameter (D50) which is necessarily 300 μm or more and less than 400 μm, preferably 310 μm or more and less than 390 μm, more preferably 320 μm or more and less than 390 μm, even more preferably 320 μm or more and less than 380 μm, and particularly preferably 340 μm or more and less than 380 μm.

The above ranges are preferable because in a case where the weight average particle diameter (D50) of the water-absorbing agent falls within the above ranges, absorbent articles such as disposable diapers and sanitary napkins which use the water-absorbing agent as an absorbent body will have improved feel, and furthermore, the absorbent articles will have excellent performance with regard to diffusion of an absorbed liquid such as urine throughout the entirety of the absorbent body.

(b) Proportion of Particles with a Particle Diameter of 600 μm or More and Less than 850 μm The water-absorbing agent in accordance with an embodiment of the present invention has a proportion of particles with a particle diameter of 600 μm or more and less than 850 μm which is necessarily less than 10 weight %, preferably less than 9 weight %, more preferably less than 8 weight %, and even more preferably less than 7 weight %.

In a case where the proportion of particles with a particle diameter of 600 μm or more and less than 850 μm is weight % or more, roughness of the particles of the water-absorbing agent will become noticeable, and using such a water-absorbing agent in an absorbent article such as a disposable diaper or sanitary napkin may worsen the feel, comfort, and/or the like of the absorbent article.

(c) Average Gap Radius

The water-absorbing agent in accordance with an embodiment of the present invention has an average gap radius which is necessarily 100 μm or more and less than 180 μm, preferably 100 μm or more and less than 170 μm, and more preferably 100 μm or more and less than 160 μm. Note that a lower limit of the average gap radius is preferably 110 μm or more, more preferably 120 μm or more, even more preferably 130 μm or more, and particularly preferably 140 μm or more. As such, a preferable range of the average gap radius can be selected appropriately from the above upper and lower limits.

In a case where the average gap radius is 180 μm or more, the updraw fluid retention capacity under load of the water-absorbing agent will decrease, and thus the water-absorbing agent may no longer be suitable for use as an absorbent body of absorbent articles such as disposable diapers and sanitary napkins. In a case where the average gap radius is less than 100 μm, liquid permeation will be hindered, water absorption speed will resultingly decrease, and liquid leakage may occur in absorbent articles such as disposable diapers and sanitary napkins using the water-absorbing agent.

(d) CRC

The water-absorbing agent in accordance with an embodiment of the present invention has a CRC which is necessarily 28 g/g or more and less than 34 g/g, preferably 28.5 g/g or more and less than 33.5 g/g, and more preferably 29 g/g or more and less than 33 g/g.

In a case where the CRC is less than 28 g/g, the updraw fluid retention capacity under load of the water-absorbing agent will decrease, and thus the water-absorbing agent may no longer be suitable for use as an absorbent body of absorbent articles such as disposable diapers and sanitary napkins. In a case where the CRC is 34 g/g or more, the fluid retention capacity under pressure (AAP 4.83 kPa) of the water-absorbing agent may decrease in some cases.

(e) AAP

The water-absorbing agent in accordance with an embodiment of the present invention has an AAP which is necessarily 24 g/g or more, preferably 24.5 g/g or more, and more preferably 25.0 g/g or more. The upper limit of the AAP is not particularly limited but is preferably 30 g/g or less and more preferably 28 g/g or less, from the viewpoint of balance with other physical properties.

Setting the fluid retention capacity under pressure to be within the above ranges reduces re-wet of a liquid in a case where pressure is applied to the absorbent body in an inclined state and thus renders the water-absorbing agent suitable for use as an absorbent body of absorbent articles such as disposable diapers and sanitary napkins.

(f) Proportion of Particles with Particle Diameter of 150 μm or More and Less than 850 μm (or Less than 710 μm)

The water-absorbing agent in accordance with an embodiment of the present invention has a proportion of particles with a particle diameter of 150 μm or more and less than 850 μm (or less than 710 μm) which is preferably 90 weight % or more, more preferably 95 weight % or more, and even more preferably 97 weight % or more.

The proportion of the particles with a particle diameter of 150 μm or more and less than 850 μm (or less than 710 μm) is preferably 90 weight % or more because such a proportion makes it easier to control the average gap radius as defined for an embodiment of the present invention, and such a proportion prevents problems caused by fine particles of the water-absorbing agent, such as a decline in performance and the occurrence of dust.

(g) Updraw Fluid Retention Capacity under Load with a 30 cm Water Column

The water-absorbing agent in accordance with an embodiment of the present invention has an updraw fluid retention capacity under load with a 30 cm water column which is preferably 20 g/g or more, more preferably 21 g/g or more, and even more preferably 22 g/g or more. The upper limit of the updraw fluid retention capacity under load with a 30 cm water column is preferably 30 g/g or less and more preferably 28 g/g or less, from the viewpoint of balance with other physical properties.

Setting the updraw fluid retention capacity under load with a 30 cm water column to be within the above ranges brings about an excellent effect with regard to the ability of the absorbent body to suck up liquid against the force of gravity even in a case where pressure is applied to the absorbent body. This renders the water-absorbing agent suitable for use as an absorbent body of absorbent articles such as disposable diapers and sanitary napkins.

(h) Updraw Fluid Retention Capacity under Load with a 20 cm Water Column

The water-absorbing agent in accordance with an embodiment of the present invention has an updraw fluid retention capacity under load with a 20 cm water column which is preferably 25.0 g/g or more, more preferably 25.5 g/g or more, and even more preferably 26.0 g/g or more. The upper limit of the updraw fluid retention capacity under load with a 20 cm water column is preferably 35 g/g or less and more preferably 30 g/g or less, from the viewpoint of balance with other physical properties.

Setting the updraw fluid retention capacity under load with a 20 cm water column to be within the above ranges brings about an excellent effect with regard to the ability of the absorbent body to suck up liquid against the force of gravity in a case where pressure is applied to the absorbent body. This renders the water-absorbing agent suitable for use as an absorbent body of absorbent articles such as disposable diapers and sanitary napkins.

(i) Particle Shape

Particles of the water-absorbing agent in accordance with an embodiment of the present invention are preferably foamed particles. The water-absorbing agent constituted by foamed particles is porous and has an increased surface area. This improves water absorption speed. This also makes it easy to fix the water-absorbing agent in an absorbent body of an absorbent article. Whether or not the particles are foamed particles can be confirmed by observing the pores of the surface of a particle by use of an electron microscope. The number of pores per water-absorbing agent particle is preferably 1 or more, more preferably 1 to 10,000, and even more preferably 10 to 1,000. Controlling production of the particles of the water-absorbing agent via the foaming polymerization makes it possible to cause the particles of the water-absorbing agent to be foamed particles.

The particles of the water-absorbing agent in accordance with an embodiment of the present invention have a non-uniformly pulverized particle shape. The water-absorbing agent whose particles have a non-uniformly pulverized particle shape makes it possible to improve the water absorption speed of the water-absorbing agent and makes it easy to fix the water-absorbing agent in an absorbent article. The non-uniformly pulverized particle shape can be confirmed via observation of, for example, a cross section of a pulverized particle, with use of an electron microscope. The shape of the particles of the water-absorbing agent can be controlled via, for example, the gel-crushing and the pulverization after drying so as to be the non-uniformly pulverized particle shape.

(j) FSR (Water Absorption Speed)

The water-absorbing agent in accordance with an embodiment of the present invention has an FSR (water absorption speed) which is preferably 0.20 g/g/sec or more, more preferably 0.25 g/g/sec or more, even more preferably 0.30 g/g/sec or more, and particularly preferably 0.35 g/g/sec or more. The FSR (water absorption speed) can be controlled by the particle size control and the foaming polymerization of an embodiment of the present invention. Note that the FSR (water absorption speed) is defined by the method disclosed in U.S. Pat. No. 7,638,570.

(k) Additive

The water-absorbing agent in accordance with an embodiment of the present invention may contain water, an additive (particularly a liquid permeability improving agent) as described in [2-7] above, and/or another additive as described in [2-8] above. These additives are contained in an amount that is set as appropriate. The amounts can be preferably selected from the ranges described in [2-7] and [2-8] above. Note that a lower limit of the amounts in which these additives are contained is 0 (meaning that the additive is absent or not added). The additives may be added as necessary in an amount greater than 0, within the above ranges.

The water-absorbing agent in accordance with an embodiment of the present invention preferably contains moisture, from the viewpoints of, for example, stability of the powder against impact and FSR (water absorption speed). As such, the water-absorbing agent has a moisture content of preferably 0.1 weight % to 20 weight % and more preferably 0.5 weight % to 10 weight %.

(1) Degradable Soluble Component

Degradable soluble component is an index for evaluating resistance of a water-absorbing agent against deterioration due to human urine. Human urine contains components which cause deterioration and decomposition of a polymer skeleton of the water-absorbing agent. A representative example of such components is L-ascorbic acid. It is known that in a case where a water-absorbing agent holds absorbed human urine for a long period of time, the polymer skeleton will be destroyed and there will be an increase in soluble components.

As such, the water-absorbing agent in accordance with an embodiment of the present invention has a degradable soluble component in an amount which is preferably 0.1 weight % to 30 weight %, more preferably 0.2 weight % to 25 weight %, even more preferably 0.3 weight % to 22 weight %, particularly preferably 0.4 weight % to 20 weight %, and most preferably 0.5 weight % to 18 weight %. In a case where the amount of the degradable soluble component exceeds the upper limit of the above ranges, during a long period of usage, a swelled gel will deteriorate with time and there will be an increase in the amount of the soluble component. In some cases the soluble component may be eluted from the absorbent body and inhibit diffusion of a liquid, such as blood or urine, through the absorbent body.

Note that the lower limits of the above ranges are non-limiting but have been set in consideration of production conditions such as cost.

[4] Application of Water-Absorbing Agent (as Absorbent Body)

The water-absorbing agent in accordance with an embodiment of the present invention is mainly preferably used as an absorbent body of absorbent articles such as disposable diapers and sanitary napkins. The water-absorbing agent is more preferably used as an absorbent body of an absorbent article in a manner such that there is a large amount of the absorbent body used per absorbent article. Note that the term "absorbent body" refers to a body obtained by providing the water-absorbing agent in sheet form, fiber form, cylindrical form, or the like. In an embodiment of the present invention, the absorbent body is preferably in sheet form.

In forming the absorbent body, it is also possible to use a water absorbing material such as pulp fiber, an adhesive, a non-woven fabric and/or the like, in combination with the water-absorbing agent in accordance with an embodiment of the present invention. In such a case, the amount of the water-absorbing agent contained in the absorbent body (this amount is hereinafter referred to as a "core concentration") is preferably 30 weight % to 100 weight %, more preferably 40 weight % to 100 weight %, even more preferably 50 weight % to 100 weight %, yet even more preferably 60 weight % to 100 weight %, particularly preferably 70 weight % to 100 weight %, and most preferably 75 weight % to 95 weight %.

In a case where the core concentration falls within the above ranges and the absorbent body is used as an upper layer part of an absorbent article, the absorbent article can maintain cleanness, i.e., a state of being white. The core concentration falling within the above ranges is therefore preferable. Further, in a case where the core concentration falls within the above ranges, an absorbent body which uses the water-absorbing agent in accordance with an embodiment of the present invention has an excellent ability to suck up body fluids such as urine and blood, and an excellent diffusion property. This enables efficient liquid distribution. As a result, it becomes possible to increase an updraw fluid retention amount under load of the absorbent body. The core concentration falling within the above ranges is therefore preferable.

[5] Physical Properties of Absorbent Body

An absorbent body of an embodiment of the present invention includes a water-absorbing agent which satisfies all of the physical properties (a) to (e), or a water-absorbing agent which further satisfies the physical properties (f) to (j) and the physical property (l).

In a case where the absorbent body includes a water-absorbing agent which has such physical properties, it is possible to increase the updraw fluid retention amount under load of the absorbent body, and it is possible to obtain a high-performance absorbent body for absorbent articles such as disposable diapers and sanitary napkins. The following description will discuss preferable ranges of the updraw fluid retention amount under load.

The absorbent body in accordance with an embodiment of the present invention has an updraw fluid retention amount under load which is preferably 22.5 g or more, more preferably 22.8 g or more, and even more preferably 23.0 g or more. The upper limit of the updraw fluid retention amount under load is not particularly limited but is preferably 30 g or less and more preferably 28 g or less, from the viewpoint of balance with other physical properties.

[6] Absorbent Article

An absorbent article in accordance with an embodiment of the present invention includes the absorbent body described above. Examples of the absorbent article include sanitary products such as disposable diapers and sanitary napkins.

In a case where the absorbent article is, for example, a disposable diaper, the disposable diaper is produced in such a manner that the absorbent body including the water-absorbing agent in accordance with an embodiment of the present invention is sandwiched between a top sheet and a back sheet, the top sheet being liquid permeable and positioned on a side of the disposable diaper which comes in contact with the wearer's skin during wearing, the back sheet being liquid impermeable and positioned on an side of the disposable diaper which is an outward side during wearing. Note that the disposable diaper also includes members which are known to a person skilled in the art, such as adhesive tape for fixing the disposable diaper after it has been put on by the wearer.

In a case where the absorbent body in accordance with an embodiment of the present invention is used in an absorbent article, and particularly a disposable diaper, the absorbent article exhibits excellent water absorption performance. This is because in the three-dimensional structure of the absorbent article during wearing, in a vertical direction, the absorbent body acts against the force of gravity to diffuse an absorbed liquid such as urine, and in a horizontal direction, the absorbent body is used effectively in its entirety. It is therefore possible to provide an absorbent article such as a disposable diaper which, for example, exhibits little urine leakage and provides favorable wearing comfort.

The absorbent article in accordance with an embodiment of the present invention therefore exhibits excellent core acquisition while in an inclined state (which is a factor that has been focused on for the first time in the present invention) and also exhibits excellent performance when evaluated in terms of, for example, re-wet and updraw distance in an inclined state which reflects actual usage.

Note that the absorbent body in accordance with an embodiment of the present invention may be suitably used not only in an absorbent article such as the above described sanitary products, but also in various applications such as animal urine absorbents, urine gelling agents for portable toilets, freshness keeping agents for fruits, vegetables, and the like, drip absorbers for meat and fishery products, ice packs, disposable body warmers, gelling agents for batteries, agricultural and horticultural soil water retaining agents (for plants, soil, and the like), dew condensation preventing agents, industrial waterproofing agents and packing agents, and artificial snow.

EXAMPLES

The following description will discuss the present invention more concretely with reference to Examples and Comparative Examples below. Note, however, that the present invention is not limited to these Examples and Comparative Examples, and that any Example derived from a proper combination of technical means disclosed in respective different Examples is also encompassed in the technical scope of the present invention. Note that electric devices used in the Examples, the Comparative Examples, and for measuring various physical properties of the water-absorbing agents each used a 200-V or 100-V power supply with a frequency of 60 Hz, unless otherwise specified. The various physical properties of the water-absorbing agents were measured at room temperature (20° C. to 25° C.) and at a relative humidity of 50%±5% RH, unless otherwise specified. For convenience, "liter" may be referred to as "l" or "L", and "weight %" may be referred to as "wt %".

[Physical Properties of Water-Absorbing Agent]

The following description will discuss methods for measuring various physical properties of the water-absorbing agent in accordance with an embodiment of the present invention. Note that in a case where a measurement target is something other than a water-absorbing agent, the wording "water-absorbing agent" is to be construed as indicating the actual measurement target, unless otherwise specified. For example, in a case where the measurement target is a water-absorbing resin powder, the wording "water-absorbing agent" used in descriptions of the measurement methods is to be construed as indicating the "water-absorbing resin powder".

(a) CRC

The centrifuge retention capacity (CRC) of a water-absorbing agent in accordance with an embodiment of the present invention was measured in conformity with an EDANA method (ERT 441.2-02) (see the descriptions in [1-3-1] above).

(b) AAP

An AAP of the water-absorbing agent in accordance with an embodiment of the present invention was measured in conformity with an EDANA method (ERT442.2-02). In the present invention, the load used during measurements was changed to 4.83 kPa (49 g/cm$^2$, 0.7 psi). Although the term "AAP" is used in the present specification, all AAP measurements herein are fluid retention capacity measurements carried out under a load of 4.83 kPa (see the descriptions in [1-3-2] above).

(c) PSD

The PSD (particle size distribution) (weight average particle diameter (D50), logarithmic standard deviation ($\sigma\zeta$) of particle size distribution, proportion of particles with a particle diameter of 600 μm or more and less than 850 μm (or less than 710 μm), proportion of particles with a particle diameter of 150 μm or more and less than 850 μm (or less than 710 μm)) of the water-absorbing agent in accordance with an embodiment of the present invention was measured by the method described later, in conformity with the measurement method described in columns 27 and 28 of U.S. Pat. No. 7,638,570 (see the descriptions in [1-3-3] above).

With regards to the particle size distribution, weight average particle diameter (D50), and the like, the values thereof can change depending on classification conditions (such as classified amount, classification time, mesh size of sieves, number of sieves, and type of classifier). As such, the particle size distribution, weight average particle diameter (D50), and the like are defined in accordance with the methods used for the present invention. Although there are some disclosures of particle size in the Patent Literatures described below in the Comparative Examples (which are additional tests of conventional art (Examples, Comparative Examples, and the like of Patent Literatures 3, 16, and 18 to 20)), the particle sizes described in the Comparative Examples below have been re-measured in accordance with the method used for the present invention. In cases where the method for measuring particle size distribution as used in a Patent Literature differs from the method used for the present invention, the particle size distribution disclosed in the Examples of that Patent literature may differ from the results indicated in the corresponding Comparative Example below. Such differences are due to the difference in measurement methods For the present invention, the sieves (IIDA TESTING SIEVES) used were in conformance with JIS Z 8801 and had mesh sizes of 850 µm, 710 µm, 600 µm, 500 µm, 425 µm, 212 µm, 200 µm, 150 µm, and 45 µm. The classifier used was a low-tap type classifier (IIDA SIEVE SHAKER ES-65). Classification time was 5 minutes.

(c') PSD of Particulate Hydrogel

On the other hand, the weight average particle diameter (D50) of a particulate hydrogel in accordance with an embodiment of the present invention and the logarithmic standard deviation ($\sigma\zeta$) of the particle size distribution of the particulate hydrogel were measured in the following manner.

First, 20 g of the particulate hydrogel (solid content: a weight %) and 500 g of an EMAL aqueous solution were introduced into a 1.14 L polypropylene container (cylindrical container having a bottom, with a height of 21 cm and diameter of 8 cm) and then stirred with use of a stirrer tip (length: 50 mm, diameter: 7 mm) at 300 rpm for 60 minutes, so that a dispersion liquid of the particulate hydrogel was obtained. The particulate hydrogel introduced had a temperature of 20° C. to 25° C.

The EMAL aqueous solution was a solution obtained by dissolving EMAL 20C (surfactant, available from Kao Corporation) into a 20 weight % aqueous sodium chloride solution such that the content of the EMAL 20C was 0.08 weight %.

After the above stirring was finished, the resultant dispersion liquid was supplied to the center of a set of JIS standard sieves placed on a rotary table. Each sieve of the set of JIS standard sieves had a diameter of 21 cm. Mesh size of the sieves was 8 mm, 4 mm, 2 mm, 1 mm, 600 µm, 300 µm, 150 µm, and 75 µm, in order from top to bottom. Next, the total amount of the particulate hydrogel left in the polypropylene container was washed out onto the sieves with use of 100 g of an EMAL aqueous solution.

Thereafter, the particulate hydrogel was classified by uniformly spraying 6000 g of an EMAL aqueous solution onto the sieves (from 30 cm above) with use of a shower (with 72 holes, flow rate: 6.0 L/min) in a manner such that the spraying area (50 cm²) entirely covered the sieve, while rotating the sieve by hand (20 rpm) (classification operation).

After the above classification operation, the particulate hydrogel remaining on each sieve was drained for approximately 2 minutes, and was then weighed. The results of the weighing were then used to calculate the weight % ratio of the particulate hydrogel remaining on each of the sieves, by use of Formula (2) below.

$$X=(w/W)\times 100 \qquad \text{Formula (2)}$$

Where:

X represents a weight % ratio (unit:weight %) of the particulate hydrogel remaining on an individual sieve, w represents a weight (unit: g) of the particulate hydrogel remaining on the individual sieve, and W represents a total (unit: g) of the weights of the particulate hydrogel remaining on each sieve.

In the classification operation, the particulate hydrogel was in a state of being swollen with the EMAL aqueous solution, and the degree of swelling was not uniform. As such, Formula (3) below was used to calculate what the equivalent mesh size (unit: mm) of a sieve would be in a case where the particulate hydrogel subjected to the classification operation was substituted with a particulate hydrogel which had not been swollen with the EMAL aqueous solution and which had a solid content of a weight %. The sieve mesh sizes calculated from Formula (3) and the weight % ratio of the particulate hydrogel remaining on each sieve were plotted on logarithmic probability paper. The particle diameter at which the cumulative oversize % R on the plot corresponds to 50 weight % was used as the weight average particle diameter (D50) of the particulate hydrogel.

$$R(\alpha)=(20/W)^{\{(1/3)\times r\}} \qquad \text{Formula (3)}$$

Where:

$R(\alpha)$ represents the mesh size (unit: mm) of a sieve on the assumption that the particulate hydrogel has a solid content of $\alpha$ weight %, W represents a total (unit: g) of the weights of the particulate hydrogel remaining on each sieve, and r represents the mesh size (unit: mm) of a sieve on which the particulate hydrogel swelled with EMAL aqueous solution remained.

Furthermore, the particle diameter at which the cumulative oversize % R is 84.1% (referred to as "X1") and the particle diameter at which the cumulative oversize % R is 15.9% (referred to as "X2") were found from the above plot, and a logarithmic standard deviation ($\sigma\zeta$) was found using Formula (4) below. A $\sigma\zeta$ having a smaller value means a narrower (sharper) particle size distribution.

$$\sigma\zeta=0.5\times\ln(X2/X1) \qquad \text{Formula (4)}$$

Where:

X1 represents particle diameter (unit: mm) when $R(\alpha)=84.1\%$, and

X2 represents particle diameter (unit: mm) when $R(\alpha)=15.9\%$.

(d) Moisture Content/Resin Solid Content

The moisture content of a water-absorbing agent in accordance with an embodiment of the present invention was measured in conformity with an EDANA method (ERT 430.2-02). For the present invention, in measurements of the moisture content (unit: weight %) of the water-absorbing agent, the amount of the water-absorbing agent (sample) was changed to 1.0 g, and the drying temperature was changed to 180° C. (see the descriptions in [1-3-4] above).

The resin solid content (unit: weight %) was defined as (100—moisture content).

(e) Average Gap Radius

An average gap radius of the water-absorbing agent in accordance with an embodiment of the present invention was measured in accordance with a method described below, with use of a measuring apparatus illustrated in FIG. 1. Discussed first are the principles of the measurement.

(Principles)

A height (head differential) h to which liquid rises via capillary action in a capillary having a radius R can be calculated by use of Formula (5) below.

$$h=2\gamma\cos\theta/(\sigma\times g\times R) \qquad \text{Formula (5)}$$

Where:

h represents a head differential (unit: m),

γ represents a surface tension (unit: kg/s²) of a liquid,

θ represents an angle of contact (unit: degrees)

ρ represents a density (unit: kg/m³) of the liquid, g represents gravitational acceleration (unit: m/s²), and R represents a radius (unit: µm) of a capillary.

Note that Formula (5) above has been derived from formulas disclosed in "ABSORBENCY" (ELSEVIER, editor: P. K. Chatterjee), specifically from Formula (2) "p=2γ cos θ/Rc (Laplace equation)" as disclosed on page 36 and Formula (5) "Leq=p/ρg" as disclosed on page 37. In Formula (5) of the present specification, "Leq" is represented as "h", and "Rc" is represented as R.

In the measuring apparatus 100 illustrated in FIG. 1, used as reference heights are a height of a liquid surface of a physiological saline 6 (0.9 weight % aqueous sodium chloride solution) contained in a liquid containing vessel 4, and a height of an upper surface of a glass filter 1 (porous glass plate) in a Buechner funnel 2. The Buechner funnel 2 is raised from 0 cm (the height of the liquid surface) to a height (head differential) of h cm. Liquid exists in between (in gaps between) particles of a swollen gel (a sample 9) which is placed in the glass filter 1. When the Buechner funnel 2 is raised, liquid which is held in gaps having a radius larger than a capillary radius (R, μm) (this liquid hereinafter referred to as "gap liquid") is released and flows out from the gaps.

As such, it is possible to find a distribution of the average gap radius (a capillary radius) of the swollen gel by: placing onto the glass filter 1 a swollen gel whose particles have been swelled to saturation and in which liquid completely fills the gaps (voids) between the particles; raising the Buechner funnel 2 gradually from the head differential from 0 cm; and measuring an amount of liquid remaining between the gaps at predetermined head differentials.

For the present invention, the gap radius is defined as the capillary radius R as calculated at each head differential using Formula (5) above. In other words, in a case where the head differential h (as measured between the height of the liquid surface of the physiological saline 6 in the liquid containing vessel 4 and the height of the upper surface of the glass filter 1 in the Buechner funnel 2) is changed from 0 cm to 60 cm in stages (1 cm, 2 cm, 5 cm, 10 cm, 20 cm, 30 cm, 60 cm) by raising the Buechner funnel 2, the liquid held in gaps having a capillary radius R relative to each head differential h is gradually released from those gaps. By measuring the amount of liquid released, it is possible to calculate the distribution of the gap radius (capillary radius). Then, plotting the calculated values on logarithmic probability paper provides a weight average particle diameter (D50) which is used as the average gap radius.

Specifically, in a case where in Formula (5), the surface tension of a 0.9 weight % aqueous sodium chloride solution (0.0728 kg/s$^2$) is used as γ, 0° is used as θ, the density of the 0.9 weight % aqueous sodium chloride solution (1000 kg/m$^3$) is used as ρ, and gravitational acceleration (9.8 m/s$^2$) is used as g, at head differentials of 1 cm, 2 cm, 5 cm, 10 cm, 20 cm, 30 cm, and 60 cm, the gap radius (maximum gap radius) of a gap which holds liquid is 1485 μm, 743 μm, 297 μm, 149 μm, 74.3 μm, 49.5 μm, and 24.8 μm, respectively.

(Operational Procedure)

The following description will discuss, with reference to FIG. 1, operational procedures used in measuring the average gap radius in accordance with an embodiment of the present invention.

First, the Buechner funnel 2 (diameter: 65 mm, inner diameter: 60 mm) having the glass filter 1 was prepared. Details of the Buechner funnel 2 having the glass filter 1 are as follows: manufactured by Sogo Laboratory Glass Works Co., Ltd.; product code no. 1175-33; particle number: #3; fine pore diameter: 20 μm to 30 μm; type: 17G; size: diameter=65 mm, height above filter plate=55 mm; and capacity: 140 ml. The capillary suction power of the Buechner funnel 2 was such that, even with a head differential h of 60 cm, the Buechner funnel 2 was able to act against negative pressure of a water column and hold water in the glass filter 1 and maintain a state where no air was introduced.

As illustrated in FIG. 1, a duct 3 was used to connect a lower part of the Buechner funnel 2 and a lower part of the liquid containing vessel 4. A support ring 5 was fitted to the Buechner funnel 2 for the purpose of moving the Buechner funnel 2 up and down. The support ring was attached to a stand 8. Thereafter, the liquid containing vessel 4 was placed on a balance 7, and the physiological saline 6 was introduced into the liquid containing vessel 4 (into the measuring apparatus). Next, after confirming that air had not entered into the duct 3 or into a portion of the Buechner funnel 2 lower than the glass filter 1, the Buechner funnel 2 was fixed to the stand 8 such that there was a head differential h of 60 cm between the height of the liquid surface of the physiological saline 6 in the liquid containing vessel 4 and the height of an upper surface of the glass filter 1 in the Buechner funnel 2. Thereafter, the balance 7 was zeroed.

Next, approximately 0.9 g of a sample 9 (water-absorbing agent) was quickly and evenly dispersed onto the glass filter 1.

Next, the Buechner funnel 2 was fixed to the stand 8 such that the head differential h was −3 cm (that is, so that the upper surface of the glass filter 1 was lower), and the sample 9 was allowed to stand still for 20 minutes such that the sample 9 became swollen with the physiological saline 6. During this time, the sample 9 was completely immersed in the physiological saline 6 in a state with no gas bubbles.

Next, the head differential h was adjusted to 0 cm, and the sample 9 was allowed to stand still for 40 minutes such that the sample 9 swelled to saturation. Thereafter, the measurement value (unit: g) shown by the balance 7 was recorded (this value is represented as "A0"). Note that in cases where the sample 9 had not swollen to saturation after 40 minutes, the sample 9 was allowed to stand still for a longer period.

Next, the head differential h was adjusted to 1 cm, the sample 9 was allowed to stand still for 7 minutes, and then the measurement value (unit: g) shown by the balance 7 was recorded (this value is represented as "A1"). Note that the time that allowed for the gap liquid to be released such that equilibrium is achieved (i.e., the amount of time the sample 9 is allowed to stand still), can be lengthened as appropriate in accordance with the size of the gaps of the sample.

In the same manner, the head differential h was adjusted to 2 cm, 5 cm, 10 cm, 20 cm, 30 cm, and 60 cm sequentially. Each time, the sample 9 was allowed to stand still for 7 minutes, and the measurement value (unit: g) shown by the balance 7 was recorded (these values being represented as "A2", "A5", "A10", "A20", "A30", and "A60", respectively).

Next, in order to cause complete release of the liquid held in gaps when the head differential h was 60 cm, the sample 9 was removed from the Buechner funnel 2 and drained with use of a centrifuge (250 G, 6 minutes). The weight (unit: g) of the sample after draining, referred to here as a weight B, was measured.

The amount of liquid in gaps was calculated using the measurement values shown by the balance 7 and the weight B, as obtained in the above-described measurements. "A0-B" (unit: g) represents an amount of liquid in gaps which completely fills the gaps of the sample (hereinafter, a "total amount of liquid in all gaps"), and "A1-B", "A2-B", "A5-B", "A10-B", "A20-B", "A30-B", and "A60-B" each represent an amount of liquid in gaps held by capillary action against the negative pressure of the water column at each respective head differential (hereinafter, a "held amount of liquid in gaps").

The total amount of liquid in all gaps and the held amounts of liquid in gaps were used to calculate a weight percentage (unit: weight %) of the held amount of liquid in gaps at each head differential. These calculated values and the above-described values of the maximum gap radiuses were plotted on logarithmic probability paper so as to obtain a graph. A gap radius value on the graph corresponding to a held amount of liquid in gaps whose weight percentage is 50 weight % was used as the average gap radius (unit: μm) of the sample.

Note that in a case where spherical glass beads having particle diameters of 350 μm to 500 μm were used as a standard sample and the average gap radius was found by the above operational procedures, the resulting value was 86 μm. For spherical glass beads having a particle diameter of 1000 μm to 1180 μm, the resulting value was 217 μm.

(f) Updraw Fluid Retention Capacity Under Load

An updraw fluid retention capacity under load of a water-absorbing agent in accordance with an embodiment of the present invention was measured in accordance with a method described below, with use of a measuring apparatus 200 illustrated in FIG. 2. The following description will discuss, with reference to FIG. 2, operational procedures used in measuring the updraw fluid retention capacity under load in accordance with an embodiment of the present invention.

Firstly, a fritted glass funnel 10 was prepared. The fritted glass funnel 10 had a pore diameter of 16 μm to 40 μm (P40), a thickness of 7 mm, and a capacity of 500 ml. Specifically, a grade 3 filter funnel made of Duran glass (manufactured by Schott) was used.

The frit of the fritted glass funnel 10 had a radius of 30 cm and a water flow capability of 50 ml/minute at a pressure differential of 50 mbar at 20° C. The capillary suction power of the frit was such that, even with a head differential H of 20 cm, the frit was able to act against negative pressure of a water column and hold water in the fritted glass funnel 10, and maintain a state where no air was introduced.

Figure 2:
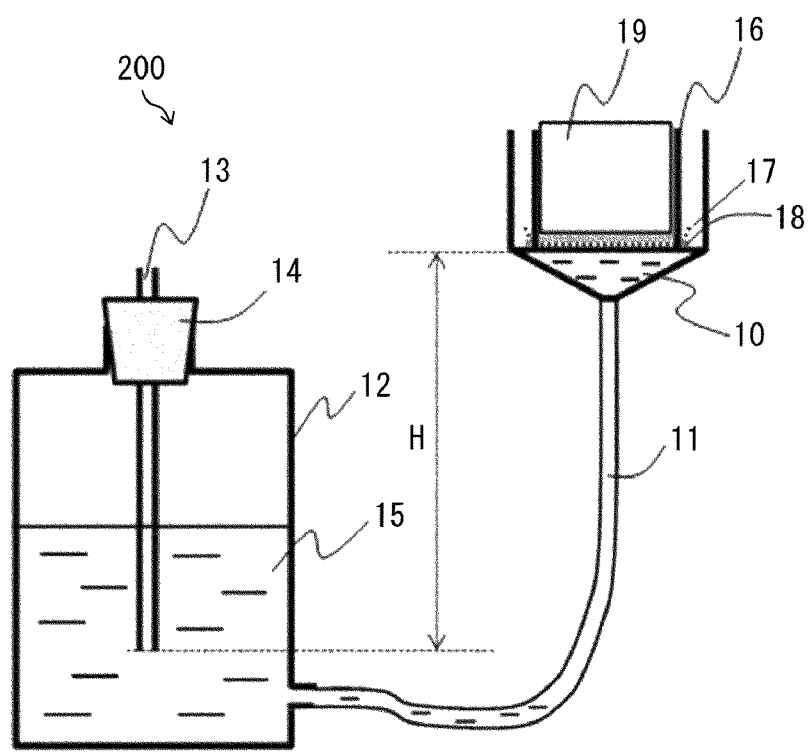
FIG. 2 is an elevational view schematically illustrating a configuration of a measuring apparatus for measuring an updraw fluid retention capacity under load of a water-absorbing agent and an amount of liquid updrawn by an absorbent body.

As illustrated in FIG. 2, a duct 11 was used to connect a lower part of the fritted glass funnel 10 and a lower part of a liquid containing vessel 12. An upper part of the liquid containing vessel 12 was closed by a rubber stopper 14 having a glass tube 13 (inner diameter: 3 mm) passing therethrough. Thereafter, a physiological saline 15 (a 0.9 weight % aqueous sodium chloride solution) was introduced into the liquid containing vessel 12 such that a liquid surface was higher than a lower end of the glass tube 13 inserted into the liquid containing vessel 12. Thereafter, the physiological saline 15 was removed from inside the glass tube 13 such that a height of an air-liquid interface in the glass tube 13 was even with the lower end of the glass tube 13.

Next, after confirming that air had not entered the duct 11 and a lower end of the fritted glass funnel 10, the fritted glass funnel 10 was fixed such that there was head differential H of 20 cm or 30 cm between the height of the lower end of the glass tube 13 inserted into the liquid containing vessel 12 and the height of an upper surface of the frit of the fritted glass funnel 10. Note that values measured in a case where the head differential H was 20 cm are denoted as "updraw fluid retention capacity under load with a 20 cm water column", and values measured in a case where the head differential H was 30 cm are denoted as "updraw fluid retention capacity under load with a 30 cm water column".

Next, a measurement section was produced. First, an absorbent paper 17 (manufactured by Nippon Paper Crecia Co., Ltd.; Kimwipe (model no.: S-200)) cut into an square (8 cm per side) was placed at the bottom of a plastic support cylinder 16 having an inner diameter of 60 mm. After the absorbent paper 17 was fixed with a metal ring 18, 0.9 g of a water-absorbing agent (this weight being represented as "W1") was dispersed evenly on the absorbent paper 17, the water-absorbing agent being used as a sample. A weight 19 was placed on top of the water-absorbing agent, the weight 19 being adjusted so as to uniformly apply a load of 2.07 kPa to the water-absorbing agent. In other words, the measurement section was produced by placing, onto the water-absorbing agent, the weight 19 which weighed 596 g, the weight 19 having an outer diameter slightly less than 60 mm such that there was no gap between the weight 19 and the support cylinder 16 but vertical movement of the weight 19 was not impeded. The weight of the measurement section (unit: g) was measured (this weight being represented as "W2").

The water-absorbing agent was caused to swell by placing the measurement section on the fritted glass funnel 10 and letting the measurement section stand still for 60 minutes. Thereafter, the measurement section was lifted, and the weight of the measurement section (unit: g) was measured (this weight being represented as "W3").

The updraw fluid retention capacity under load (unit: g/g) was calculated in accordance with Formula (6) below, using the values for W1, W2, and W3 as measured above.

$$(\text{Updraw fluid retention capacity under load})(g/g) = (W3-W2)/W1 \quad \text{Formula (6)}$$

(g) Amount of Liquid Updrawn by Absorbent Body

In order to evaluate the water-absorbing agent in accordance with an embodiment of the present invention with regards to performance as an absorbent body, the following procedure was used to determine the amount of liquid updrawn by the absorbent body.

First, a model absorbent body (water-absorbing agent concentration: 60 weight %) was prepared as below, as an absorbent body for use in an absorbent articles such as disposable diapers and sanitary napkins.

Specifically, 0.6 g of wood-ground pulp was moistened by spraying mist onto the pulp for 5 seconds with use of an ultrasonic moistening device (manufactured by Nippo Co., Ltd.; NP-408; atomizing capability: 600 g/hr). The moistened pulp and 0.9 g±0.0050 g of water-absorbing agent were put into a food processor (manufactured by Panasonic Corporation; MK-K48P), and were pulverized and mixed for 5 seconds. In a case where the pulp and the water-absorbing agent were not mixed uniformly, the mixing time period was extended.

Next, in the measuring apparatus 200 described in "(f) Updraw fluid retention capacity under load", instead of a water-absorbing agent, the mixture of the pulp and the water-absorbing agent obtained by the above mixing was placed into the support cylinder 16. The weight 19 was used to apply a pressure of 2.07 kPa to the mixture for 5 minutes, and the mixture was considered to be an absorbent body. Note that by preparing the absorbent body in the above manner, a measurement section was also prepared.

Thereafter, the weight of the measurement section (unit: g) was measured in the same manner as described in "(f) Updraw fluid retention capacity under load" (this weight being represented as "W4").

Next, the fritted glass funnel 10 was fixed such that there was head differential H of 20 cm between the height of the lower end of the glass rod 13 inserted into the liquid containing vessel 12 and the height of an upper surface of the frit of the fritted glass funnel 10. Thereafter, the absorbent body was caused to swell by placing the measurement section on the fritted glass funnel 10 and letting the measurement section stand still for 60 minutes. Thereafter, the measurement section was lifted, and the weight of the measurement section (unit: g) was measured (this weight being represented as "W5").

The amount of liquid updrawn by the absorbent body (unit: g) was calculated in accordance with Formula (7) below, using the values for W4 and W5 as measured above.

(Amount of liquid updrawn by absorbent body)(g)=$W5-W4$    Formula (7)

(h) Evaluation of Re-Wet and Updraw Distance in Inclined State

Conventionally, evaluation of model sanitary products has been carried out by determining re-wet, a liquid diffusion property, and the like of a product in a level state. However, since sanitary products take on a curved surface in actual use for a human body (particularly, the buttocks), such evaluations have not accurately assessed the effects of model sanitary products. The present measurement method was discovered for the present invention. The following description will discuss core acquisition in an inclined state.

In order to confirm the effect of the water-absorbing agent in accordance with an embodiment of the present invention as used in a sanitary product (absorbent article) such as a disposable diaper, the re-wet and updraw distance of a model sanitary product were measured while the model sanitary product was in an inclined state. These measurements were carried out by the methods described below, with use of a sanitary product evaluation apparatus (see FIGS. 3 and 4).

Figure 3:
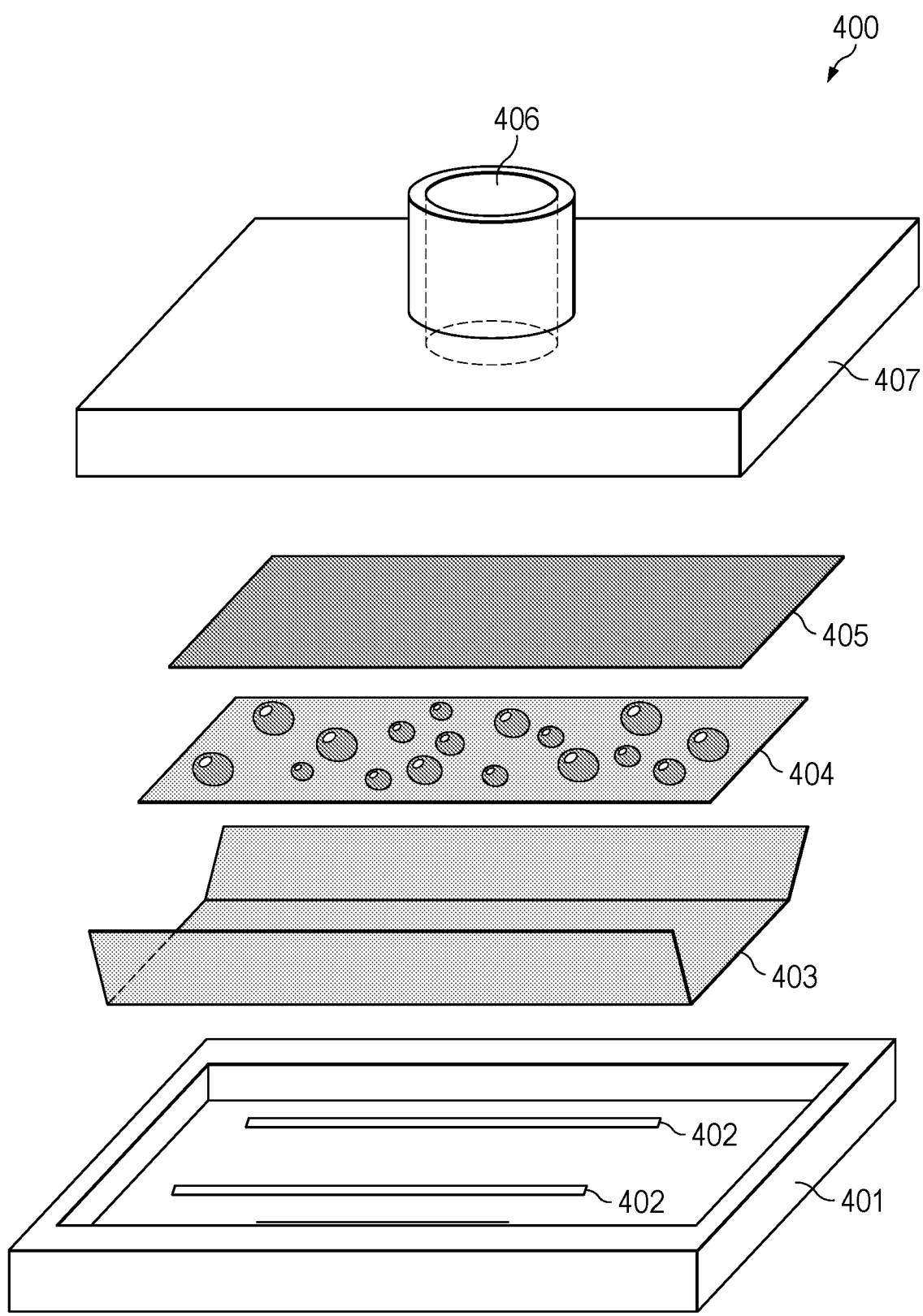
FIG. 3 is an exploded perspective view schematically illustrating a sanitary product evaluation apparatus for measuring re-wet and an updraw distance of a sanitary product (absorbent article) in an inclined state.

First, as illustrated in FIG. 3, to a central portion of an acrylic resin tray 401 having internal dimensions of 401 mm (length)×151 mm (width)×30 mm (height) and external dimensions of 411 mm (length)×161 mm (width)×35 mm (height), two strips of double-side tape 402 (manufactured by Nichiban Co., Ltd.; double-side tape NICETACK NW-10) each having a width of 10 mm and a length of 400 mm were attached in such a pattern as to extend parallel to respective corresponding lengthwise inner walls and to be separated from the lengthwise inner walls by 25 mm. Next a tissue 403 having a thickness of 0.1 mm, a length of 400 mm, and a width of 300 mm (prepared by cutting a Kimwipe (model no.: L-100) available from Nippon Paper Crecia Co., Ltd. into the above dimensions) was folded into thirds, at 100 mm intervals along the widthwise direction. In other words, three sections were created in the tissue 403, each section measuring 400 mm in length and 100 mm in width. Thereafter, a central section (400 mm in length and 100 mm in width) of the tissue 403 was affixed to the two strips of double-side tape 402 in a mariner such that the tissue 403 was not wrinkled.

Next, 20 g of a water-absorbing agent 404 was spread out evenly in an area (400 mm in length and 100 mm in width) in the center of the tissue 403, the area being 25 mm inward of each of the lengthwise inner walls of the tray 401. Note that before the water-absorbing agent 404 was spread out, the wall surfaces of the tray 401 were subjected to an antistatic treatment so as to prevent the occurrence of static electricity.

Figure 5:
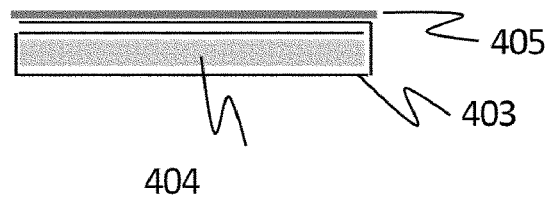
FIG. 5 is a side view illustrating a positional relationship between a water-absorbing agent, a tissue, and a non-woven fabric in the sanitary product evaluation apparatus of FIG. 3.

The sections at both outer portions of the tissue 403 (i.e., portions of the tissue 403 on which the water-absorbing agent had not been spread) were folded over the water-absorbing agent 404 spread thusly, and then a non-woven fabric 405 (400 mm in length by 100 mm in width) was placed onto the tissue 403. The non-woven fabric 405 was positioned so as to be evenly distanced from both of the lengthwise inner walls of the tray 401 and evenly distanced from both of the widthwise inner walls of the tray 401. That is, the water-absorbing agent 404, the tissue 403, and the non-woven fabric 405 were placed on the tray 401 so as to have a positional relationship as illustrated in FIG. 5, as viewed from a widthwise side of the tray 401.

Next, an acrylic resin lid 407 (with a length of 400 mm, a width of 150 mm, and a thickness of 20 mm) having, at a central portion thereof, a cylindrical inlet 406 (with a cylindrical portion having a height of 100 mm) having an inner diameter of 30 mm was placed on the non-woven fabric 405. In this way, a sanitary product evaluation apparatus 400 was prepared. The lid 407 had a weight of 1.5 kg.

Figure 4:
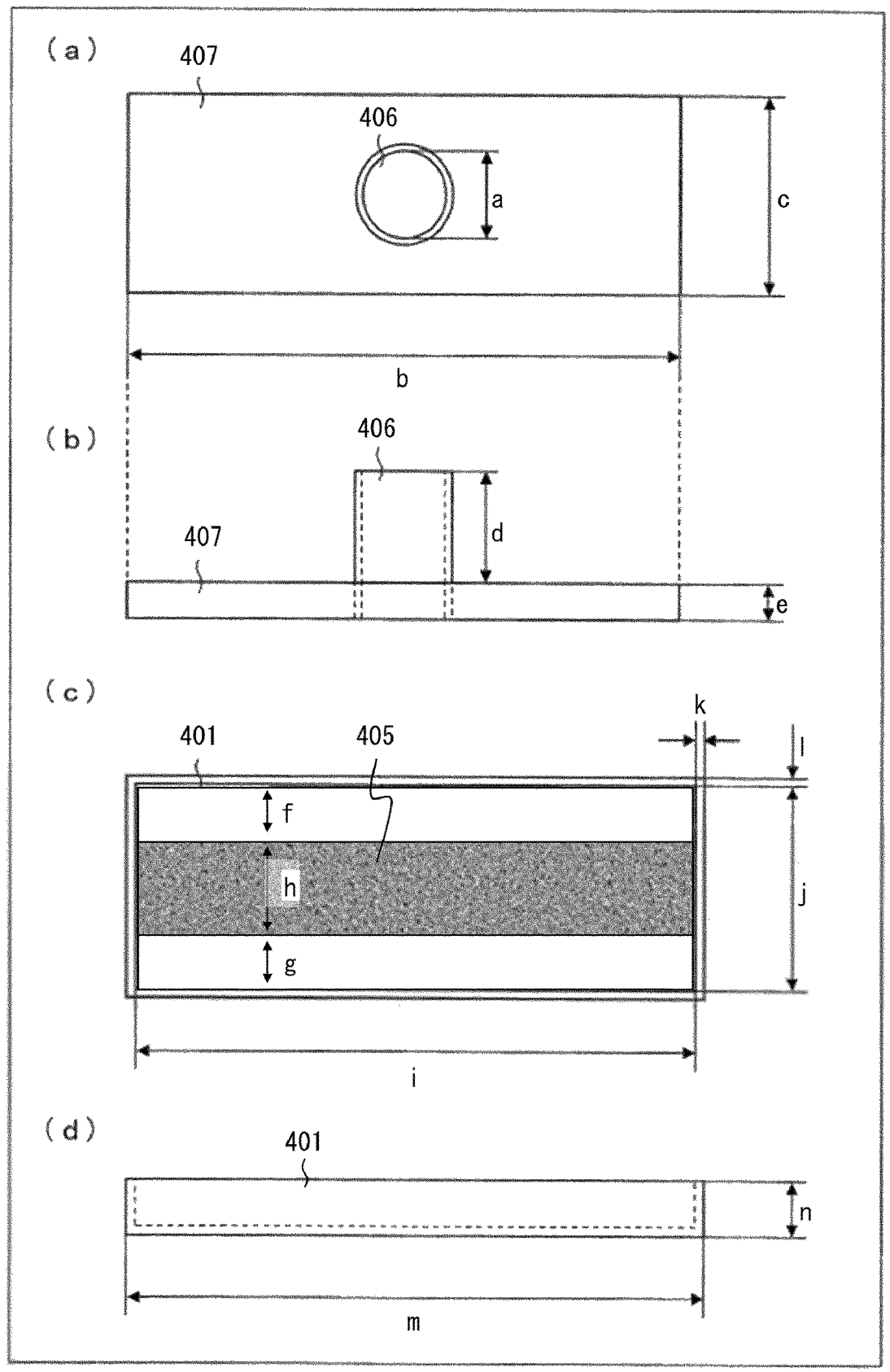
FIG. 4 is composed of the following. (a) of FIG. 4: a plan view of a lid of the sanitary product evaluation apparatus of FIG. 3; (b) of FIG. 4: a side view of the lid; (c) of FIG. 4: a plan view of a tray of the sanitary product evaluation apparatus of FIG. 3; and (d) of FIG. 4: a side view of the tray.

The following description will further discuss the tray 401 and the lid 407 of the sanitary product evaluation apparatus 400 with reference to FIG. 4. (a) of FIG. 4 is a plan view of the lid. (b) of FIG. 4 is a side view of the lid. (c) of FIG. 4 is a plan view of the tray. (d) of FIG. 4 is a side view of the tray.

In (a) of FIG. 4, the letter "a" indicates the inner diameter of the inlet 406, the letter "b" indicates the length of the lid 407, and the letter "c" indicates the width of the lid 407. In (b) of FIG. 4, the letter "d" indicates the height of the cylindrical part of the inlet 406, and the letter "e" indicates the thickness of the lid 407. In (c) of FIG. 4, the letter "i" indicates a lengthwise inner dimension (401 mm) of the tray 401, and the letter "j" indicates a widthwise inner dimension (151 mm) of the tray 401. The letter "k" indicates a difference (10 mm) between the lengthwise inner dimension and the lengthwise outer dimension of the tray 401. The letter "l" indicates a difference (10 mm) between the widthwise inner dimension and widthwise outer dimension of the tray 401. In (d) of FIG. 4, the letter "m" indicates a lengthwise outer dimension (411 mm) of the tray 401, and the letter "n" indicates a height (35 mm) of the tray 401.

(c) of FIG. 4 illustrates how the non-woven fabric 405 is arranged in the tray 401. In (c) of FIG. 4, the letter "h" indicates the width (100 mm) of the non-woven fabric 405, and the letters "f" and "g" each indicate that the non-woven fabric 405 is positioned so as to be 25 mm inward of each of the lengthwise inner walls of the tray 401 (f=g).

Figure 6:
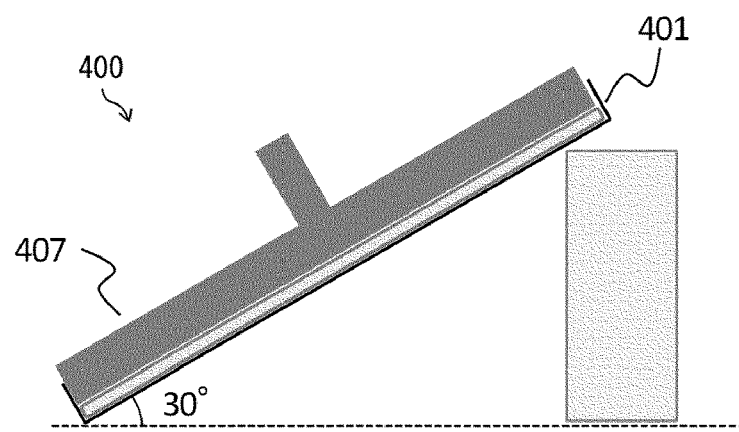
FIG. 6 is a side view schematically illustrating a configuration of the sanitary product evaluation apparatus of FIG. 3 during measurement.

In the measurements of the re-wet and updraw distance in an inclined state, the sanitary product evaluation apparatus 400 was set so as to be inclined at an angle of 30° relative to a horizontal plane, as illustrated in FIG. 6. The following description will discuss the specific methods for measuring re-wet and updraw distance in an inclined state.

100 g of 0.9 weight % aqueous sodium chloride solution (preferably colored with 0.04 g of blue no. 1 relative to 1000 g of the aqueous solution) having a temperature adjusted to 37° C.±0.5° C. was poured through the inlet 406 of the sanitary product evaluation apparatus 400 prepared as above. Specifically, the 0.9 weight % aqueous sodium chloride solution was first poured up to a maximum possible height, but so as not to overflow from the upper end of the inlet. Thereafter, as the aqueous solution was absorbed by the water-absorbing agent 404 and the liquid surface of the aqueous solution lowered, the remainder of the 0.9 weight % aqueous sodium chloride solution was poured up to a height so as not to overflow from the upper end of the inlet.

The aqueous solution poured thusly passed through the non-woven fabric 405 and the tissue 403 and was absorbed by the water-absorbing agent 404. After 10 minutes had passed since the commencement of the first pouring of the aqueous solution, 100 g of 0.9 weight % aqueous sodium chloride solution was poured a second time. Similarly, after 10 minutes had passed since the commencement of the second pouring of the aqueous solution, 100 g of 0.9 weight % aqueous sodium chloride solution was poured a third time.

Paper towels (manufactured by Oji Nepia Co., Ltd.; Kitchen Towel 100) were folded such that a shorter side of each paper towel was bisected. Five paper towels folded in half in this manner were placed on top of each other so as to form one set, and three of such sets were placed on top of each other so as to form one bunch. Each paper towel had a width of 110 mm and a length of 228 mm when folded in half. The weight (unit: g) of the bunch was measured up to one decimal place past the decimal point (this weight is represented as "W6").

After three minutes had passed since the end of the third pouring of aqueous solution, the sanitary product evaluation apparatus 400 which had been inclined was placed on a level surface, and the lid 407 was removed. Then the bunch of paper towels was placed onto the non-woven fabric 405 such that the center of the bunch was aligned with a position where the inlet 406 had been on the non-woven fabric 405. Next, an acrylic plate (with a length of 250 mm, a width of 140 mm, and a thickness of 10 mm) was placed on the bunch, and a 12.0 kg weight was placed on the acrylic plate. This applied a pressure of approximately 4.8 kPa to the paper towels.

After the measuring apparatus was allowed to stand still for 1 minute, the weight, the acrylic plate and the bunch of paper towels were removed from the non-woven fabric 405, and the weight (unit: g) of the bunch of paper towels was measured up to one decimal place past the decimal point (this weight is represented as "W7"). Then, the amount of liquid absorbed by the paper towels was calculated in accordance with Formula (8) below, and this amount was considered to be the re-wet (g) in an inclined state.

$$\text{Re-wet in inclined state}(g)=W7-W6 \quad \text{Formula (8)}$$

Figure 7:
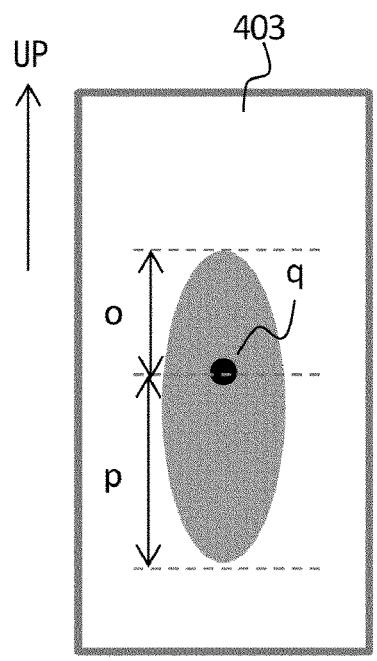
FIG. 7 is a plan view illustrating an upward updraw distance and a downward updraw distance of a water-absorbing agent, as seen in the sanitary product evaluation apparatus of FIG. 3 after measurement.

After the measurement of the re-wet in the inclined state, the non-woven fabric 405 was removed, and an upward updraw distance (cm) and a downward updraw distance (cm) were determined. The upward updraw distance (cm) was measured as a distance from a center of where the inlet 406 had been positioned on the water-absorbing agent 404 to an upper end of absorption of the aqueous solution by the water-absorbing agent 404 (i.e., what would be the upper end in the inclined state). The downward updraw distance was measured as a distance from the center of where the inlet 406 had been positioned on the water-absorbing agent 404 to a lower end of absorption of the aqueous solution by the water-absorbing agent 404 (i.e., what would be the lower end in the inclined state). Specifically, in FIG. 7, the letter "q" indicates the center of where the inlet 406 had been positioned on the water-absorbing agent 404, the letter "o" indicates the upward updraw distance, and the letter "p" indicates the downward updraw distance. In this way, the upward and downward updraw distances were measured.

(i) Degradable Soluble Component

A 35 mm rotor was placed into a 250 ml plastic container having a lid. Then, 200.0 g of a 0.9 weight % aqueous sodium chloride solution containing 0.05 weight % of L-ascorbic acid was measured and introduced into the plastic container. Into this aqueous solution, 1.00 g of a particulate water-absorbing agent which had been subjected to 600 μm/300 μm classification was added. The plastic container was then sealed with an inner and outer lid.

The plastic container was left to stand still for 2 hours in an incubator set to 60° C.±2° C. After 2 hours, the plastic container was removed from the incubator, and a soluble component of the particulate water-absorbing agent was extracted by stirring for 1 hour with use of a stirrer (at approximately 150 rpm). The extract containing the soluble component was filtered with the use of one sheet of filter paper (Advantec Toyo Kaisha, Ltd., Product name: JIS P 3801, No. 2, thickness 0.26 mm, retains particle diameter of 5 μm), and 50.0 g of the obtained filtrate was weighed and used as a solution for measurement.

Thereafter, the degradable soluble component was determined by operations in the same manner as a soluble component measurement in conformance with an EDANA method (ERT 470.2-02). A soluble component ratio (mass %) obtained thusly was considered to be the degradable soluble component.

Example 1

Into a 2 L polypropylene container was introduced 421.7 parts by weight of acrylic acid, 140.4 parts by weight of a 48 weight % aqueous sodium hydroxide solution, 1.8 parts by weight of polyethyleneglycol diacrylate (average number of polyethyleneglycol units (average n number) of 9), 2.7 parts by weight of a 1.0 weight % aqueous diethylenetriamine pentaacetic acid/trisodium solution, and 395.3 parts by weight of deionized water. These substances were mixed so that an aqueous solution (1) was obtained. The deionized water had been preheated to 40° C.

Next, while the aqueous solution (1) was stirred, 211.9 parts by weight of a 48 weight % aqueous sodium hydroxide solution was added to and mixed with the aqueous solution (1) under atmospheric pressure over a period of approximately 30 seconds so that an aqueous monomer solution (1) was obtained. Note that a temperature of the aqueous monomer solution (1) increased to approximately 80° C. due to heat of neutralization and heat of dissolution which were generated during the mixing.

Thereafter, when the temperature of the aqueous monomer solution (1) reached 78° C., 17.6 parts by weight of a 4 weight % aqueous sodium persulfate solution was added as a polymerization initiator, and a resultant mixture was stirred for approximately 5 seconds such that a reaction liquid (1) was obtained.

Next, the reaction liquid (1) was poured into a stainless steel vat-type vessel under atmospheric pressure. The vat-type vessel had dimensions of 200 mm×260 mm at the bottom of the vessel and 460 mm×560 mm at the top of the vessel, with a height of 140 mm. The vat-type vessel had a trapezoidal cross section at its center. A silicone sheet had been affixed to an inner surface of the vat-type vessel. Before the reaction liquid (1) was poured into the vat-type vessel, the vat-type vessel was preheated by being placed on a hot plate heated to 50° C.

After the reaction liquid (1) was poured into the vat-type vessel, a polymerization reaction commenced within 1 minute. As the polymerization reaction proceeded, the polymerization reaction caused the reaction liquid (1) to expand and foam upward in various directions while water vapor was generated. Thereafter, the reaction liquid (1) contracted to a size slightly larger than the bottom surface of the vat-type vessel. The polymerization reaction (expansion and contraction) ended within approximately 1 minute. Through this polymerization reaction, a crosslinked hydrogel polymer (hereinafter referred to as a "hydrogel") (1) was obtained.

Next, after being cut to an appropriate size, the hydrogel (1) was supplied to a screw extruder and subjected to gel-crushing such that a particulate hydrogel (1) was obtained. The rotation speed of a screw shaft of the screw extruder was set to 160 rpm. The particulate hydrogel (1) had a weight average particle diameter (D50) of 692 μm.

Next, the particulate hydrogel (1) was spread onto a metal gauze with a mesh size of 300 μm (50 mesh) and then placed in a hot air dryer. The particulate hydrogel (1) was then dried by passing hot air at a temperature of 190° C. over the particulate hydrogel (1) for 30 minutes, such that a dried polymer (1) was obtained. Next, the dried polymer (1) was introduced into a roll mill and pulverized. Thereafter, the dried polymer (1) thus pulverized was classified with use of two JIS standard sieves having respective mesh sizes of 710 μm and 150 μm. In this way, a water-absorbing resin powder (1) whose particles were foamed particles having a non-uniformly pulverized particle shape was obtained.

The water-absorbing resin powder (1) obtained through the above series of operations had a moisture content of 3.5 weight %, a CRC of 35.8 g/g, a weight average particle diameter (D50) of 360 μm, a logarithmic standard deviation (σζ) of a particle size distribution of 0.37, an average gap radius of 270 μm, and a specific surface area of 30.8 m$^2$/kg. Physical properties of the water-absorbing resin powder (1) are shown in Table 1.

Next, 3.5 parts by weight of a surface-crosslinking agent solution (1) composed of 0.4 parts by weight of ethylene carbonate, 0.6 parts by weight of propylene glycol, and 2.5 parts by weight of deionized water was added to 100 parts by weight of the water-absorbing resin powder (1) and mixed until uniformity was obtained. In this way, a humidified mixture (1) was obtained. The humidified mixture (1) was then subjected to a heating treatment at 205° C. for 25 minutes and subsequently force-cooled to 60° C. so that a surface-crosslinked water-absorbing resin powder (hereinafter referred to as "water-absorbing resin particles") (1) was obtained. Note that in Example 1, the water-absorbing resin particles (1) are treated as being an end product. As such, the water-absorbing resin particles (1) were considered to be a water-absorbing agent (1). Physical properties of the water-absorbing agent (1) are shown in Table 2. The particles of the water-absorbing agent (1) had a non-uniformly pulverized particle shape. The degradable soluble component of the water-absorbing agent (1) was measured as being 19 weight %.

Example 2

A granulated material powder was prepared by use of water-absorbing resin fine powder generated by the pulverization using the roll mill in Example 1.

First, in the pulverization of Example 1, water-absorbing resin fine powder which passed through the JIS standard sieve with a mesh size of 150 μm was collected in an amount of 55 parts by weight. Next, while the water-absorbing resin fine powder was stirred with use of a food processor (manufactured by Panasonic Corporation; MK-K48P), 45 parts by weight of deionized water was added to the water-absorbing resin fine powder and mixed therewith for 30 seconds such that a granulated material was obtained.

Next, the granulated material was spread onto a metal gauze with a mesh size of 300 μm (50 mesh) and then placed in a hot air dryer. The granulated material was then dried by passing hot air at a temperature of 190° C. over the granulated material for 30 minutes, such that a dried granulated material was obtained. Next, the dried granulated material was introduced into a roll mill and pulverized. Thereafter, the dried granulated material thus pulverized was classified with use of two JIS standard sieves having respective mesh sizes of 710 μm and 150 μm. In this way, a fine-powder-derived granulated material (material composed of recovered fine powder) whose particles had a non-uniformly pulverized particle shape was obtained.

Next, 25 parts by weight of the fine-powder-derived granulated material was mixed uniformly with 100 parts by weight of the water-absorbing resin powder (1) obtained in Example 1, so that a water-absorbing resin powder (2) whose particles had a non-uniformly pulverized particle shape was obtained. The water-absorbing resin powder (2) contained the fine-powder-derived granulated material in an amount of 20 weight %.

The water-absorbing resin powder (2) obtained through the above series of operations had a moisture content of 3.2 weight %, a CRC of 35.2 g/g, a weight average particle diameter (D50) of 353 μm, a logarithmic standard deviation (σζ) of a particle size distribution of 0.38, an average gap radius of 265 μm, and a specific surface area of 32.1 m$^2$/kg. Physical properties of the water-absorbing resin powder (2) are shown in Table 1.

Next, 2.4 parts by weight of a surface-crosslinking agent solution (2) composed of 0.1 parts by weight of 2-oxazolidinone, 0.1 parts by weight of propylene glycol, 0.6 parts by weight of isopropanol, and 1.6 parts by weight of deionized water was added to 100 parts by weight of the water-absorbing resin powder (2) and mixed until uniformity was obtained. In this way, a humidified mixture (2) was obtained. The humidified mixture (2) was then subjected to a heating treatment at 205° C. for 25 minutes and subsequently force-cooled to 60° C. so that water-absorbing resin particles (2) were obtained. Note that in Example 2, the water-absorbing resin particles (2) are treated as being an end product. As such, the water-absorbing resin particles (2) were considered to be a water-absorbing agent (2). Physical properties of the water-absorbing agent (2) are shown in Table 2. The particles of the water-absorbing agent (2) had a non-uniformly pulverized particle shape. The degradable soluble component of the water-absorbing agent (2) was measured as being 19 weight %.

Example 3

Water-absorbing resin particles (3) were obtained by carrying out the same operations as in Example 1, except for the following changes: the 3.5 parts by weight of the surface-crosslinking agent solution (1) were replaced with 5.03 parts by weight of a surface-crosslinking agent solution (3) composed of 0.03 parts by weight of ethyleneglycoldiglycidyl ether, 1.5 parts by weight of propylene glycol, and 3.5 parts by weight of deionized water; and the heating treatment was carried out at 100° C. for 40 minutes. Note that in Example 3, the water-absorbing resin particles (3) are treated as being an end product. As such, the water-absorbing resin particles (3) were considered to be a water-absorbing agent (3). Physical properties of the water-absorbing agent (3) are shown in Table 2. The particles of the water-absorbing agent (3) had a non-uniformly pulverized particle shape.

Comparative Example 1

A comparative water-absorbing resin powder (1) whose particles had a non-uniformly pulverized particle shape was obtained by: introducing the dried polymer (1) of Example 1 into a roll mill and pulverizing the dried polymer (1); and, thereafter, classifying the dried polymer (1) thus pulverized with use of two JIS standard sieves having respective mesh sizes of 850 μm and 150 μm.

The comparative water-absorbing resin powder (1) obtained through the above series of operations had a moisture content of 3.9 weight %, a CRC of 36.1 g/g, a weight average particle diameter (D50) of 384 μm, a logarithmic standard deviation ($\sigma\zeta$) of a particle size distribution of 0.39, an average gap radius of 305 μm, and a specific surface area of 29.8 m$^2$/kg. Physical properties of the comparative water-absorbing resin powder (1) are shown in Table 1.

Next, comparative water-absorbing resin particles (1) were obtained by carrying out surface crosslinking in the same manner as in Example 1. Next, 1.0 part by weight of a liquid permeability improving agent composed of 0.75 parts by weight of a 50 weight % aqueous aluminum sulfate solution and 0.25 parts by weight of a 60 weight % aqueous sodium lactate solution was added as an additive to 100 parts by weight of the comparative water-absorbing resin particles (1) and mixed until uniformity was obtained. Thereafter, the mixture was crushed until it passed through a JIS standard sieve having a mesh size of 850 μm, so that a comparative water-absorbing agent (1) was obtained as an end product. Physical properties of the comparative water-absorbing agent (1) are shown in Table 2. The particles of the comparative water-absorbing agent (1) had a non-uniformly pulverized particle shape.

Comparative Example 2

A comparative particulate hydrogel (2), a comparative water-absorbing resin powder (2), and comparative water-absorbing resin particles (2) were obtained by carrying out the same operations as in Example 1, except that the amount of the polyethyleneglycol diacrylate (average n number: 9) was changed to 2.5 parts by weight. Note that in Comparative Example 2, the comparative water-absorbing resin particles (2) are treated as being an end product. As such, the comparative water-absorbing resin particles (2) were considered to be a comparative water-absorbing agent (2).

The comparative particulate hydrogel (2) had a weight average particle diameter (D50) of 683 μm. The comparative water-absorbing resin powder (2) had a moisture content of 3.9 weight %, a CRC of 33.1 g/g, a weight average particle diameter (D50) of 371 μm, a logarithmic standard deviation ($\sigma\zeta$) of a particle size distribution of 0.35, an average gap radius of 261 μm, and a specific surface area of 32.8 m$^2$/kg. Physical properties of the comparative water-absorbing resin powder (2) are shown in Table 1, and physical properties of the comparative water-absorbing agent (2) are shown in Table 2. The particles of the comparative water-absorbing agent (2) had a non-uniformly pulverized particle shape.

Comparative Example 3

1.0 part by weight of a liquid permeability improving agent identical to that used in Comparative Example 1 was added to 100 parts by weight of the comparative water-absorbing resin particles (2) obtained in Comparative Example 2 and mixed until uniformity was obtained. Thereafter, the mixture was crushed until it passed through a JIS standard sieve having a mesh size of 710 μm, so that a comparative water-absorbing agent (3) was obtained as an end product. Physical properties of the comparative water-absorbing agent (3) are shown in Table 2. The particles of the comparative water-absorbing agent (3) had a non-uniformly pulverized particle shape.

Comparative Example 4

A comparative water-absorbing agent (4) was synthesized in conformity with Referential Example 1 of European Patent Application Publication No. 1473010 (Patent Literature 16).

Specifically, a comparative aqueous monomer solution (4) was obtained by dissolving 8.1 parts by weight of polyethyleneglycol diacrylate (average n number: 8) into 5500 parts by weight of a 38 weight % aqueous sodium acrylate solution (neutralization rate: 71 mol %). The comparative aqueous monomer solution (4) was degassed in a nitrogen atmosphere for 30 minutes.

Next, the comparative aqueous monomer solution (4) was supplied to a stainless steel twin-arm kneader, and gas in the system was replaced with nitrogen gas while the temperature of the comparative aqueous monomer solution (4) was kept at 30° C. The twin-arm kneader had an openable/closable lid, a jacket, and two sigma type blades.

Next, while the comparative aqueous monomer solution (4) was stirred, as a polymerization initiator, 2.4 parts by weight of ammonium persulfate and 0.12 parts by weight of L-ascorbic acid were added thereto. A polymerization reaction commenced approximately 1 minute thereafter. The polymerization reaction was allowed to continue as is, and after 60 minutes had passed, a comparative hydrogel (4) was removed from the twin-arm kneader. The temperature during the polymerization reaction was in a range of 20° C. to 95° C.

The comparative hydrogel (4) had been grain refined such that its size was approximately 5 mm. The comparative hydrogel (4) was spread onto a metal gauze with a mesh size of 300 μm (50 mesh) and then placed in a hot air dryer. The comparative hydrogel (4) was then dried by passing hot air at a temperature of 150° C. over the comparative hydrogel (4) for 90 minutes, such that a comparative dried polymer (4) was obtained. Next, the comparative dried polymer (4) was pulverized with use of a vibration mill. Thereafter, the comparative dried polymer (4) thus pulverized was classified with use of two JIS standard sieves having respective mesh sizes of 850 μm and 106 μm. In this way, a comparative water-absorbing resin powder (4) whose particles had a non-uniformly pulverized particle shape was obtained.

The comparative water-absorbing resin powder (4) obtained through the above series of operations had a moisture content of 3.5 weight %, a CRC of 38.5 g/g, a weight average particle diameter (D50) of 400 μm, a logarithmic standard deviation ($\sigma\zeta$) of a particle size distribution of 0.39, and an average gap radius of 316 μm. Physical properties of the comparative water-absorbing resin powder (4) are shown in Table 1.

Next, 3.9 parts by weight of a comparative surface-crosslinking agent solution (4) composed of 0.4 parts by weight of 1,4-butanediol, 0.5 parts by weight of propylene glycol, and 3.0 parts by weight of deionized water was added to 100 parts by weight of the comparative water-absorbing resin powder (4) and mixed until uniformity was obtained. In this way, a comparative humidified mixture (4) was obtained. The comparative humidified mixture (4) was then subjected to a heating treatment at 210° C. for 40 minutes and subsequently force-cooled to 60° C. so that comparative water-absorbing resin particles (4) were obtained. Note that in Comparative Example 4, the comparative water-absorbing resin particles (4) are treated as being an end product. As such, the comparative water-absorbing resin particles (4) were considered to be a comparative water-absorbing agent (4). Physical properties of the comparative water-absorbing agent (4) are shown in Table 2. The particles of the comparative water-absorbing agent (4) had a non-uniformly pulverized particle shape. The degradable soluble component of the comparative water-absorbing agent (4) was measured as being 33 weight %.

Comparative Example 5

A comparative water-absorbing agent (5) was synthesized in conformity with Referential Example 5 of European Patent Application Publication No. 1473010 (Patent Literature 16).

Specifically, a comparative aqueous monomer solution (5) was obtained by dissolving 5.8 parts by weight of polyethyleneglycol diacrylate (average n number: 8) into 5500 parts by weight of a 38 weight % aqueous sodium acrylate solution (neutralization rate: 71 mol %). The comparative aqueous monomer solution (5) was degassed in a nitrogen atmosphere for 30 minutes.

Next, the comparative aqueous monomer solution (5) was supplied to a stainless steel twin-arm kneader, and gas in the system was replaced with nitrogen gas while the temperature of the comparative aqueous monomer solution (5) was kept at 30° C. The twin-arm kneader had an openable/closable lid, a jacket, and two sigma type blades.

Next, while the comparative aqueous monomer solution (5) was stirred, as a polymerization initiator, 3.0 parts by weight of sodium persulfate and 0.03 parts by weight of L-ascorbic acid were added thereto. A polymerization reaction commenced approximately 1 minute thereafter. The polymerization reaction was allowed to continue as is, and after 60 minutes had passed, a comparative hydrogel (5) was removed from the twin-arm kneader. The temperature during the polymerization reaction was in a range of 20° C. to 95° C.

The comparative hydrogel (5) had been grain refined such that its size was approximately 5 mm. The comparative hydrogel (5) was spread onto a metal gauze with a mesh size of 300 μm (50 mesh) and then placed in a hot air dryer. The comparative hydrogel (5) was then dried by passing hot air at a temperature of 150° C. over the comparative hydrogel (5) for 90 minutes, such that a comparative dried polymer (5) was obtained. Next, the comparative dried polymer (5) was pulverized with use of a vibration mill. Thereafter, the comparative dried polymer (5) thus pulverized was classified with use of two JIS standard sieves having respective mesh sizes of 500 μm and 45 μm and then further classified with use of a metal gauze having a mesh size of 300 μm (50 mesh). In this way, a comparative water-absorbing resin powder (5) whose particles had a non-uniformly pulverized particle shape was obtained.

The comparative water-absorbing resin powder (5) obtained through the above series of operations had a moisture content of 3.3 weight %, a CRC of 43.0 g/g, a weight average particle diameter (D50) of 120 μm, a logarithmic standard deviation ($\sigma\zeta$) of a particle size distribution of 0.20, and an average gap radius of 157 μm. Physical properties of the comparative water-absorbing resin powder (5) are shown in Table 1.

Next, comparative water-absorbing resin particles (5) were obtained by carrying out surface crosslinking in the same manner as in Comparative Example 4. Next, 0.5 parts by weight of bentonite (manufactured by Wako Pure Chemical Industries, Ltd.; product code 029-0055) was added to 100 parts by weight of the comparative water-absorbing resin particles (5) and mixed until uniformity was obtained, such that a comparative water-absorbing agent (5) was obtained as an end product. Physical properties of the comparative water-absorbing agent (5) are shown in Table 2. The particles of the comparative water-absorbing agent (5) had a non-uniformly pulverized particle shape. The degradable soluble component of the comparative water-absorbing agent (5) was measured as being 42 weight %. The comparative water-absorbing agent (5) had a particle size distribution such that particle size was fine. As such, marked deterioration occurred.

Examples 4 to 6

Absorbent bodies (1) to (3) were obtained by uniformly mixing pulp with each of the water-absorbing agents (1) to (3) obtained in Examples 1 to 3, in an amount of 0.6 parts by weight of pulp relative to 0.9 parts by weight of water-absorbing agent.

An amount of liquid updrawn by each of the absorbent bodies (1) to (3) was measured. Table 3 shows the measurement results.

Comparative Examples 6 to 10

Comparative absorbent bodies (1) to (5) were obtained by uniformly mixing pulp with each of the comparative water-absorbing agents (1) to (5) obtained in Comparative Examples 1 to 5, in an amount of 0.6 parts by weight of pulp relative to 0.9 parts by weight of comparative water-absorbing agent.

An amount of liquid updrawn by each of the comparative absorbent bodies (1) to (5) was measured. Table 3 shows the measurement results.

TABLE 1

| | | Moisture content [wt %] | CRC [g/g] | D50 [μm] | $\sigma\zeta$ [—] | Average gap radius [μm] | Specific surface area [m²/kg] |
|---|---|---|---|---|---|---|---|
| Ex. 1 | Water-absorbing resin powder (1) | 3.5 | 35.8 | 360 | 0.37 | 270 | 30.8 |
| Ex. 2 | Water-absorbing resin powder (2) | 3.2 | 35.2 | 353 | 0.38 | 265 | 32.1 |
| Com. Ex. 1 | Com. water-absorbing resin powder (1) | 3.9 | 36.1 | 384 | 0.39 | 305 | 29.8 |
| Com. Ex. 2 | Com. water-absorbing resin powder (2) | 3.9 | 33.1 | 371 | 0.35 | 261 | 32.8 |
| Com. Ex. 4 | Com. water-absorbing resin powder (4) | 3.5 | 38.5 | 400 | 0.39 | 316 | — |
| Com. Ex. 5 | Com. water-absorbing resin powder (5) | 3.3 | 43.0 | 120 | 0.20 | 157 | — |

*In the above table, "Ex." and "Com." are abbreviations of "Example" and "Comparative", respectively.

TABLE 2

|   |   | CRC [g/g] | AAP [g/g] | D50 [μm] | Particle proportion [wt %] [1)] | Average gap radius [μm] | Updraw fluid retention capacity under load | |
|---|---|---|---|---|---|---|---|---|
|   |   |   |   |   |   |   | With 20 cm water column [g/g] | With 30 cm water column [g/g] |
| Ex. 1 | Water absorbing agent (1) | 32.5 | 25.7 | 373 | 6.6 | 175 | 27.0 | 22.3 |
| Ex. 2 | Water absorbing agent (2) | 29.9 | 26.2 | 375 | 6.8 | 157 | 26.4 | 22.4 |
| Ex. 3 | Water absorbing agent (3) | 28.9 | 25.5 | 357 | 6.2 | 150 | 26.1 | 22.7 |
| Com. Ex. 1 | Com. water absorbing agent (1) | 29.2 | 24.5 | 393 | 10.0 | 198 | 24.6 | 19.7 |
| Com. Ex. 2 | Com. water absorbing agent (2) | 27.2 | 24.9 | 370 | 5.6 | 157 | 24.5 | 21.8 |
| Com. Ex. 3 | Com. water absorbing agent (3) | 26.5 | 24.0 | 357 | 3.0 | 187 | 22.9 | 18.6 |
| Com. Ex. 4 | Com. water absorbing agent (4) | 27.5 | 26.0 | 425 | 19.3 | 120 | 20.0 | 17.4 |
| Com. Ex. 5 | Com. water absorbing agent (5) | 29.6 | 19.1 | 130 | 0.0 | 162 | 22.0 | 18.1 |

[1)] Proportion of particles with a particle diameter of 600 μm or more and less than 850 μm.
*In the above table, "Ex." and "Com." are abbreviations of "Example" and "Comparative", respectively.

TABLE 3

|   |   | Absorbent body | |
|---|---|---|---|
|   | Water absorbing agent used |   | Amount of liquid updrawn [g] |
| Ex. 4 | Water absorbing agent (1) | Absorbent body (1) | 23.7 |
| Ex. 5 | Water absorbing agent (2) | Absorbent body (2) | 23.4 |
| Ex. 6 | Water absorbing agent (3) | Absorbent body (3) | 23.4 |
| Com. Ex. 6 | Com. water absorbing agent (1) | Com. absorbent body (1) | 22.1 |
| Com. Ex. 7 | Com. water absorbing agent (2) | Com. absorbent body (2) | 21.0 |
| Com. Ex. 8 | Com. water absorbing agent (3) | Com. absorbent body (3) | 21.9 |
| Com. Ex. 9 | Com. water absorbing agent (4) | Com. absorbent body (4) | 18.9 |
| Com. Ex. 10 | Com. water absorbing agent (5) | Com. absorbent body (5) | 20.5 |

*In the above table, "Ex." and "Com." are abbreviations of "Example" and "Comparative", respectively.

Example 7

A solution (hereinafter referred to as an "aqueous monomer solution") (7) obtained by mixing 2070 g of acrylic acid, 1665 g of a 48 weight % aqueous sodium hydroxide solution, 1765 g of water, 25 g of a 0.5 weight % aqueous diethylenetriamine pentaacetic acid/pentasodium solution, 6.0 g of polyethyleneglycol diacrylate (average n number: 8) as an internal crosslinking agent, 2.0 g of a 10 weight % aqueous solution of polyoxyethylene (20) sorbitane monostearate (manufactured by Kao Corporation) as a surfactant, and 48 g of a 3 weight % aqueous sodium persulfate solution was introduced into a stainless steel twin-arm kneader. The twin-arm kneader had two sigma type blades, an openable/closable lid, and a jacket. The capacity of the twin-arm kneader was 10 L. The jacket temperature of the twin-arm kneader was set to 100° C., and nitrogen gas was introduced into the twin-arm kneader at a rate of 20 L/min.

A concentration of a monomer component in the aqueous monomer solution (7) was 45 weight %. When the aqueous monomer solution (7) was supplied to the twin-arm kneader, the temperature of the aqueous monomer solution (7) increased to 97° C. due to heat of neutralization and heat of dissolution. The increase in temperature caused a decrease in gas solubility, which resulted in very fine gas bubbles forming in the aqueous monomer solution (7). The gas bubbles caused the aqueous monomer solution (7) to become whitish.

The aqueous monomer solution (7) containing the gas bubbles was supplied into the twin-arm kneader, and a polymerization reaction commenced immediately thereafter. The polymerization caused the aqueous monomer solution (7) to become a hydrogel (7), which was gel-crushed by the sigma type blades of the twin-arm kneader. A peak temperature during the polymerization was 101.2° C. In other words, in Example 7, polymerization and gel-crushing were carried out simultaneously, with use of the twin-arm kneader. Through the polymerization and the gel-crushing, a particulate hydrogel (7) having a weight average particle diameter (D50) of 830 μm was obtained. The particulate hydrogel (7) was constituted by foamed particles containing gas bubbles.

Next, the particulate hydrogel (7) was spread onto a metal gauze with a mesh size of 850 μm so as to have a thickness of approximately 50 mm. The particulate hydrogel (7) thus spread was then placed in a hot air dryer. The particulate hydrogel (7) was then dried for 40 minutes with hot air having a temperature of 170° C. and a dew point of 50° C., the hot air being provided from a direction orthogonal to the particulate hydrogel (7) at a speed of 1 m/s. Through this drying operation, a dried polymer (7) was obtained.

Next, the dried polymer (7) was introduced into a roll mill and pulverized. Thereafter, the dried polymer (7) thus pulverized was classified with use of two JIS standard sieves having respective mesh sizes of 710 μm and 106 μm. In this way, a water-absorbing resin powder (7) whose particles were foamed particles having a non-uniformly pulverized particle shape was obtained.

The water-absorbing resin powder (7) obtained through the above series of operations had a moisture content of 4.5 weight %, a CRC of 36.4 g/g, a weight average particle diameter (D50) of 380 μm, a logarithmic standard deviation (σζ) of a particle size distribution of 0.37, and an average gap radius of 291 μm. Physical properties of the water-absorbing resin powder (7) are shown in Table 4.

Next, 3.5 parts by weight of a surface-crosslinking agent solution (7) composed of 0.4 parts by weight of 1,4-butanediol, 0.6 parts by weight of propylene glycol, and 2.5 parts by weight of deionized water was added to 100 parts by weight of the water-absorbing resin powder (7) and mixed until uniformity was obtained. In this way, a humidified mixture (7) was obtained. The humidified mixture (7) was then subjected to a heating treatment at 212° C. for 30 minutes and subsequently force-cooled to 60° C. so that water-absorbing resin particles (7) were obtained.

Next, 1.0 part by weight of a liquid permeability improving agent composed of 0.75 parts by weight of a 50 weight % aqueous aluminum sulfate solution and 0.25 parts by weight of a 60 weight % aqueous sodium lactate solution was added as an additive to 100 parts by weight of the water-absorbing resin particles (7) and mixed until uniformity was obtained. Thereafter, the mixture was crushed until it passed through a JIS standard sieve having a mesh size of 850 μm, so that a water-absorbing agent (7) was obtained as an end product. Physical properties of the water-absorbing agent (7) are shown in Table 5. The particles of the water-absorbing agent (7) were foamed particles having a non-uniformly pulverized particle shape.

Example 8

130 g of acrylic acid, 1355 g of a 37 weight % aqueous sodium acrylate solution, 1.7 g of polyethyleneglycol diacrylate (weight average molecular weight: 523) as an internal crosslinking agent, 5.0 g of polyethylene glycol (manufactured by Wako Pure Chemical Industries, Ltd.; weight average molecular weight: 2000) and 4.5 g of deionized water were introduced into a stainless steel vat-type vessel having a bottom surface measuring 300 mm×220 mm and a height of 60 mm and mixed so that a aqueous monomer solution (8) was obtained. The vat-type vessel had a thermometer, a nitrogen gas inlet tube, and a lid having an exhaust hole.

After the aqueous monomer solution (8) was introduced into the vat-type vessel, the vat-type vessel was immersed in a water bath at a temperature of 10° C. During immersion, the surface of the water was at a height of 10 mm as measured from the bottom of the vat-type vessel.

The vat-type vessel was immersed in and removed from the water bath repeatedly as appropriate such that the temperature of the aqueous monomer solution (8) was controlled to 17° C.±1° C. At the same time, nitrogen gas was introduced into the aqueous monomer solution (8) through the nitrogen gas inlet tube at a rate of 2 L/min for 30 minutes so as to de-gas the aqueous monomer solution (8). Thereafter, the tip of the nitrogen gas inlet tube was moved to a gaseous phase portion inside the vat-type vessel, and while nitrogen gas was introduced into the vat-type vessel, 4.0 g of a 25 weight % aqueous sodium persulfate solution was added to the aqueous monomer solution (8) and stirred for 1 minute with use of a magnetic stirrer. Thereafter, 5.5 g of a 0.2 weight % aqueous L-ascorbic acid solution was added and stirred sufficiently with the magnetic stirrer. A polymerization reaction commenced 30 seconds thereafter.

After the polymerization reaction commenced, stirring was stopped, and polymerization continued while the vat-type vessel was cooled by immersion in the 10° C. water bath. A peak temperature of 105° C. was reached 8 minutes after the commencement of the polymerization. Thereafter, the vat-type vessel was immediately moved to another water bath at a temperature of 50° C., and polymerization continued for 12 minutes as the vat-type vessel was immersed in the 50° C. water bath. Through these operations, a hydrogel (8) was obtained. During immersion, the surface of the water was at a height of 10 mm as measured from the bottom of the vat-type vessel.

Next, the hydrogel (8) was cut into an appropriate size, placed in a "Uni-Pack" (manufactured by SEISANNIPPON-SHA Ltd.), and then allowed to stand still for 1 hour in an incubator at 50° C. Subsequently, the hydrogel (8) which had been kept at 50° C. was supplied to a meat chopper and gel-crushed, such that a particulate hydrogel (8) was obtained. A rotation speed of a screw shaft of the meat chopper was 160 rpm.

Next, the particulate hydrogel (8) was spread onto a metal gauze with a mesh size of 300 μm (50 mesh) and then placed in a hot air dryer. The particulate hydrogel (8) was then dried by passing hot air at a temperature of 190° C. over the particulate hydrogel (8) for 30 minutes, such that a dried polymer (8) was obtained. Next, the dried polymer (8) was introduced into a roll mill and pulverized. Thereafter, the dried polymer (8) thus pulverized was classified with use of two JIS standard sieves having respective mesh sizes of 710 μm and 150 μm. In this way, a water-absorbing resin powder (8) whose particles had a non-uniformly pulverized particle shape was obtained.

The water-absorbing resin powder (8) obtained through the above series of operations had a moisture content of 3.4 weight %, a CRC of 33.3 g/g, a weight average particle diameter (D50) of 396 μm, a logarithmic standard deviation (σζ) of a particle size distribution of 0.38, and an average gap radius of 278 μm. Physical properties of the water-absorbing resin powder (8) are shown in Table 4.

Next, 3.5 parts by weight of a surface-crosslinking agent solution (8) composed of 0.4 parts by weight of ethylene carbonate, 0.6 parts by weight of propylene glycol, and 2.5 parts by weight of deionized water was added to 100 parts by weight of the water-absorbing resin powder (8) and mixed until uniformity was obtained. In this way, a humidified mixture (8) was obtained. The humidified mixture (8) was then subjected to a heating treatment at 205° C. for 35 minutes and subsequently force-cooled to 60° C. so that water-absorbing resin particles (8) were obtained. Note that in Example 8, the water-absorbing resin particles (8) are treated as being an end product. As such, the water-absorbing resin particles (8) were considered to be a water-absorbing agent (8). Physical properties of the water-absorbing agent (8) are shown in Table 5. The particles of the water-absorbing agent (8) had a non-uniformly pulverized particle shape.

In calculating the average gap radius of the water-absorbing resin powder (8) and the water-absorbing agent (8), 0.062 was used as the value of γ. This is because when the each of the water-absorbing resin powder (8) and the water-absorbing agent (8) was immersed in a 0.9 weight % aqueous sodium chloride solution, a supernatant liquid had a surface tension of 0.062 kg/s$^2$.

Comparative Example 11

A comparative water-absorbing agent (11) was synthesized in conformity with Example 13 of International Publication No. 2007/037522 (Patent Literature 18).

Specifically, a comparative aqueous monomer solution (11) was obtained by dissolving 11.3 parts by weight of polyethyleneglycol diacrylate (average n number: 9) into 5460 parts by weight of a 38 weight % aqueous sodium acrylate solution (neutralization rate: 75 mol %). The comparative aqueous monomer solution (11) was degassed in a nitrogen atmosphere for 30 minutes.

Next, the comparative aqueous monomer solution (11) was supplied to a stainless steel twin-arm kneader having a capacity of 10 L, and gas in the system was replaced with nitrogen gas while the temperature of the comparative aqueous monomer solution (11) was kept at 25° C. The twin-arm kneader had an openable/closable lid, a jacket, and two sigma type blades.

Next, while the comparative aqueous monomer solution (11) was stirred, as a polymerization initiator, 30.7 parts by weight of a 10 weight % aqueous sodium persulfate solution and 0.7 parts by weight of a 1 weight % aqueous L-ascorbic acid solution were added thereto. A polymerization reaction commenced approximately 1 minute thereafter. The polymerization reaction was allowed to continue as is, and after 40 minutes had passed, a comparative hydrogel (11) was removed from the twin-arm kneader. The polymerization reaction reached a peak temperature of 86° C., 17 minutes after the commencement of the polymerization.

The comparative hydrogel (11) had been grain refined such that its size was 1 mm to 4 mm. The comparative hydrogel (11) was spread onto a metal gauze with a mesh size of 300 μm (50 mesh) and then placed in a hot air dryer. The comparative hydrogel (11) was then dried by passing hot air at a temperature of 170° C. over the comparative hydrogel (11) for 45 minutes, such that a comparative dried polymer (11) was obtained. Next, the comparative dried polymer (11) was pulverized twice with use of a roll mill. Thereafter, the comparative dried polymer (11) thus pulverized was classified with use of two JIS standard sieves having respective mesh sizes of 600 μm and 106 μm. In this way, a comparative water-absorbing resin powder (11) whose particles had a non-uniformly pulverized particle shape was obtained.

The comparative water-absorbing resin powder (11) obtained through the above series of operations had a moisture content of 4.0 weight %, a CRC of 32.3 g/g, a weight average particle diameter (D50) of 315 μm, a logarithmic standard deviation (σζ) of a particle size distribution of 0.31, and an average gap radius of 264 μm. Physical properties of the comparative water-absorbing resin powder (11) are shown in Table 4.

Next, 3.95 parts by weight of a comparative first surface-crosslinking agent solution (11) composed of 0.35 parts by weight of 1,4-butanediol, 0.6 parts by weight of propylene glycol, and 3.0 parts by weight of deionized water was added to 100 parts by weight of the comparative water-absorbing resin powder (11) and mixed until uniformity was obtained. In this way, a comparative humidified mixture (11) was obtained. Next, the comparative humidified mixture (11) was subjected to a heating treatment at 210° C. for 30 minutes. Thereafter, 1.22 parts by weight of a second comparative surface-crosslinking agent solution (11) composed of 0.02 parts by weight of propylene glycol, 0.5 parts by weight of aluminum sulfate, 0.1 parts by weight of sodium lactate, and 0.6 parts by weight of deionized water were further sprayed onto and mixed with the comparative humidified mixture (11). The obtained mixture was subjected to a heating treatment at 60° C. for 1 hour, so that surface-crosslinked comparative water-absorbing resin particles (11) were obtained.

Thereafter, 0.75 parts by weight of a titanium oxide slurry STS-21 (registered trademark; manufactured by Ishihara Sangyo Kaisha, Ltd.) having properties as described below was added to and mixed with the surface crosslinked comparative water-absorbing resin particles (11).

Physical properties of titanium oxide slurry STS-21 (registered trademark):
TiO$_2$ 40 weight % slurry solution
pH=8.5

Thereafter, the obtained mixture was subjected to a heating treatment at 60° C. for 1 hour. Thereafter, the obtained mixture was passed through a JIS standard sieve having a mesh size of 600 μm, so that a comparative water-absorbing agent (11) was obtained.

Physical properties of the comparative water-absorbing agent (11) are shown in Table 5. The comparative water-absorbing agent (11) had a CRC and an AAP each of which was within a range of ±0.5 g/g as compared to the CRC and AAP of a water-absorbing agent composition (C19) obtained in Example 13 of International Publication No. 2007/037522 (Patent Literature 18). The physical properties of the comparative water-absorbing agent (11) thus nearly matched those of the water-absorbing agent composition (C19). The particles of the comparative water-absorbing agent (11) had a non-uniformly pulverized particle shape.

Comparative Example 12

A comparative water-absorbing agent (12) was synthesized in conformity with Example 14 of International Publication No. 2007/037522 (Patent Literature 18).

Specifically, the comparative water-absorbing agent (12) was obtained by carrying out operations in the same manner as in Comparative Example 11, except that 3.0 parts by weight of zirconia sol ZSL-10T (registered trademark; manufactured by Daiichi Kigenso Kagaku Kogyo Co., Ltd) having properties as described below were used instead of the titanium oxide slurry STS-21 (registered trademark) used in Comparative Example 11.

Physical properties of zirconia sol ZSL-10T (registered trademark)
ZrO$_2$ 10.0 weight % to 10.5 weight % slurry solution
pH=2 to 3
Average particle diameter: approximately 10 nm Physical properties of the comparative water-absorbing agent (12) are shown in Table 5. The comparative water-absorbing agent (12) had a CRC and an AAP each of which was within a range of ±0.5 g/g as compared to the CRC and AAP of a water-absorbing agent composition (C20) obtained in Example 14 of International Publication No. 2007/037522 (Patent Literature 18). The physical properties of the comparative water-absorbing agent (12) thus nearly matched those of the water-absorbing agent composition (C20). The particles of the comparative water-absorbing agent (12) had a non-uniformly pulverized particle shape.

Comparative Example 13

A comparative water-absorbing agent (13) was synthesized in conformity with Example 15 of International Publication No. 2007/037522 (Patent Literature 18).

Specifically, the comparative water-absorbing agent (13) was obtained by carrying out operations in the same manner as in Comparative Example 11, except that 2.0 parts by weight of ceria sol CESL-15N (registered trademark; manufactured by Daiichi Kigenso Kagaku Kogyo Co., Ltd) having properties as described below were used instead of the titanium oxide slurry STS-21 (registered trademark) used in Comparative Example 11.

Physical properties of ceria sol CESL-15N (registered trademark)
$CeO_2$ 15.0 weight % to 15.5 weight % slurry solution
pH=2.5 to 3
Average particle diameter: approximately 10 nm Physical properties of the comparative water-absorbing agent (13) are shown in Table 5. The comparative water-absorbing agent (13) had a CRC and an AAP each of which was within a range of ±0.5 g/g as compared to the CRC and AAP of a water-absorbing agent composition (C21) obtained in Example 15 of International Publication No. 2007/037522 (Patent Literature 18). The physical properties of the comparative water-absorbing agent (13) thus nearly matched those of the water-absorbing agent composition (C21). The particles of the comparative water-absorbing agent (13) had a non-uniformly pulverized particle shape.

Comparative Example 14

A comparative water-absorbing agent (14) was synthesized in conformity with Example 16 of International Publication No. 2007/037522 (Patent Literature 18).

Specifically, the comparative water-absorbing agent (14) was obtained by carrying out operations in the same manner as in Comparative Example 11, except that 3.0 parts by weight of tin oxide sol ($SnO_2$ sol) (manufactured by Daiichi Kigenso Kagaku Kogyo Co., Ltd) having properties as described below were used instead of the titanium oxide slurry STS-21 (registered trademark) used in Comparative Example 11.

Physical properties of tin oxide sol ($SnO_2$ sol)
$SnO_2$ sol 9 weight % to 11 weight % slurry solution
pH=9 to 11
Average particle diameter: approximately 5 nm to 10 nm Physical properties of the comparative water-absorbing agent (14) are shown in Table 5. The comparative water-absorbing agent (14) had a CRC and an AAP each of which was within a range of ±0.5 g/g as compared to the CRC and AAP of a water-absorbing agent composition (C22) obtained in Example 16 of International Publication No. 2007/037522 (Patent Literature 18). The physical properties of the comparative water-absorbing agent (14) thus nearly matched those of the water-absorbing agent composition (C22). The particles of the comparative water-absorbing agent (14) had a non-uniformly pulverized particle shape.

Comparative Example 15

A comparative particulate hydrogel (15) was obtained by cutting the hydrogel (1) obtained in Example 1 to an appropriate size and then supplying the hydrogel (1) to a screw extruder and subjecting the hydrogel (1) to gel-crushing. The rotation speed of a screw shaft of the screw extruder was set to 100 rpm. The comparative particulate hydrogel (15) had a weight average particle diameter (D50) of 1600 μm.

Next, the comparative particulate hydrogel (15) was spread onto a metal gauze with a mesh size of 300 μm (50 mesh) and then placed in a hot air dryer. The comparative particulate hydrogel (15) was then dried by passing hot air at a temperature of 190° C. over the comparative particulate hydrogel (15) for 30 minutes, such that a comparative dried polymer (15) was obtained. Next, the comparative dried polymer (15) was introduced into a roll mill and pulverized. Thereafter, the comparative dried polymer (15) thus pulverized was classified with use of two JIS standard sieves having respective mesh sizes of 850 μm and 150 μm. In this way, a comparative water-absorbing resin powder (15) whose particles had a non-uniformly pulverized particle shape was obtained.

The comparative water-absorbing resin powder (15) obtained through the above series of operations had a moisture content of 3.9 weight %, a CRC of 36.2 g/g, a weight average particle diameter (D50) of 391 μm, a logarithmic standard deviation (σζ) of a particle size distribution of 0.39, an average gap radius of 320 μm, and a specific surface area of 25.0 m$^2$/kg. Physical properties of the comparative water-absorbing resin powder (15) are shown in Table 4.

Next, 3.5 parts by weight of a surface-crosslinking agent solution (1) composed of 0.4 parts by weight of ethylene carbonate, 0.6 parts by weight of propylene glycol, and 2.5 parts by weight of deionized water was added to 100 parts by weight of the comparative water-absorbing resin powder (15) and mixed until uniformity was obtained. In this way, a comparative humidified mixture (15) was obtained. The comparative humidified mixture (15) was then subjected to a heating treatment at 205° C. for 25 minutes and subsequently force-cooled to 60° C. so that a surface-crosslinked comparative water-absorbing resin powder (hereinafter referred to as "comparative water-absorbing resin particles") (15) was obtained.

Next, 1.0 part by weight of a liquid permeability improving agent composed of 0.75 parts by weight of a 50 weight % aqueous aluminum sulfate solution and 0.25 parts by weight of a 60 weight % aqueous sodium lactate solution was added as an additive to 100 parts by weight of the comparative water-absorbing resin particles (15) and mixed until uniformity was obtained. Thereafter, the mixture was crushed until it passed through a JIS standard sieve having a mesh size of 850 μm, so that a comparative water-absorbing agent (15) was obtained as an end product. Physical properties of the comparative water-absorbing agent (15) are shown in Table 5. The particles of the comparative water-absorbing agent (15) had a non-uniformly pulverized particle shape.

Comparative Example 16

A comparative water-absorbing agent (16) was synthesized in conformity with Example 1 of International Publication No. 2008/026783 (Patent Literature 20).

Specifically, 0.4 g of polyethyleneglycol diacrylate (average number of polyethyleneglycol units (average n number): 9) and 5.0 g of hydroxyethyl cellulose SP850 (manufactured by Daicel Chemical Industries, Ltd.) were dissolved into 334 g of an aqueous sodium acrylate solution (neutralization rate: 75 mol %, monomer concentration: 35 weight %) obtained by mixing acrylic acid, aqueous sodium acrylate solution, and deionized water. In this way, a comparative aqueous monomer solution (16) was obtained.

780 g of cyclohexane was introduced into a 2 liter four-neck separable flask equipped with a stirrer, a reflux condenser, a thermometer, a nitrogen gas inlet tube, and a water bath. 4.0 g of sucrose fatty acid ester F-50 (manufactured by Dai-ichi Kogyo Seiyaku Co., Ltd.; HLB=6) was added as a surfactant and stirred at 240 rpm so as to be dispersed in the cyclohexane. Gas in the flask was replaced with nitrogen, and then the temperature of the liquid in the flask was raised to 70° C. Thereafter, the comparative aqueous monomer solution (16) was introduced into the flask.

A reversed phase suspension polymerization commenced after the comparative aqueous monomer solution (16) was introduced. After 15 minutes, the polymerization reaction reached a peak temperature of 74° C. Once the peak temperature was reached, the temperature of the water bath was kept at 70° C. for 30 minutes and then set to 90° C. A resultant comparative hydrogel (16) was dehydrated by azeotropy with the cyclohexane until the comparative hydrogel (16) had a moisture content of 30 weight %.

After the dehydration, stirring was stopped, and the comparative hydrogel (16) precipitated to the bottom of the flask. The comparative hydrogel (16) thus precipitated was then isolated by decantation. The comparative hydrogel (16) thus isolated was spread in a stainless steel vessel and heated at 150° C. for 2 hours in a hot air dryer. This removed cyclohexane and small amounts of water adhering to the comparative hydrogel (16), so that a comparative water-absorbing resin powder (1) having spherical single particles was obtained.

Next, 3.5 parts by weight of a comparative surface-crosslinking agent solution (16) composed of 0.5 parts by weight of propylene glycol, 0.3 parts by weight of 1,4-butanediol, and 2.7 parts by weight of deionized water was added to 100 parts by weight of the comparative water-absorbing resin powder (16) and mixed until uniformity was obtained. In this way, a comparative humidified mixture (16) was obtained. The comparative humidified mixture (16) was then subjected to a heating treatment at 180° C. for 1 hour and subsequently force-cooled to 60° C. so that comparative water-absorbing resin particles (16) were obtained.

Next, 1.1 parts by weight of a liquid permeability improving agent composed of 0.5 parts by weight of aluminum sulfate and 0.6 parts by weight of deionized water was added as an additive to 100 parts by weight of the comparative water-absorbing resin particles (16). The resultant mixture was subjected to a heating treatment at 60° C. for 1 hour in a hot air dryer, so that a comparative water-absorbing agent (16) which was spherical was obtained as an end product.

Physical properties of the comparative water-absorbing agent (16) are shown in Table 5. The comparative water-absorbing agent (16) had a CRC and an AAP each of which was within a range of ±0.5 g/g as compared to the CRC and AAP of a water-absorbing agent (Ex1) obtained in Example 1 of International Publication No. 2008/026783 (Patent Literature 20). The physical properties of the comparative water-absorbing agent (16) thus nearly matched those of the water-absorbing agent (Ex1). The comparative water-absorbing agent (16) had an average gap radius without load which was measured as being 320 μm.

Comparative Example 17

A comparative water-absorbing agent (17) was synthesized in conformity with Example 2 of International Publication No. 2008/026783 (Patent Literature 20).

Specifically, 92 g (1.02 mol) of an 80 weight % aqueous acrylic acid solution was introduced into a 500 mL Erlenmeyer flask. While the Erlenmeyer flask was cooled with ice, 146.0 g of a 21.0 weight % aqueous sodium hydroxide solution was added dropwise to the 80 weight % aqueous acrylic acid solution, so that an acrylic acid partially neutralized salt aqueous solution (17-1) (neutralization rate: 75 mol %; monomer concentration: 38 weight %) was prepared.

9.2 mg (53 μmol) of ethyleneglycoldiglycidyl ether and 92 mg (0.34 mmol) of potassium persulfate were added to the acrylic acid partially neutralized salt aqueous solution (17-1) so that a comparative aqueous monomer solution (17-1) for a first stage of reversed phase suspension polymerization was obtained.

Meanwhile, 340 g (500 mL) of n-heptane was introduced into a 2 liter five-neck cylindrical round-bottom flask equipped with a stirrer, two-stage paddle blades, a reflux condenser, a dropping funnel, and a nitrogen gas inlet tube. 0.92 g of sucrose fatty acid ester (HLB=3.0) serving as a surfactant was added and dissolved into the n-heptane. Thereafter, the temperature of the resultant liquid was controlled to 35° C.

To the resultant liquid, the comparative aqueous monomer solution (17-1) for the first stage of reversed phase suspension polymerization was added, and temperature was maintained at 35° C. As the liquid was stirred, the comparative aqueous monomer solution (17-1) was suspended in the liquid, and gas in the system was replaced with nitrogen gas. Thereafter, the temperature of the resultant suspension was raised to 70° C., and the first stage of reversed phase suspension polymerization was carried out.

Next, in a separate step, 92 g (1.02 mol) of an 80 weight % aqueous acrylic acid solution was introduced into a 500 mL Erlenmeyer flask. While the Erlenmeyer flask was cooled with ice, 146.0 g of a 21.0 weight % aqueous sodium hydroxide solution was added dropwise to the 80 weight % aqueous acrylic acid solution, so that an acrylic acid partially neutralized salt aqueous solution (17-2) (neutralization rate: 75 mol %; monomer concentration: 38 weight %) was prepared.

9.2 mg (53 μmol) of ethyleneglycoldiglycidyl ether and 92 mg (0.34 mmol) of potassium persulfate were added to the acrylic acid partially neutralized salt aqueous solution (17-2) so that a comparative aqueous monomer solution (17-2) for a second stage of reversed phase suspension polymerization was obtained.

After the first stage of reversed phase suspension polymerization finished, a polymerization slurry was cooled to 23° C., and the comparative aqueous monomer solution (17-2) for the second stage of reversed phase suspension polymerization was added dropwise to the system while the surfactant was in a separated state. Gas in the system was replaced with nitrogen gas while stirring was carried out for 30 minutes and while the temperature was kept at 23° C. Thereafter, the temperature was raised to 70° C. and the second stage of the reversed phase suspension polymerization was carried out.

After the reversed phase suspension polymerization finished, 250 g of water was removed from the azeotropic mixture of n-heptane and water by reheating. Thereafter, 368 mg (2.11 mmol) of ethyleneglycoldiglycidyl ether was added as a post-crosslinking agent. A post-crosslinking reaction was carried out at 80° C. for 2 hours in the presence of 45 g of water. After the crosslinking reaction, n-heptane and water in the system were removed by heating and evaporation. In this way, a comparative water-absorbing resin powder (17) composed of spherical granulated particles (granulated particles composed of spherical particles, in a grape-bunch-like form) was obtained.

Next, 5.3 parts by weight of a comparative surface-crosslinking agent solution (17) composed of 0.8 parts by weight of propylene glycol, 0.5 parts by weight of 1,4- butanediol, and 4.0 parts by weight of deionized water was added to 100 parts by weight of the comparative water-absorbing resin powder (17) and mixed until uniformity was obtained. In this way, a comparative humidified mixture (17) was obtained. The comparative humidified mixture (17) was then subjected to a heating treatment at 185° C. for 2 hours and subsequently force-cooled to 60° C. so that comparative water-absorbing resin particles (17) were obtained.

Next, 1.1 parts by weight of a liquid permeability improving agent composed of 0.5 parts by weight of aluminum sulfate and 0.6 parts by weight of deionized water was added as an additive to 100 parts by weight of the comparative water-absorbing resin particles (17). The resultant mixture was subjected to a heating treatment at 60° C. for 1 hour in a hot air dryer, so that a comparative water-absorbing agent (17) which was composed of spherical granulated particles was obtained as an end product.

Physical properties of the comparative water-absorbing agent (17) are shown in Table 5. The comparative water-absorbing agent (17) had a CRC and an AAP each of which was within a range of ±0.5 g/g as compared to the CRC and AAP of a water-absorbing agent (Ex2) obtained in Example 2 of International Publication No. 2008/026783 (Patent Literature 20). The physical properties of the comparative water-absorbing agent (17) thus nearly matched those of the water-absorbing agent (Ex2). The comparative water-absorbing agent (17) had an average gap radius without load which was measured as being 290 μm.

Comparative Example 18

A comparative water-absorbing agent (18) was synthesized in conformity with Example 3 of International Publication No. 2008/026783 (Patent Literature 20).

Specifically, 12.0 parts by weight of polyethyleneglycol diacrylate (average number of polyethyleneglycol units (average n number): 9) was dissolved into 5452 parts by weight of an aqueous sodium acrylate solution (neutralization rate: 71 mol %, monomer concentration: 41 weight %) obtained by mixing acrylic acid, aqueous sodium acrylate solution, and deionized water. In this way, a comparative aqueous monomer solution (18) was obtained.

The comparative aqueous monomer solution (18) was supplied into a reactor formed by attaching a lid to a twin-arm stainless steel kneader having a capacity of 10 liters and equipped with two sigma-type blades and a jacket. While the comparative aqueous monomer solution (18) was kept a 25° C., nitrogen gas was blown into the comparative aqueous monomer solution (18) so that oxygen dissolved in the comparative aqueous monomer solution (18) was removed.

Next, while the comparative aqueous monomer solution (18) was stirred, 31 parts by weight of a 10 weight % aqueous sodium persulfate solution and 4.6 parts by weight of a 1 weight % aqueous L-ascorbic acid solution were added thereto. Polymerization commenced approximately 1 minute thereafter. 15 minutes after the commencement of polymerization, a peak polymerization temperature of 92° C. was reached. A comparative hydrogel (18) was removed from the reactor 40 minutes after the commencement of polymerization.

The comparative hydrogel (18) obtained thusly had been grain refined such that its particles were approximately 1 mm to 4 mm in size. The comparative hydrogel (18) which had been grain refined thusly was spread onto a 50-mesh metal gauze (mesh size: 300 μm) and subjected to hot air drying at 180° C. for 45 minutes, so that a comparative dried polymer (18) was obtained.

The comparative dried polymer (18) was then pulverized with use of a roll mill and subsequently classified with metal gauzes having respective mesh sizes of 850 μm and 300 μm. In this way, a comparative water-absorbing resin powder (18) whose particles had a non-uniformly pulverized particle shape was obtained.

100 g of the comparative water-absorbing resin powder (18) obtained thusly was supplied to a homogenizer (manufactured by Nippon Seiki Co., Ltd., high speed homogenizer, Model: MX-7) and polished for 5 minutes at a rotation speed of 6,000 rpm. Thereafter, the comparative water-absorbing resin powder (18) was classified with metal gauzes having respective mesh sizes of 850 μm and 300 μm. In this way, a polished comparative water-absorbing resin powder (18) was obtained.

Next, 3.5 parts by weight of a comparative surface-crosslinking agent solution (18) composed of 0.5 parts by weight of propylene glycol, 0.3 parts by weight of 1,4-butanediol, and 2.7 parts by weight of deionized water was added to 100 parts by weight of the polished comparative water-absorbing resin powder (18) and mixed until uniformity was obtained. In this way, a comparative humidified mixture (18) was obtained. The comparative humidified mixture (18) was then subjected to a heating treatment at 180° C. for 1 hour and subsequently force-cooled to 60° C. so that comparative water-absorbing resin particles (18) were obtained.

Next, 1.1 parts by weight of a liquid permeability improving agent composed of 0.5 parts by weight of aluminum sulfate and 0.6 parts by weight of deionized water was added as an additive to 100 parts by weight of the comparative water-absorbing resin particles (18). The resultant mixture was subjected to a heating treatment at 60° C. for 1 hour in a hot air dryer, so that a comparative water-absorbing agent (18) whose particles had a non-uniformly pulverized particle shape was obtained as an end product.

Physical properties of the comparative water-absorbing agent (18) are shown in Table 5. The comparative water-absorbing agent (18) had a CRC and an AAP each of which was within a range of ±0.5 g/g as compared to the CRC and AAP of a water-absorbing agent (Ex3) obtained in Example 3 of International Publication No. 2008/026783 (Patent Literature 20). The physical properties of the comparative water-absorbing agent (18) thus nearly matched those of the water-absorbing agent (Ex3). The comparative water-absorbing agent (18) had an average gap radius without load which was measured as being 250 μm.

Comparative Example 19

A comparative water-absorbing agent (19) was synthesized in conformity with Comparative Example 5 of International Publication No. 2008/026783 (Patent Literature 20).

Specifically, 12.0 parts by weight of polyethyleneglycol diacrylate (average number of polyethyleneglycol units (average n number): 9) was dissolved into 5452 parts by weight of an aqueous sodium acrylate solution (neutralization rate: 71 mol %, monomer concentration: 41 weight %) obtained by mixing acrylic acid, aqueous sodium acrylate solution, and deionized water. In this way, a comparative aqueous monomer solution (19) was obtained.

The comparative aqueous monomer solution (19) was supplied into a reactor formed by attaching a lid to a twin-arm stainless steel kneader having a capacity of 10 liters and equipped with two sigma-type blades and a jacket. While the comparative aqueous monomer solution (19) was kept a 25° C., nitrogen gas was blown into the comparative aqueous monomer solution (19) so that oxygen dissolved in the comparative aqueous monomer solution (19) was removed.

Next, while the comparative aqueous monomer solution (19) was stirred, 31 parts by weight of a 10 weight % aqueous sodium persulfate solution and 4.6 parts by weight of a 1 weight % aqueous L-ascorbic acid solution were added thereto. Polymerization commenced approximately 1 minute thereafter. 15 minutes after the commencement of polymerization, a peak polymerization temperature of 92° C. was reached. A comparative hydrogel (19) was removed from the reactor 40 minutes after the commencement of polymerization.

The comparative hydrogel (19) obtained thusly had been grain refined such that its particles were approximately 1 mm to 4 mm in size. The comparative hydrogel (19) which had been grain refined thusly was spread onto a 50-mesh metal gauze (mesh size: 300 μm) and subjected to hot air drying at 180° C. for 45 minutes, so that a comparative dried polymer (19) was obtained.

The comparative dried polymer (19) was then pulverized with use of a roll mill and subsequently classified with metal gauzes having respective mesh sizes of 710 μm and 150 μm. In this way, a comparative water-absorbing resin powder (19) whose particles had a non-uniformly pulverized particle shape was obtained.

Next, 3.9 parts by weight of a comparative surface-crosslinking agent solution (19) composed of 0.6 parts by weight of propylene glycol, 0.3 parts by weight of 1,4-butanediol, and 3.0 parts by weight of deionized water was added to 100 parts by weight of the comparative water-absorbing resin powder (19) and mixed until uniformity was obtained. In this way, a comparative humidified mixture (19) was obtained. The comparative humidified mixture (19) was then subjected to a heating treatment at 180° C. for 1 hour and subsequently force-cooled to 60° C. so that comparative water-absorbing resin particles (19) were obtained.

Next, 1.1 parts by weight of a liquid permeability improving agent composed of 0.5 parts by weight of aluminum sulfate and 0.6 parts by weight of deionized water was added as an additive to 100 parts by weight of the comparative water-absorbing resin particles (19). The resultant mixture was subjected to a heating treatment at 60° C. for 1 hour in a hot air dryer, so that a comparative water-absorbing agent (19) whose particles had a non-uniformly pulverized particle shape was obtained as an end product.

Physical properties of the comparative water-absorbing agent (19) are shown in Table 5. The comparative water-absorbing agent (19) had a CRC and an AAP each of which was within a range of ±0.5 g/g as compared to the CRC and AAP of a comparative water-absorbing agent (C-Ex5) obtained in Comparative Example 5 of International Publication No. 2008/026783 (Patent Literature 20). The physical properties of the comparative water-absorbing agent (19) thus nearly matched those of the water-absorbing agent (C-Ex5). The comparative water-absorbing agent (19) had an average gap radius without load which was measured as being 120 μm, an updraw fluid retention capacity under load with a 30 cm water column of 18.2 g/g, and an updraw fluid retention capacity under load with a 20 cm water column of 21.7 g/g.

Comparative Example 20

A comparative water-absorbing agent (20) was synthesized in conformity with Reference Example 8 of European Patent Application Publication No. 1429703 (Patent Literature 19).

Specifically, 4.9 parts by weight of polyethyleneglycol diacrylate (average number of polyethyleneglycol units (average n number): 8) was dissolved into 5500 parts by weight of an aqueous sodium acrylate solution (neutralization rate: 75 mol %, monomer concentration: 33 weight %). In this way, a comparative aqueous monomer solution (20) was obtained. The comparative aqueous monomer solution (20) was degassed in a nitrogen atmosphere for 30 minutes.

The comparative aqueous monomer solution (20) was supplied into a twin-arm stainless steel kneader equipped with two sigma-type blades, an openable/closable lid, and a jacket. While the comparative aqueous monomer solution (20) was kept a 30° C., nitrogen gas was blown into the comparative aqueous monomer solution (20) so that gas in the system was replaced with nitrogen.

Next, while the comparative aqueous monomer solution (20) was stirred, 2.4 parts by weight of ammonium persulfate and 0.12 parts by weight of L-ascorbic acid were added thereto. Polymerization commenced approximately 1 minute thereafter. Polymerization was carried out in a temperature range of 30° C. to 90° C. A comparative hydrogel (20) was removed from the kneader 60 minutes after the commencement of polymerization.

The comparative hydrogel (20) obtained thusly had been grain refined such that its particles were approximately 5 mm in size. The comparative hydrogel (20) which had been grain refined thusly was spread onto a 50-mesh metal gauze (mesh size: 300 μm) and subjected to hot air drying at 150° C. for 90 minutes, so that a comparative dried polymer (20) was obtained.

The comparative dried polymer (20) was then pulverized with use of a vibration mill and subsequently classified with a 20-mesh metal gauze. In this way, a comparative water-absorbing resin powder (20) whose particles had a non-uniformly pulverized particle shape was obtained. The comparative water-absorbing resin powder (20) had a weight average particle diameter (D50) of 340 μm, and a proportion of particles with a particle diameter of less than 106 μm was 3 weight %.

Next, a comparative surface-crosslinking agent solution (20) composed of 0.05 parts by weight of ethyleneglycoldiglycidyl ether, 0.9 parts by weight of propylene glycol, 3 parts by weight of deionized water, and 1 part by weight of isopropyl alcohol was added to 100 parts by weight of the comparative water-absorbing resin powder (20) and mixed until uniformity was obtained. In this way, a comparative humidified mixture (20) was obtained. Next, the comparative humidified mixture (20) was subjected to a heating treatment at 195° C. for 40 minutes and then force-cooled to 60° C. so that comparative water-absorbing resin particles (20) were obtained. Note that in Comparative Example 20, the comparative water-absorbing resin particles (20) are treated as being an end product. As such, the comparative water-absorbing resin particles (20) were considered to be a comparative water-absorbing agent (20).

Physical properties of the comparative water-absorbing agent (20) are shown in Table 5. The comparative water-absorbing agent (20) had a CRC and an AAP each of which was within a range of ±0.5 g/g as compared to the CRC and AAP of a water-absorbing resin (4) obtained in Reference Example 8 of European Patent Application Publication No.

1429703 (Patent Literature 19). The physical properties of the comparative water-absorbing agent (20) thus nearly matched those of the water-absorbing resin (4). The comparative water-absorbing agent (20) had an average gap radius without load which was measured as being 125 μm, an updraw fluid retention capacity under load with a 30 cm water column of 19.0 g/g, and an updraw fluid retention capacity under load with a 20 cm water column of 23.3 g/g. Furthermore, a degradable soluble component of the comparative water-absorbing agent (20) was measured as being 34 weight %. It was thus confirmed that the surfaces of particles had begun to dissolve due to deterioration.

Comparative Example 21

A comparative water-absorbing agent (21) was synthesized in conformity with Example 1 of International Publication No. 2011/126079 (Patent Literature 3).

Specifically, a comparative aqueous monomer solution (21) composed of 193.3 parts by weight of acrylic acid, 64.4 parts by weight of a 48 weight % aqueous sodium hydroxide solution, 1.26 parts by weight of polyethyleneglycol diacrylate (average number of polyethyleneglycol units (average n number): 9), 52 parts by weight of a 0.1 weight % aqueous pentasodium ethylenediamine tetra(methylene phosphonate) solution, and 134 parts by weight of deionized water was prepared.

Next, the comparative aqueous monomer solution (21) whose temperature had been adjusted to 40° C. was continuously supplied by a metering pump, and then 97.1 parts by weight of a 48 weight % aqueous sodium hydroxide solution was continuously line-mixed with the comparative aqueous monomer solution (21). Thereafter, 8.05 parts by weight of a 4 weight % aqueous sodium persulfate solution was continuously line-mixed with the comparative aqueous monomer solution (21), and then a resultant mixture was continuously supplied into a continuous polymerization device having a planar polymerization belt with dams at both ends, so that the supplied mixture had a thickness of approximately 7.5 mm. Thereafter, polymerization (polymerization time: 3 minutes) was carried out continuously, so that a belt-shaped comparative hydrogel (21) was obtained.

The belt-shaped comparative hydrogel (21) was continuously cut at regular intervals in the width direction relative to the traveling direction of the polymerization belt so that the cut length was approximately 200 mm. Thereafter, the comparative hydrogel (21) thus cut was supplied to a screw extruder and gel-crushed. The rotation speed of a screw shaft of the screw extruder was set to 115 rpm.

A particulate comparative hydrogel (21) obtained through the gel-crushing was then dispersed onto a through-flow belt and dried at 185° C. for 30 minutes so that a comparative dried polymer (21) was obtained.

The comparative dried polymer (21) was then continuously supplied to a three-stage roll mill, pulverized, and subsequently classified with JIS standard sieves having respective mesh sizes of 710 μm and 175 μm. In this way, a comparative water-absorbing resin powder (21) whose particles had a non-uniformly pulverized particle shape was obtained.

The comparative water-absorbing resin powder (21) obtained through the above series of operations had a CRC of 32.1 g/g, a weight average particle diameter (D50) of 340 μm, and a logarithmic standard deviation (σζ) of a particle size distribution of 0.32. Physical properties of the comparative water-absorbing resin powder (21) are shown in Table 4.

Next, a comparative surface-crosslinking agent solution (21) composed of 0.3 parts by weight of 1,4-butanediol, 0.6 parts by weight of propylene glycol, and 3.0 parts by weight of deionized water was added to the comparative water-absorbing resin powder (21) and mixed until uniformity was obtained. In this way, a comparative humidified mixture (21) was obtained. The comparative humidified mixture (21) was then subjected to a heating treatment at 208° C. for 40 minutes and subsequently force-cooled to 60° C. so that comparative water-absorbing resin particles (21) were obtained.

Next, a liquid permeability improving agent composed of 1.17 parts by weight of a 27.5 weight % aqueous aluminum sulfate solution, 0.196 parts by weight of a 60 weight % aqueous sodium lactate solution, and 0.029 parts by weight of propylene glycol was added as an additive to 100 parts by weight of the comparative water-absorbing resin particles (21) and mixed until uniformity was obtained. Thereafter, the mixture was crushed until it passed through a JIS standard sieve having a mesh size of 710 μm, so that a comparative water-absorbing agent (21) was obtained as an end product.

Physical properties of the comparative water-absorbing agent (21) are shown in Table 5. The comparative water-absorbing agent (21) had a CRC of 27.0 g/g and an AAP of 23.4 g/g, which were outside the respective ranges of the CRC and the AAP of the present invention.

Examples 9 and 10

Absorbent bodies (7) and (8) were obtained by uniformly mixing pulp with each of the water-absorbing agents (7) and (8) obtained in Examples 7 and 8, in an amount of 0.6 parts by weight of pulp relative to 0.9 parts by weight of water-absorbing agent.

An amount of liquid updrawn by each of the absorbent bodies (7) and (8) was measured. Table 6 shows the measurement results.

Comparative Examples 22 to 25

Comparative absorbent bodies (11) to (14) were obtained by uniformly mixing pulp with each of the comparative water-absorbing agents (11) to (14) obtained in Comparative Examples 11 to 14, in an amount of 0.6 parts by weight of pulp relative to 0.9 parts by weight of comparative water-absorbing agent.

An amount of liquid updrawn by each of the comparative absorbent bodies (11) to (14) was measured. Table 6 shows the measurement results.

TABLE 4

| | | Moisture content [wt %] | CRC [g/g] | D50 [μm] | σζ [—] | Average gap radius [μm] | Specific surface area [m²/kg] |
|---|---|---|---|---|---|---|---|
| Ex. 7 | Water-absorbing resin powder (7) | 4.5 | 36.4 | 380 | 0.37 | 291 | — |
| Ex. 8 | Water-absorbing resin powder (8) | 3.4 | 33.3 | 396 | 0.38 | 278 | — |

TABLE 4-continued

|  |  | Moisture content [wt %] | CRC [g/g] | D50 [μm] | σζ [—] | Average gap radius [μm] | Specific surface area [m²/kg] |
|---|---|---|---|---|---|---|---|
| Com. Ex. 11 | Com. water-absorbing resin powder (11) | 4.0 | 32.3 | 315 | 0.31 | 264 | — |
| Com. Ex. 15 | Com. water-absorbing resin powder (15) | 3.9 | 36.2 | 391 | 0.39 | 320 | 25.0 |
| Com. Ex. 21 | Com. water-absorbing resin powder (21) | — | 32.1 | 340 | 0.32 | — | — |

*In the above table, "Ex." and "Com." are abbreviations of "Example" and "Comparative", respectively.

TABLE 6

|  | Water absorbing agent used | Absorbent body | Amount of liquid updrawn [g] |
|---|---|---|---|
| Ex. 9 | Water absorbing agent (7) | Absorbent body (7) | 23.4 |
| Ex. 10 | Water absorbing agent (8) | Absorbent body (8) | 23.0 |
| Com. Ex. 22 | Com. water absorbing agent (11) | Com. absorbent body (11) | 20.1 |
| Com. Ex. 23 | Com. water absorbing agent (12) | Com. absorbent body (12) | 20.5 |
| Com. Ex. 24 | Com. water absorbing agent (13) | Com. absorbent body (13) | 19.9 |
| Com. Ex. 25 | Com. water absorbing agent (14) | Com. absorbent body (14) | 20.3 |

*In the above table, "Ex." and "Com." are abbreviations of "Example" and "Comparative", respectively.

TABLE 5

|  |  | CRC [g/g] | AAP [g/g] | D50 [μm] | Particle proportion [1) [wt %] | Average gap radius [μm] | Updraw fluid retention capacity under load | |
|---|---|---|---|---|---|---|---|---|
|  |  |  |  |  |  |  | With 20 cm water column [g/g] | With 30 cm water column [g/g] |
| Ex. 7 | Water absorbing agent (7) | 28.8 | 25.5 | 377 | 4.9 | 175 | 26.3 | 21.7 |
| Ex. 8 | Water absorbing agent (8) | 29.6 | 26.0 | 380 | 5.0 | 158 | 25.8 | 21.3 |
| Com. Ex. 11 | Com. water absorbing agent (11) | 27.9 | 22.9 | 310 | 0.0 | 164 | 22.0 | 18.5 |
| Com. Ex. 12 | Com. water absorbing agent (12) | 27.1 | 23.2 | 315 | 0.0 | 167 | 22.4 | 18.3 |
| Com. Ex. 13 | Com. water absorbing agent. (13) | 27.2 | 23.9 | 310 | 0.0 | 181 | 22.7 | 18.8 |
| Com. Ex. 14 | Com. water absorbing agent (14) | 27.1 | 23.1 | 319 | 0.0 | 160 | 22.2 | 18.0 |
| Com. Ex. 15 | Com. water absorbing agent (15) | 29.9 | 24.5 | 388 | 10.7 | 200 | 22.0 | 17.3 |
| Com. Ex. 16 | Com. water absorbing agent (16) | 26.5 | 23.1 | 344 | 2.4 | 320 | — | — |
| Com. Ex. 17 | Com. water absorbing agent (17) | 26.7 | 20.2 | 345 | 2.4 | 290 | — | — |
| Com. Ex. 18 | Com. water absorbing agent (18) | 26.4 | 22.8 | 499 | 27.5 | 250 | — | — |
| Com. Ex. 19 | Com. water absorbing agent (19) | 27.7 | 23.3 | 324 | 0.3 | 120 | 21.7 | 18.2 |
| Com. Ex. 20 | Com. water absorbing agent (20) | 32.0 | 25.0 | 290 | — | 125 | 23.3 | 19.0 |
| Com. Ex. 21 | Com. water absorbing agent (21) | 27.0 | 23.4 | — | — | — | — | — |

1) Proportion of particles with a particle diameter of 600 μm or more and less than 850 μm.
*In the above table, "Ex." and "Com." are abbreviations of "Example" and "Comparative", respectively.

Examples 11 and 12

The water-absorbing agents (1) and (3) obtained in Examples 1 and 3 were used and evaluated with regards to re-wet and updraw distance in an inclined state. Table 7 shows the evaluation results.

Comparative Examples 26 and 27

The comparative water-absorbing agents (1) and (3) obtained in Comparative Examples 1 and 3 were used and evaluated with regards to re-wet and updraw distance in an inclined state. Table 7 shows the evaluation results.

TABLE 7

| | Water absorbing agent used | Re-wet in inclined state [g] | Updraw distance Upward [cm] | Updraw distance Downward [cm] |
|---|---|---|---|---|
| Ex. 11 | Water absorbing agent (1) | 17.6 | 10 | 12 |
| Ex. 12 | Water absorbing agent (3) | 17.4 | 11 | 12 |
| Com. Ex. 26 | Com. water absorbing agent (1) | 20.5 | 9 | 16 |
| Com. Ex. 27 | Com. water absorbing agent (3) | 23.2 | 10 | 16 |

*In the above table, "Ex." and "Com." are abbreviations of "Example" and "Comparative", respectively.

[Summary]

The results of Comparative Example 4, Comparative Example 5, Comparative Examples 11 to 14, Comparative Examples 16 to 19, and Comparative Example 20 indicate that Patent Literatures 18, 19, and 21, which disclose an average gap radius, and Patent Literature 20, which discloses a gap radius index under pressure, each fail to disclose a water-absorbing agent in accordance with the present invention and a method for producing the water-absorbing agent in accordance with the present invention. Furthermore, the results of Comparative Example 21 indicate that Patent Literature 3 similarly fails to disclose a water-absorbing agent in accordance with the present invention and a method for producing the water-absorbing agent in accordance with the present invention.

As can be seen from Tables 2, 3, 5, and 6, a water-absorbing agent in accordance with an embodiment of the present invention has a high updraw fluid retention capacity under load and, even when used in an absorbent body, has an excellent ability to suck up liquid against the force of gravity.

Specifically, a comparison between Examples 1 to 3, 7, and 8 and Comparative Examples 2, 3, and 12 to 14 (see Tables 2 and 5) indicates that controlling the CRC of a water-absorbing agent so as to be 28 g/g or more improves the updraw fluid retention capacity under load of the water-absorbing agent. However, a comparison between Examples 1 to 3 and Comparative Examples 4 and 5 (see Table 2) indicates that even with a high CRC of 28 g/g or more, in a case where the weight average particle diameter (D50) does not fall in a range of 300 μm or more and less than 400 μm, the updraw fluid retention capacity under load of the water-absorbing agent will not be improved. Furthermore, a comparison between Examples 7 and 8 and Comparative Example 11 (see Table 5) indicates that even with a high CRC of 28 g/g or more, in a case where the fluid retention capacity under pressure (AAP) of a water-absorbing agent is not 24 g/g or more, the updraw fluid retention capacity under load of the water-absorbing agent will not be improved. Still further, a comparison between Examples 1 to 3 and Comparative Example 1 (see Table 2) indicates that in a case where the average gap radius of a water-absorbing agent is not less than 180 μm, the updraw fluid retention capacity under load of the water-absorbing agent will not be improved.

A comparison between Examples 1, 2, 7, and 8 and Comparative Examples 1 to 5, 11, and 15 (see Tables 1 and 4) indicates that, in a method for producing a water-absorbing agent in accordance with an embodiment of the present invention, it is possible to: control a CRC of a water-absorbing resin powder before surface-crosslinking through an amount of crosslinking agent used during polymerization (comparison between Example 1 and Comparative Example 2); control particle size mainly through pulverization and classification performed after drying (comparison between Example 1 and Comparative Example 1); and control average gap radius through gel-crushing and particle size (comparison between Example 1 and Comparative Examples 1 and 15).

A comparison between the physical properties of water-absorbing resin powders before surface-crosslinking (as shown in Table 1) and the physical properties of water-absorbing agents after surface-crosslinking (as shown in Table 2) indicates that it is possible to obtain a water-absorbing agent having an excellent updraw fluid retention capacity under load by carrying out the novel method for producing a water-absorbing agent in accordance with an embodiment of the present invention, in which surface-crosslinking is performed on a water-absorbing resin powder whose CRC, weight average particle diameter (D50), and average gap radius have been controlled to be within appropriate ranges.

Tables 3 and 6 indicate that using a water-absorbing agent in accordance with an embodiment of the present invention (water-absorbing agents (1) to (3), (7), and (8)) in an absorbent body makes it possible to obtain an absorbent body whose ability to suck up liquid against the force of gravity (updraw fluid retention amount under load) is improved to a range of 23.0 g to 23.7 g, as compared to an absorbent body which uses one of the comparative water-absorbing agents (1) to (5) and (11) to (14) (updraw fluid retention amount under load: 18.9 g to 22.1 g).

Table 7 indicates that, with regards to core acquisition in an inclined state (which had not been a focus in conventional techniques), using a water-absorbing agent in accordance with an embodiment of the present invention in a sanitary product (particularly in a disposable diaper) greatly reduces re-wet in an inclined state. With the comparative water-absorbing agents, re-wet in an inclined state was in a range of 20.5 g to 23.2 g, but with the water-absorbing agents in accordance with an embodiment of the present invention, the re-wet in an inclined state was in a range of 17.4 g to 17.6 g. A comparison of upward and downward updraw distances as seen in Table 7 indicates that with a sanitary product using a water-absorbing agent in accordance with an embodiment of the present invention, even in an inclined state, an aqueous solution is sucked upward against the force of gravity. A downward updraw distance of 16 cm was improved greatly to 12 cm. This indicates that the aqueous solution is less likely to flow downward.

In this way, the novelty and inventive step (superiority) of the present invention over conventional art (Patent Literatures 3, 16, 18 to 20, and the like) has been proven even with the Examples and the Comparative Examples. Patent Literatures 1 to 23, including Patent Literatures 3, 16, and 18 to 20 as discussed in Comparative Examples 4, 5, and 11 to 21, fail to disclose a water-absorbing agent in accordance with the present invention and a method for producing the water-absorbing agent in accordance with the present invention.

INDUSTRIAL APPLICABILITY

A water-absorbing agent in accordance with an embodiment of the present invention may be suitably used not only in absorbent articles such as sanitary products (for example, disposable diapers and sanitary napkins), but also in various applications such as animal urine absorbents, urine gelling agents for portable toilets, freshness keeping agents for fruits, vegetables, and the like, drip absorbers for meat and fishery products, ice packs, disposable body warmers, gelling agents for batteries, agricultural and horticultural soil water retaining agents (for plants, soil, and the like), dew condensation preventing agents, industrial waterproofing agents and packing agents, and artificial snow.

REFERENCE SIGNS LIST

100 Measuring apparatus (average gap radius measuring apparatus)
1 Glass filter (porous glass plate)
2 Buechner funnel
3 Duct
4 Liquid containing vessel
5 Support ring
6 Physiological saline (0.9 weight % aqueous sodium chloride solution)
7 Balance
8 Stand
9 Sample (water-absorbing agent)
h Head differential
200 Measuring apparatus (apparatus for measuring updraw fluid retention capacity under load and amount of liquid updrawn by absorbent body)
10 Fritted glass funnel
11 Duct
12 Liquid containing vessel
13 Glass tube
14 Rubber stopper
15 Physiological saline (0.9 weight % aqueous sodium chloride solution)
16 Support cylinder
17 Absorbent paper
18 Metal ring
19 Weight
H Head differential
400 Sanitary product evaluation apparatus
401 Tray
402 Double-side tape
403 Tissue
404 Water-absorbing agent
405 Non-woven fabric
406 Inlet
407 Lid

The invention claimed is:

1. A water-absorbing agent comprising a polyacrylic acid (salt)-based water-absorbing resin as a main component and satisfying all of the following physical properties (a) to (g):
    (a) the weight average particle diameter (D50) is 300 μm or more and less than 400 μm;
    (b) the proportion of particles with a particle diameter of 600 μm or more and less than 850 μm is less than 10 weight %;
    (c) the average gap radius is 100 μm or more and less than 180 μm;
    (d) the CRC is 28 g/g or more and less than 34 g/g;
    (e) the AAP is 24 g/g or more;
    (f) the updraw fluid retention capacity under load with a 30 cm water column is 20 g/g or more; and
    (g) the updraw fluid retention capacity under load with a 20 cm water column is 25 g/g or more.

2. The water-absorbing agent according to claim 1, wherein the water-absorbing agent has the proportion of particles with a particle diameter of 150 μm or more and less than 850 μm which is 90 weight % or more.

3. The water-absorbing agent according to claim 1, wherein the water-absorbing agent further comprises at least one additive selected from among a polyvalent metal salt, a cationic polymer, and inorganic fine particles.

4. The water-absorbing agent according to claim 1, wherein particles of the water-absorbing agent are foamed particles.

5. The water-absorbing agent according to claim 1, wherein particles of the water-absorbing agent have a non-uniformly pulverized particle shape.

6. An absorbent article comprising:
    a liquid permeable top sheet;
    a liquid impermeable back sheet; and
    an absorbent body containing a water-absorbing agent recited in claim 1, the absorbent body being sandwiched between the top sheet and the back sheet.

7. The water-absorbing agent according to claim 1, wherein the water-absorbing agent has the specific surface area of 27 $m^2$/kg or more and 50 $m^2$/kg or less.

8. The water-absorbing agent according to claim 1, which is produced by a method comprising the steps of:
    (A) polymerizing an aqueous monomer solution so that a crosslinked hydrogel polymer is obtained, the aqueous monomer solution containing a monomer and at least one polymerizable internal crosslinking agent, the monomer containing acrylic acid (salt) as a main component;
    (B) gel-crushing said crosslinked hydrogel polymer such that said crosslinked hydrogel polymer has a weight average particle diameter (D50) of 500 pm or more and less than 1500 pm, and then drying said crosslinked hydrogel polymer so that a dried polymer is obtained;
    (C) pulverizing said dried polymer and then classifying said dried polymer so that a water-absorbing resin powder is obtained; and
    (D) surface-crosslinking said water-absorbing resin powder with use of at least one surface-crosslinking agent so that water-absorbing resin particles are obtained,
    said water-absorbing resin powder obtained through the steps (A) to (C) satisfying the following physical properties (1) to (4):
    (1) the CRC is 35 g/g or more;
    (2) the weight average particle diameter (D50) is 300 μm or more and less than 400 μm;
    (3) the logarithmic standard deviation ($\sigma\zeta$) of a particle size distribution is 0.30 or more and less than 0.40; and
    (4) the average gap radius is 100 μm or more and less than 300 μm.

* * * * *